(12) United States Patent
Burbank et al.

(10) Patent No.: US 12,226,557 B2
(45) Date of Patent: *Feb. 18, 2025

(54) FLOW BALANCING DEVICES, METHODS, AND SYSTEMS

(71) Applicant: NxStage Medical, Inc., Lawrence, MA (US)

(72) Inventors: Jeffrey H. Burbank, Manchester, MA (US); Dennis M. Treu, Castle Rock, CO (US); Daniel Joseph Rubery, Jr., Nashua, NH (US); Scott W. Newell, Ipswich, MA (US); James M. Brugger, Newburyport, MA (US); William J. Schnell, Libertyville, IL (US); William K. Weigel, Portland, ME (US); Steven A. White, Hudson, MA (US); Mark T. Wyeth, Andover, MA (US); Jerome James, Vestavia, AL (US); David Desouza, Essex, MA (US); Joseph E. Turk, Jr., North Andover, MA (US); Garrett Casey, Methuen, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/508,533

(22) Filed: Nov. 14, 2023

(65) Prior Publication Data

US 2024/0075191 A1     Mar. 7, 2024

Related U.S. Application Data

(63) Continuation of application No. 17/879,455, filed on Aug. 2, 2022, now Pat. No. 11,850,341, which is a
(Continued)

(51) Int. Cl.
A61M 1/14     (2006.01)
A61M 1/16     (2006.01)
(Continued)

(52) U.S. Cl.
CPC ............ *A61M 1/1605* (2014.02); *A61M 1/14* (2013.01); *A61M 1/1613* (2014.02);
(Continued)

(58) Field of Classification Search
CPC .... A61M 1/14; A61M 1/3403; A61M 1/3434; A61M 1/3437; A61M 1/3441
See application file for complete search history.

(56) References Cited

U.S. PATENT DOCUMENTS

| 4,009,078 A | 2/1977 | Wilkins et al. |
| 4,728,433 A | 3/1988 | Buck et al. |

(Continued)

FOREIGN PATENT DOCUMENTS

| CN | 103957957 A | 7/2014 |
| EP | 2163271 B1 | 3/2010 |

(Continued)

OTHER PUBLICATIONS

Extended European Search Report dated Apr. 24, 2023 for European Patent Application No. 20809725.3.
(Continued)

*Primary Examiner* — Bradley R Spies
(74) *Attorney, Agent, or Firm* — Potomac Law Group, PLLC

(57) ABSTRACT

The disclosed subject matter relates to extracorporeal blood processing or other processing of fluids. Volumetric fluid balance, a required element of many such processes, may be achieved with multiple pumps or other proportioning or balancing devices which are to some extent independent of each other. This need may arise in treatments that involve
(Continued)

multiple fluids. Safe and secure mechanisms to ensure fluid balance in such systems are described.

17 Claims, 21 Drawing Sheets

Related U.S. Application Data continuation of application No. 17/097,724, filed on Nov. 13, 2020, now Pat. No. 11,406,744, which is a continuation of application No. 16/381,363, filed on Apr. 11, 2019, now Pat. No. 10,869,958, which is a continuation of application No. 15/517,928, filed as application No. PCT/US2015/055031 on Oct. 9, 2015, now Pat. No. 10,525,182.

(60) Provisional application No. 62/152,057, filed on Apr. 24, 2015, provisional application No. 62/062,764, filed on Oct. 10, 2014.

(51) Int. Cl.
*A61M 1/34* (2006.01)
*A61M 1/36* (2006.01)

(52) U.S. Cl.
CPC ........ *A61M 1/1615* (2014.02); *A61M 1/1647* (2014.02); *A61M 1/165* (2014.02); *A61M 1/34* (2013.01); *A61M 1/3403* (2014.02); *A61M 1/341* (2014.02); *A61M 1/3434* (2014.02); *A61M 1/3437* (2014.02); *A61M 1/3441* (2013.01); *A61M 1/3444* (2014.02); *A61M 1/3448* (2014.02); *A61M 1/3607* (2014.02); *A61M 1/3609* (2014.02); *A61M 1/3635* (2014.02); *A61M 2205/05* (2013.01); *A61M 2205/058* (2013.01); *A61M 2205/15* (2013.01); *A61M 2205/3331* (2013.01); *A61M 2205/3334* (2013.01); *A61M 2205/3341* (2013.01); *A61M 2205/3351* (2013.01); *A61M 2205/3355* (2013.01); *A61M 2205/3365* (2013.01); *A61M 2205/3368* (2013.01); *A61M 2205/502* (2013.01); *A61M 2205/702* (2013.01)

(56) References Cited

U.S. PATENT DOCUMENTS

| | | |
|---|---|---|
| 4,769,001 A | 9/1988 | Prince |
| 4,894,150 A | 1/1990 | Schurek et al. |
| 5,344,568 A | 9/1994 | Kitaevich et al. |
| 5,792,367 A | 8/1998 | Mattisson et al. |
| 5,836,908 A | 11/1998 | Beden et al. |
| 5,932,103 A | 8/1999 | Kenley et al. |
| 5,984,893 A | 11/1999 | Ward |
| 6,217,539 B1 | 4/2001 | Goldau |
| 6,221,672 B1 | 4/2001 | Baugh et al. |
| 6,284,131 B1 | 9/2001 | Hogard et al. |
| 7,112,273 B2 | 9/2006 | Weigel et al. |
| 7,341,568 B2 | 3/2008 | Zhang |
| 7,699,992 B2 | 4/2010 | Sternby |
| 7,727,222 B2 | 6/2010 | Silva et al. |
| 7,931,610 B2 | 4/2011 | Murakami et al. |
| 8,012,114 B2 | 9/2011 | Daniel et al. |
| 8,060,190 B2 | 11/2011 | Sörnmo et al. |
| 8,086,323 B2 | 12/2011 | Reghabi et al. |
| 8,092,414 B2 | 1/2012 | Schnell et al. |
| 8,182,692 B2 | 5/2012 | Gotch |
| 8,209,033 B2 | 6/2012 | Zhang et al. |
| 8,216,478 B2 | 7/2012 | Noack et al. |
| 8,239,010 B2 | 8/2012 | Banet et al. |
| 8,246,546 B2 | 8/2012 | Huiku |
| 8,246,567 B2 | 8/2012 | Bene |
| 8,287,739 B2 | 10/2012 | Barrett et al. |
| 8,361,006 B2 | 1/2013 | Kraemer |
| 8,524,154 B2 | 9/2013 | Shekalim et al. |
| 8,529,767 B2 | 9/2013 | Zhang |
| 8,583,226 B2 | 11/2013 | Moissl et al. |
| 8,591,865 B2 | 11/2013 | Wang et al. |
| 8,613,705 B2 | 12/2013 | Scheurer et al. |
| 8,632,485 B2 | 1/2014 | Schlaeper et al. |
| 8,663,931 B2 | 3/2014 | Saito et al. |
| 8,792,089 B2 | 7/2014 | Zhang et al. |
| 8,858,486 B2 | 10/2014 | Zhang et al. |
| 8,900,172 B2 | 12/2014 | Pohlmeier |
| 9,037,207 B2 | 5/2015 | Al-Ali et al. |
| 9,144,639 B2 | 9/2015 | Vantard et al. |
| 9,220,827 B2 | 12/2015 | Meibaum et al. |
| 9,278,171 B2 | 3/2016 | Brandl et al. |
| 9,381,289 B2 | 7/2016 | Hedmann et al. |
| 9,423,338 B2 | 8/2016 | Alic et al. |
| 9,566,377 B2 | 2/2017 | Jones et al. |
| 9,610,393 B2 | 4/2017 | Rada et al. |
| 9,724,455 B2 | 8/2017 | Kopperschmidt et al. |
| 9,743,843 B2 | 8/2017 | Chamney et al. |
| 9,795,739 B2 | 10/2017 | Al-Ali et al. |
| 9,814,412 B2 | 11/2017 | Zhang et al. |
| 9,943,633 B2 | 4/2018 | Sigg et al. |
| 9,968,298 B2 | 5/2018 | Heppe et al. |
| 9,980,663 B2 | 5/2018 | Wabel et al. |
| 9,987,406 B2 | 6/2018 | Wright et al. |
| 10,001,454 B2 | 6/2018 | Schick et al. |
| 10,010,289 B2 | 7/2018 | Gagel et al. |
| 10,016,549 B2 | 7/2018 | Stonger et al. |
| 10,092,249 B2 | 10/2018 | Kiani et al. |
| 10,117,590 B2 | 11/2018 | Barrett et al. |
| 10,155,077 B2 | 12/2018 | Maierhofer et al. |
| 10,328,192 B2 | 6/2019 | Jansson et al. |
| 2001/0016699 A1 | 8/2001 | Burbank et al. |
| 2003/0113933 A1 | 6/2003 | Jansson et al. |
| 2004/0245161 A1 | 12/2004 | Treu et al. |
| 2005/0113735 A1 | 5/2005 | Brugger et al. |
| 2005/0113757 A1 | 5/2005 | McFarlane |
| 2005/0126961 A1 | 6/2005 | Bissler et al. |
| 2005/0133735 A1 | 6/2005 | Tatsumi et al. |
| 2005/0251086 A1 | 11/2005 | Sternby |
| 2009/0076434 A1 | 3/2009 | Mischelevich et al. |
| 2009/0078622 A1 | 3/2009 | Zhang et al. |
| 2010/0016777 A1 | 1/2010 | Burbank et al. |
| 2010/0099958 A1 | 4/2010 | Kotanko et al. |
| 2010/0112583 A1 | 5/2010 | Ichiishi et al. |
| 2010/0137693 A1 | 6/2010 | Porras et al. |
| 2010/0192686 A1 | 8/2010 | Kamen et al. |
| 2010/0247377 A1 | 9/2010 | Tsutsumida et al. |
| 2010/0298751 A1 | 11/2010 | Schulte et al. |
| 2011/0000830 A1 | 1/2011 | Ikeda |
| 2011/0066043 A1 | 3/2011 | Banet et al. |
| 2011/0077474 A1 | 3/2011 | Huiku |
| 2011/0132838 A1 | 6/2011 | Curtis et al. |
| 2011/0208072 A1 | 8/2011 | Pfeiffer et al. |
| 2011/0230744 A1 | 9/2011 | Ripoll et al. |
| 2012/0118801 A1 | 5/2012 | Rada et al. |
| 2012/0150049 A1 | 6/2012 | Zielinski et al. |
| 2012/0181189 A1 | 7/2012 | Merchant |
| 2012/0203573 A1 | 8/2012 | Mayer et al. |
| 2012/0228226 A1 | 9/2012 | Castellarnau et al. |
| 2012/0232364 A1 | 9/2012 | Delmage |
| 2012/0310135 A1 | 12/2012 | Bauer et al. |
| 2012/0316465 A1 | 12/2012 | Maier et al. |
| 2013/0134077 A1 | 5/2013 | Wieskotten et al. |
| 2013/0153474 A1 | 6/2013 | Frorip et al. |
| 2013/0280104 A1 | 10/2013 | Heide et al. |
| 2014/0012097 A1 | 1/2014 | McCrea et al. |
| 2014/0224736 A1 | 8/2014 | Heide et al. |
| 2014/0299544 A1 | 10/2014 | Wilt et al. |
| 2015/0005699 A1 | 1/2015 | Burbank et al. |
| 2015/0100009 A1 | 4/2015 | Bearss |
| 2015/0133854 A1 | 5/2015 | Zhu et al. |
| 2015/0164370 A1 | 6/2015 | Wabel et al. |
| 2015/0258277 A1 | 9/2015 | Halpert et al. |
| 2015/0320363 A1 | 11/2015 | Haan |
| 2016/0058933 A1 | 3/2016 | Ballantyne et al. |

(56) References Cited

U.S. PATENT DOCUMENTS

| | | |
|---|---|---|
| 2016/0151554 A1 | 6/2016 | Jansson et al. |
| 2016/0166748 A1 | 6/2016 | Meyer et al. |
| 2016/0374596 A1 | 12/2016 | Barrett |
| 2016/0377530 A1 | 12/2016 | Barrett |
| 2017/0072125 A1 | 3/2017 | Wallenås et al. |
| 2017/0196517 A1 | 7/2017 | Zhang |
| 2017/0202493 A1 | 7/2017 | Bezemer |
| 2017/0224897 A1 | 8/2017 | Kopperschmidt et al. |
| 2017/0232174 A1 | 8/2017 | Gerlach et al. |
| 2017/0239409 A1 | 8/2017 | Reyes et al. |
| 2017/0258979 A1 | 9/2017 | Fulkerson et al. |
| 2017/0265793 A1 | 9/2017 | Maierhofer |
| 2017/0281849 A1 | 10/2017 | Goto et al. |
| 2017/0340801 A1 | 11/2017 | Roger et al. |
| 2017/0348471 A1 | 12/2017 | Goto et al. |
| 2018/0055988 A1 | 3/2018 | Brun |
| 2018/0140761 A1 | 5/2018 | Rovatti et al. |
| 2018/0169315 A1 | 6/2018 | Rovatti et al. |

FOREIGN PATENT DOCUMENTS

| | | |
|---|---|---|
| EP | 2279768 A1 | 2/2011 |
| EP | 2388030 B1 | 11/2011 |
| EP | 2558967 A1 | 2/2013 |
| EP | 2656785 A1 | 10/2013 |
| EP | 2678070 A2 | 1/2014 |
| EP | 2734111 A2 | 5/2014 |
| EP | 2735323 B1 | 5/2014 |
| EP | 2730302 B1 | 12/2014 |
| EP | 2836112 A1 | 2/2015 |
| EP | 2670454 B1 | 12/2015 |
| EP | 2578147 B1 | 4/2016 |
| EP | 3145393 A1 | 3/2017 |
| JP | 2004313522 A | 11/2004 |
| JP | 2008264217 A | 11/2008 |
| JP | 2009273749 A | 11/2009 |
| JP | 2009273750 A | 11/2009 |
| JP | 2009297403 A | 12/2009 |
| JP | 2009297404 A | 12/2009 |
| JP | 2009297405 A | 12/2009 |
| JP | 2010029434 A | 2/2010 |
| JP | 2011047767 A | 3/2011 |
| JP | 4905475 B2 | 3/2012 |
| JP | 5278681 B2 | 9/2013 |
| JP | 5280874 B2 | 9/2013 |
| JP | 5301259 B2 | 9/2013 |
| JP | 5385763 B2 | 1/2014 |
| JP | 5385764 B2 | 1/2014 |
| JP | 5548917 B2 | 7/2014 |
| JP | 2015029882 A | 2/2015 |
| JP | 2016214367 A | 12/2016 |
| WO | 2003028860 A1 | 4/2003 |
| WO | 2011130669 A1 | 10/2011 |
| WO | 2013010677 A2 | 1/2013 |
| WO | 2013152854 A1 | 10/2013 |
| WO | 2012116336 A3 | 2/2014 |
| WO | 2014090746 A1 | 6/2014 |
| WO | 2015007596 A1 | 1/2015 |
| WO | 2015179523 A1 | 11/2015 |
| WO | 2016057982 A1 | 4/2016 |
| WO | 2018017623 A1 | 1/2018 |

OTHER PUBLICATIONS

Extended European Search Report dated Feb. 3, 2020 for European Patent Application No. 17831728.5.
Extended European Search Report dated Jul. 19, 2019 for European Patent Application No. 19171893.1.
International Preliminary Report on Patentability for PCT/US2015/055031 dated Apr. 11, 2017, including the Written Opinion of the International Searching Authority dated Feb. 26, 2016.
International Search Report and Written Opinion for International Application No. PCT/US2015/055031 dated Feb. 26, 2016.
International Search Report and Written Opinion for International Patent Application No. PCT/US2017/042683 dated Dec. 7, 2017.
International Search Report and Written Opinion mailed Aug. 4, 2020 for International Patent Application No. PCT/US2020/034420.
International Search Report issued in corresponding PCT/US2017/042683, mailed on Dec. 7, 2017.
Japanese Office Action dated Aug. 20, 2019, issued in Japanese Patent Application No. 2019-502220.
Office Action (Communication Pursuant to Article 94(3) EPC) dated Mar. 13, 2019 for European Patent Application No. 15790326.1.
Office Action (Notice of Reasons for Refusal) mailed Mar. 8, 2022 for Japanese Patent Application No. 2021-007983.
Office Action (Notice of Reasons for Refusal) mailed Sep. 27, 2022 for Japanese Patent Application No. 2021-007983.
Office Action (Notice of Reasons for Rejection) mailed Feb. 18, 2020 for Japanese Patent Application No. 2019-502220.
Communication under Rule 71(3) EPC dated Mar. 18, 2022 for European Patent Application No. 19171893.1.
Extended European Search Report dated Jul. 8, 2022 for European Patent Application No. 22169775.8.
Office Action (Communication Pursuant to Article 94(3) EPC) dated Apr. 19, 2021 for European Patent Application No. 17831728.5.
Office Action (Decision of Rejection) mailed Sep. 24, 2020 for Japanese Patent Application No. 2019-502220.
Office Action (Examination Report under Section 18(3)) dated Apr. 17, 2019 for UK Patent Application No. 1902215.1.
Office Action (First Office Action) mailed Oct. 19, 2021 for Japanese Patent Application No. 2019-502220.
Office Action (Pre-Appeal Examination Report) mailed Mar. 30, 2021 for Japanese Patent Application No. 2019-502220.

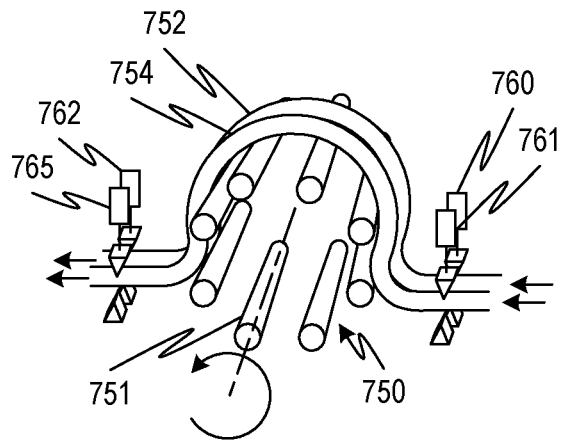
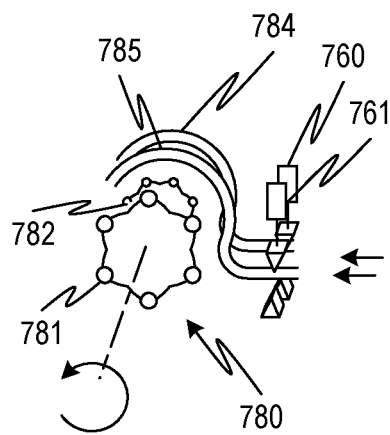
Fig. 12A　　　　　　　　　Fig. 12B
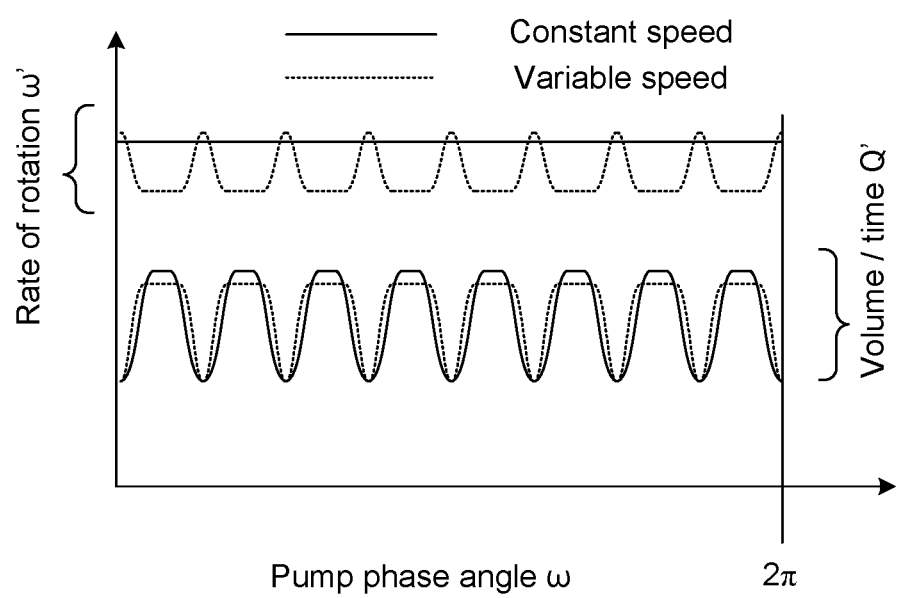
Fig. 13

FLOW BALANCING DEVICES, METHODS, AND SYSTEMS

CROSS-REFERENCE TO RELATED APPLICATIONS

This application is a Continuation of U.S. application Ser. No. 17/879,455, filed on Aug. 2, 2022, which is a Continuation of U.S. application Ser. No. 17/097,724, filed on Nov. 13, 2020, now U.S. Pat. No. 11,406,744, issued on Aug. 9, 2022, which is a Continuation of U.S. application Ser. No. 16/381,363, filed on Apr. 11, 2019, now U.S. Pat. No. 10,869,958, issued on Dec. 22, 2020, which is a Continuation of U.S. application Ser. No. 15/517,928, filed Apr. 7, 2017, now U.S. Pat. No. 10,525,182, issued on Jan. 7, 2020, which is a U.S. national stage filing under 35 U.S.C. § 371 of International Application No. PCT/US2015/055031 filed Oct. 9, 2015, which claims the benefit of U.S. Provisional Application Nos. 62/152,057 filed Apr. 24, 2015 and 62/062,764 filed Oct. 10, 2014, all of which are hereby incorporated by reference in their entireties.

STATEMENT OF GOVERNMENT SUPPORT

This invention was made with government support under HR0011-13-C-0023 awarded by Defense Advanced Research Projects Agency (DARPA). The government has certain rights in the invention.

BACKGROUND

A function of some extra corporeal blood treatment systems (ECBT systems), including hemodialysis, hemofiltration, hemodiafiltration, apheresis systems, etc., is the maintenance of the overall fluid balance between the fluid added to the patient and the fluid withdrawn from the patient. Ideally, this exchange will result in a net loss or gain of fluid to/from the patient that precisely matches the patient's treatment requirement. To achieve this, the ECBT may employ a volumetric fluid balancing system, of which a variety of different types are known. For example, see U.S. Pat. Nos. 5,836,908, 4,728,433, 5,344,568, 4,894,150, and 6,284,131, each of which is hereby incorporated by reference as if fully set forth in their entireties herein.

Fluid balancing mechanisms generally attempt to ensure that the total mass or volume of fluid pumped into, and removed from, the non-blood side of a filter or dialysis are equal. To provide for a desired differential between the net quantity removed/added, the inflow and outflow rates can be controlled to produce a net difference. This may be provided by regulating the rates of ingoing and outgoing pumps or by using a separate bypass, driven by a separate pump. In an example, such a bypass pump pumps at an ultrafiltration ("UF") line rate which is added to the balanced withdrawal rate.

Gravimetric systems that balance flow by weighing mass from a source and collected fluid from the treatment device and comparing the two are known. Another approach is to measure incremental volume transfer. Hard plumbed or disposable lined balance chambers alternately fill and empty in a manner that assures equal and opposite volume exchange. Systems using this approach are balancing a single inlet fluid flow with an effluent stream. A second stream of fluid is frequently added to the extracorporeal circuit using an additional pump, or external IV pump. The volume of this second stream may be balanced by the isolated ultrafiltration (UF) pump in an attempt to maintain patient fluid balance. This approach is limited by the calibration inaccuracies of the additional or external pump and the isolated UF pump. These inaccuracies are acceptable at low flow rates. However, at higher flow rates the cumulative volumetric inaccuracies may not achieve the desired patient volumetric balance. Additionally, this approach requires an operator to independently set the pump rates to achieve the desired balance.

SUMMARY

The disclosed subject matter described in this disclosure is an alternate approach to volumetric fluid balance using multiple pumps to control inflows and outflows from an extracorporeal circuit that have corresponding pump rates synchronized and calibrated relative to each other to assure balanced flow rates.

In certain systems, volumetric fluid balancing may be performed for a single therapy fluid stream using a system configuration including balance chambers, peristaltic pumps, and mechanically controlled pinch valves. The therapy fluid entering the blood path of the extracorporeal circuit may be balanced with effluent removed from the blood path through the dialyzer of the circuit so that the patient volume is not affected by this exchange of fluids. The limitation to a single therapy fluid inlet flow is a common limitation of various dialysis machines that use balance chambers. Some extracorporeal therapies can use more than one therapy fluid inlet flow that may be volumetrically controlled to achieve an overall patient fluid balance. For example, the difference between the total fluid that moves into the patient (for example, by flowing into the patient's blood stream) and that withdrawn from the patient must be precisely controlled. For example, in dialysis treatment, the amount of fluid entering the patient, for example through predilution, post-dilution, citrate infusion, and reverse ultrafiltration streams may be balanced against the net ultrafiltration stream to achieve a target net ultrafiltration rate. The subject matter described in this disclosure provides alternate machine configurations that support one or more therapy fluid flows synchronized with the effluent fluid flow from the extracorporeal circuit to achieve accurate fluid balance.

The disclosed subject matter includes several different system configurations that support one or more therapy fluid inlet flows balanced with the effluent flow by diverting each therapy flow pump individually using a valving/flow diversion means from their normal configuration during therapy and connecting the therapy fluid flow pump outlet in series with the effluent flow pump inlet with a pressure sensor between the therapy and effluent pumps. This calibration is achieved by synchronizing the pump flows and using the pressure sensor to synchronize the rates. A controller connected to the pressure sensor and pumps adjusts the effluent flow pump to the desired flow rate and the selected therapy fluid flow pump to achieve a desired pressure between the pumps and holds the pressure stable for a period of time to achieve a synchronization flow value for the therapy fluid pump. This can be repeated for multiple pressure values and stabilization times to achieve a synchronization curve for the therapy fluid flow pump versus pressure. Calibration may be performed at multiple flow rates as well to enhance the calibration algorithm. The therapy fluid flow pump is then diverted back to its normal therapy configuration. Additional therapy fluid flows can be calibrated one at a time with the effluent fluid flow in a similar manner, or, as discussed, therapy fluid flows can be combined and synchronized together.

Once calibrated, the pumps may operate at different speeds relative to each other to achieve the desired fluid balance outcome in the extracorporeal circuit (neutral, positive, or negative balance).

Additionally, the pump rates may be further compensated to account for transient effects such as changes in inlet/outlet pressures, changes due to pump life, and other factors. A compliant accumulator can be used to reduce pressure spikes and aid in achieving stable pressure control during the synchronization process. In the first configuration (FIGS. 2A-2D), a system is shown where fluid flows are controlled by multiple pumps that are synchronized and calibrated using a compliance chamber pressure sensor. Multiple inlet flows are capable of supplying one or more independent inlet fluids to the extracorporeal circuit. There is a single effluent pump that will operate at a rate equal to the sum of the combined inlet flows plus additional net ultrafiltration if desired.

Control valves are arranged so that the inlet flows can be diverted through a bypass fluid path either independently or in combination. Simultaneously, a control valve closes the flow of effluent from the filter so the effluent pump is fed by the bypass fluid path. The bypass fluid path has a pressure sensor and may have a small compliance chamber to measure pressure. The bypass fluid path can be defined by fluid channels that already form part of a circuit used for other purposes such as blood treatment or it can be predefined part of the circuit that is used exclusively for the purpose of connecting pumps to be synchronized. If the combined (coupled inlet and outflow pump flows) inflows match the outflow, the pressure will remain unchanged signaling that the pumps are synchronized and calibrated. If the pressure is either increasing or decreasing, the controller may increase or decrease pump rates to achieve balanced flow. The pressure at which the pumps are synchronized can be varied and the flow rates at which the pumps are synchronized can be varied, providing a comprehensive pump control algorithm. As disclosed flow measurement may be used for synchronization of pumps as well.

At the beginning of a treatment and periodically throughout the treatment, flows are diverted so that pump synchronization and calibration may be completed.

All pumps may be equipped with inlet and may also be fitted with outlet pressure sensors to support pressure compensation of the pump rate. That is, the flow rate of the pump may be derived from the pump rotation or reciprocation rate as adjusted by head pressure. This derivation and compensation may be done using a single function of both head pressure (inlet, outlet, or pressure change) and rotation speed. For example the function may be embodied in a look up table stored in a data store of a controller. Additionally, the control valves may be closed so that pump occlusion may be confirmed by the reading of the various pressure sensors.

The principles of the subject matter disclosed herein are applicable to both peristaltic pumps with disposable fluid pathways as well as hard plumbed systems and the various combinations of the two. In a hard plumbed configuration, the flow path components would require disinfection similar to standard dialysis machines and would require special techniques to meet the requirements for direct infusion of therapy fluids.

BRIEF DESCRIPTION OF THE DRAWINGS

FIGS. 12A and 12B show multiple line peristaltic pump configurations in which the flow in two lines are adjusted relative to each other by restricting flow into or out of the pumps by a control valve such that the flow can be matched, according to embodiments of the disclosed subject matter.

FIG. 13 shows properties of a peristaltic pump with a variable rotation rate, according to embodiments of the disclosed subject matter.

DETAILED DESCRIPTION

Figure 1A:
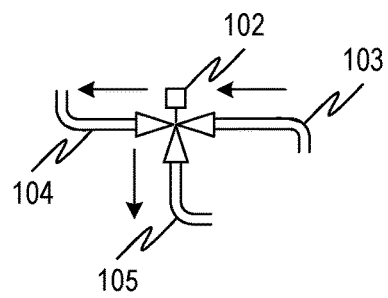
FIG. 1A shows a generic control valve that can flow fluid in to a selected fluid line, according to embodiments of the disclosed subject matter.
Figure 1B:
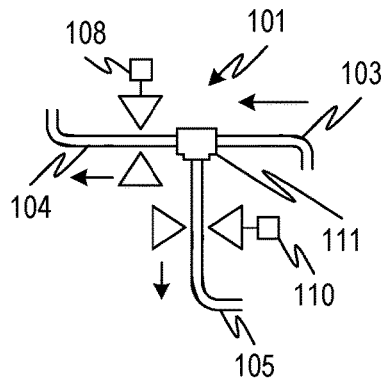
FIG. 1B shows a type of control valve that is beneficial in disposable circuits in which permanent clamping members open and control tubing branches by pinching, such that the tubing branches can be hermetically sealed and permanently connected by an inexpensive branch, according to embodiments of the disclosed subject matter.

FIG. 1A shows a generic control valve that can flow fluid into a selected fluid line. In the succeeding embodiments, the control valve 102 allows a flow from an inlet line 103 to be selectively transferred to either line 104 or 105 under control of a controller. At any point in the present disclosure such a control valve is symbolized as shown at 102 and may be embodied by any suitable multipath control valve including valves that employ pinching of flexible flow channels, rotating sealed selectors, etc. An advantageous type of control valve 102 is shown in FIG. 1B at 101. FIG. 1B shows a type of control valve that is beneficial in disposable circuits in which permanent clamping members open and control tubing branches by pinching, such that the tubing branches can be hermetically sealed and permanently connected by an inexpensive branch. Three lines 103, 104, and 105 are joined by a junction 111. Flow through lines 104 and 105 are permitted or restricted using control clamps 108 and 110. A controller can cause control clamp 108, for example a solenoid-retracted, spring driven pinching device, to be closed while opening control clamp 110 (of the same structure as control clamp 108) thereby selecting flow from line 103 through line 105. The controller can cause control clamp 108 to be open while closing control clamp 110 thereby selecting flow from line 103 through line 104. The lines 103, 104, and 105 may be flexible tubing. The junction 111 may be a Y-junction, T-junction, or any suitable member.

Figure 1C:
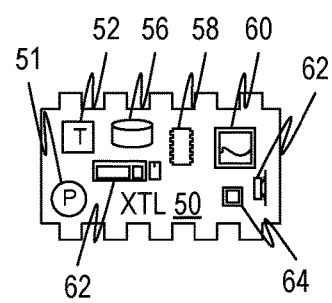
FIG. 1C illustrates a controller that may be present in all the embodiments described herein and assumed to be present in all descriptions of a controller, the figure showing elements connected to, or subsumed within one or more controllers that perform the one or more control or computational functions described in connection with the embodiments.

FIG. 1C illustrates a controller 50 that may be present in all the embodiments described herein and assumed to be present in all descriptions of a controller, the figure showing elements connected to, or subsumed within one or more controllers that perform the one or more control or computational functions described in connection with the embodiments. The controller 50 may have sensors 51, 52 such as pressure and/or temperature and/or flow rate and/or weight sensors. The controller may have data storage including non-volatile storage 56 and/or random access memory 58, flash or other data storage. A display 60, loudspeaker 62 and/or other user interface outputs may be connected or subsumed by the one or more controller represented by controller 50. User input devices such as a keyboard and mouse 62, touchscreen, gesture input, nerve-signal input, or other input device may be connected or subsumed.

Figure 2A:
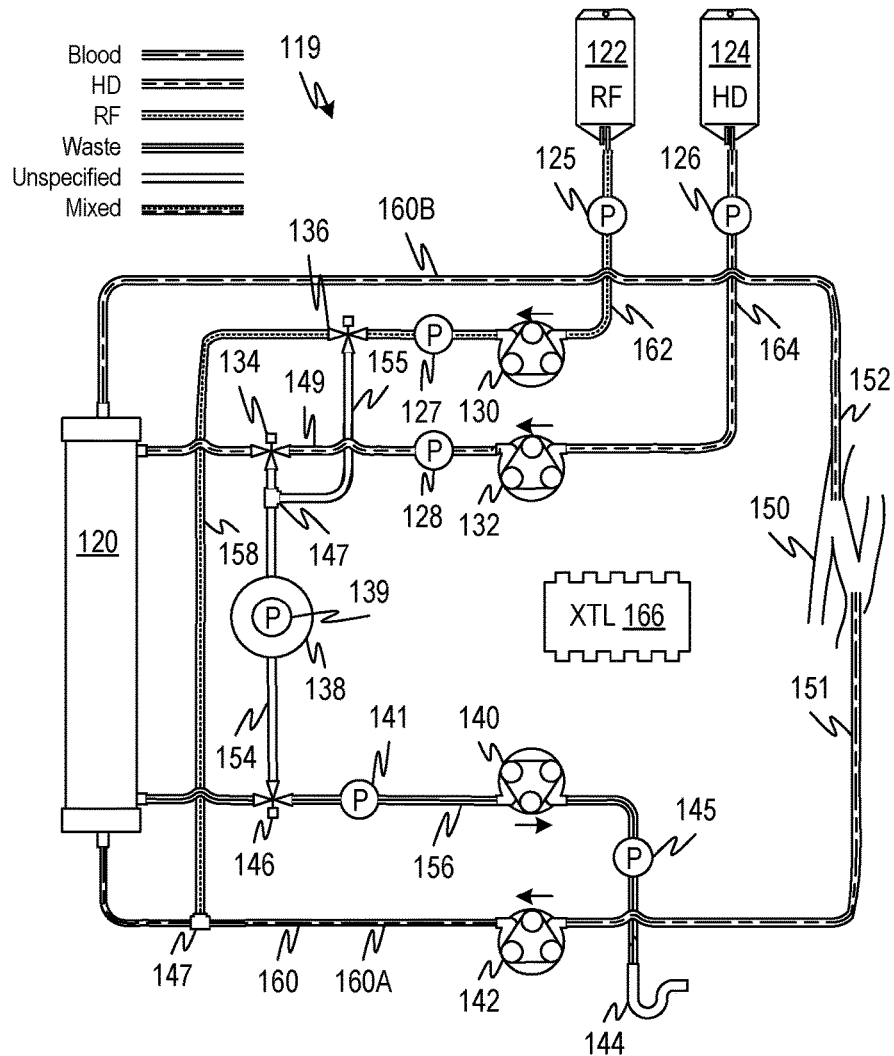
FIG. 2A is a schematic diagram of an extracorporeal blood treatment system, for example, a dialysis system in which an additional infusion stream is provided and balanced against an effluent stream, according to embodiments of the disclosed subject matter.

FIG. 2A is a schematic diagram of an extracorporeal blood treatment system 119, for example, a dialysis system in which an additional infusion stream is provided and balanced against an effluent stream. A blood circuit 160 has arterial line 160A and venous line 160B that transfer blood from a patient access 150 to a treatment device 120, here a dialyzer 120, and back to the patient access 150. The patient access 150 is illustrated by a fistula, which may be accessed by a dual lumen needle or by a pair of needles (not shown). Other types of accesses may be used to provide for a continuous flow of blood. Blood is pumped through the blood circuit 160 by a pump 142, for example a peristaltic pump 142. Fluid from a source of a first medicament 124, for example, dialysate 124 is pumped by a pump 132 into a dialysate compartment of the dialyzer 120 and spent dialysate is transferred out of the dialysate compartment of the dialyzer 120 by a pump 140 through line 156. The pumps 132 and 140 are controlled in such a fashion that a net fluid balance is maintained with a net positive or net negative ultrafiltration from the patient. This may be achieved by controlling the rate ratios of the pumps 132 and 140. An additional fluid may be supplied to the blood circuit 160 by pumping fluid from a fluid source 122 using a pump 130. The additional fluid from source 122 may be saline, blood-normal replacement fluid, citrate, or a medicament or drug. The additional mass or volume of fluid from the source 122 at the rate determined by the rate of pump 130 may be controlled such that the combined flow through pumps 130 and 132 is controlled against the rate of pump 140 such that the target net ultrafiltration rate is achieved. The rate of the pumps may be provided using an encoder on each pump which informs a controller 166 of the exact number of rotations per unit time of the pump (assuming the pumps are peristaltic pumps, but a corresponding method may be used for other types of pumps). Note that other pumping rate sensors are also possible, for example where stepper motor drives are used with the peristaltic pumps, the drive pulses may be counted to determine the speed of the pumps rather than an encoder. In the present embodiment, controller 166 may control the rates of all the pumps or a subset sufficient to provide the balance described.

Embodiments of the extracorporeal blood treatment system 119 may present the problem that the precision with which the rates of flow through the pumps 130, 132, and 140 can be controlled and/or measured is insufficient for the desired precision of fluid balance of the patient over the length of a predefined treatment. To allow for the regulation of the flow rates contributing to the balancing described, control valves 136, 134, 146 and pressure sensors 125, 126, 127, 128, 139, 141, and 145 may be provided. The pressure sensors 125, 126, 127, 128, 139, 141, and 145 may be of any suitable type including pressure pod type sensors that employ a strain gauge pressure sensor to produce an electrical signal that can be applied to the controller 166. The pressure sensors 125, 126, 127, 128, 139, 141, and 145 may also be of the type with an air trap chamber with an air line that leads to a pressure transducer. These sensors and control valves are connected to the controller 166 which receives the pressure signals from the pressure sensors and controls the flow of fluid through the control valves. Using the control valve 136, flow from the fluid line 162 can be selectively diverted by the controller 166 to the branch line 155 so that fluid from line 162 flows through the junction 147 into the branch line 154. Using the control valve 134, flow from the fluid line 162 can be selectively diverted by the controller 166 to the branch line 154 so that fluid from line section 149 flow through the junction 134 into the branch line 154. In a first position, the control valves 136 and 134 may divert flow from a selected one, or both, of the sources 124 and 122 through the branch line 154 through the control valve 146 and into the effluent line 156. A compliant flow accumulator 138 reduces the strength of pressure pulses to allow for a smoothly varying pressure signal from the pressure sensor 139. The accumulator may be a clear-walled rigid chamber with an air reservoir whose volume can be established by manually injecting air through a septum with a hypodermic needle to position a meniscus at a graduation marked on the chamber. The accumulator may also be a bladder with an urging mechanism such as spring which is positioned to resist the expansion of the bladder.

Figure 2B:
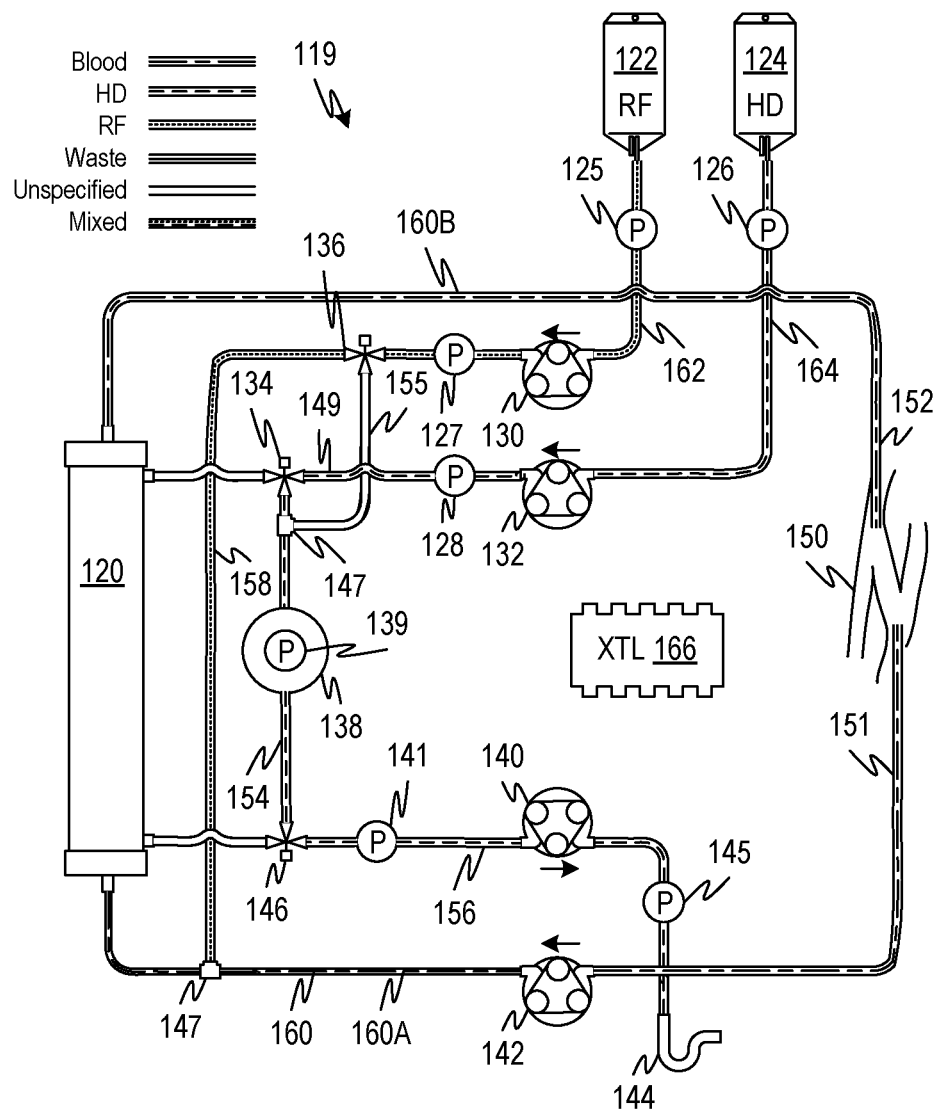
FIG. 2B is a schematic diagram of an extracorporeal blood treatment system as in FIG. 2A in a configuration in which flow from a first source is diverted directly through a branch line to the effluent output to permit the calibration, or confirmation of calibration of a pumping rate of fluid from the first source, to be obtained, according to embodiments of the disclosed subject matter.

FIG. 2B is a schematic diagram of an extracorporeal blood treatment system as in FIG. 2A in a configuration in which flow from a first source is diverted directly through a branch line to the effluent output to permit the calibration, or confirmation of calibration of a pumping rate for the fluid from the first source, to be obtained. In this configuration, the controller 166 causes the flow control valves 134 and 146 to divert flow from the source 124 to the branch line 154 and finally to the effluent line 156. The flow path so-defined uses two pumps with a closed circuit such that any difference in the flow rates of the pump 132 and the pump 140 will manifest a pressure change by the pressure sensor 139. The controller may perform a flow test in this configuration for a test interval to measure the degree to which the pump rates differ by calculating the rate of change of pressure indicated by the pressure sensor 139. In this mode, the controller 166 may step through a range of flow rates while sampling and storing pressure signals from pressure sensors 126, 128, 141, and 145, adjusting the speed of one of the pumps to reduce or eliminate the change in pressure of pressure sensor 139 (thereby matching the pumping rates), and storing the pressure differentials across each pump 132 and 140 that corresponding to the matched flow rates. This process may be performed before the beginning of each treatment after a fluid circuit has been changed, after a component has been changed such as a tubing segment, or after any other change in the system that could affect the flow performance.

In the previous, or other, embodiments, the configuration of FIG. 2B can be established briefly during a treatment merely to confirm a match, or a difference, between the pumping rates of the pumps 132 and 140. The system configuration of FIG. 2A can be modified by eliminating the fluid circuit for fluid from source 122 whereby the only balanced flow that needs to be maintained is from a single source 124. In such a system, the degree to which the flow rates of two independently-controlled pumps match can be tested momentarily, for example over a period of 2 seconds, by switching the control valves 134 and 146 to divert the flow and sampling the pressure signal from pressure sensor 139. In embodiments, the duration of the diversion may be long enough to establish a reliable indication to verify that the pumping rates are equal. The controller 166 may be further programmed to perform a correction of the rate of one of the pumps in order to more closely match the pumping rates of the two pumps. In an embodiment, the rate of rise or fall of the pressure indicated by the pressure sensor 139 is correlated with a correction based on a lookup table, stored in a memory accessible by the controller 166. The lookup table may correlate the rate of rise or fall and the absolute speed of one of the pumps and provide, for each pair, a correction of the speed of one of the pumps 132 and 140. In additional embodiments, a lookup table may store a function that correlates the pressure rise across a pump and an absolute speed that pump with a target pressure rise across the other pump that produces the same flow rate. The function is then corrected using the signal from pressure sensor 139 such that the pressure rises across the pumps, which can be measured continuously, can be used during treatment operation, to maintain a balanced flow. In another embodiment, the controller 166 may progressively change the rate or rates of pumping according to a negative feedback control algorithm to control the speed of one of the pumps 132 and 140 to reduce the pressure change indicated by the pressure sensor 139.

Figure 2C:
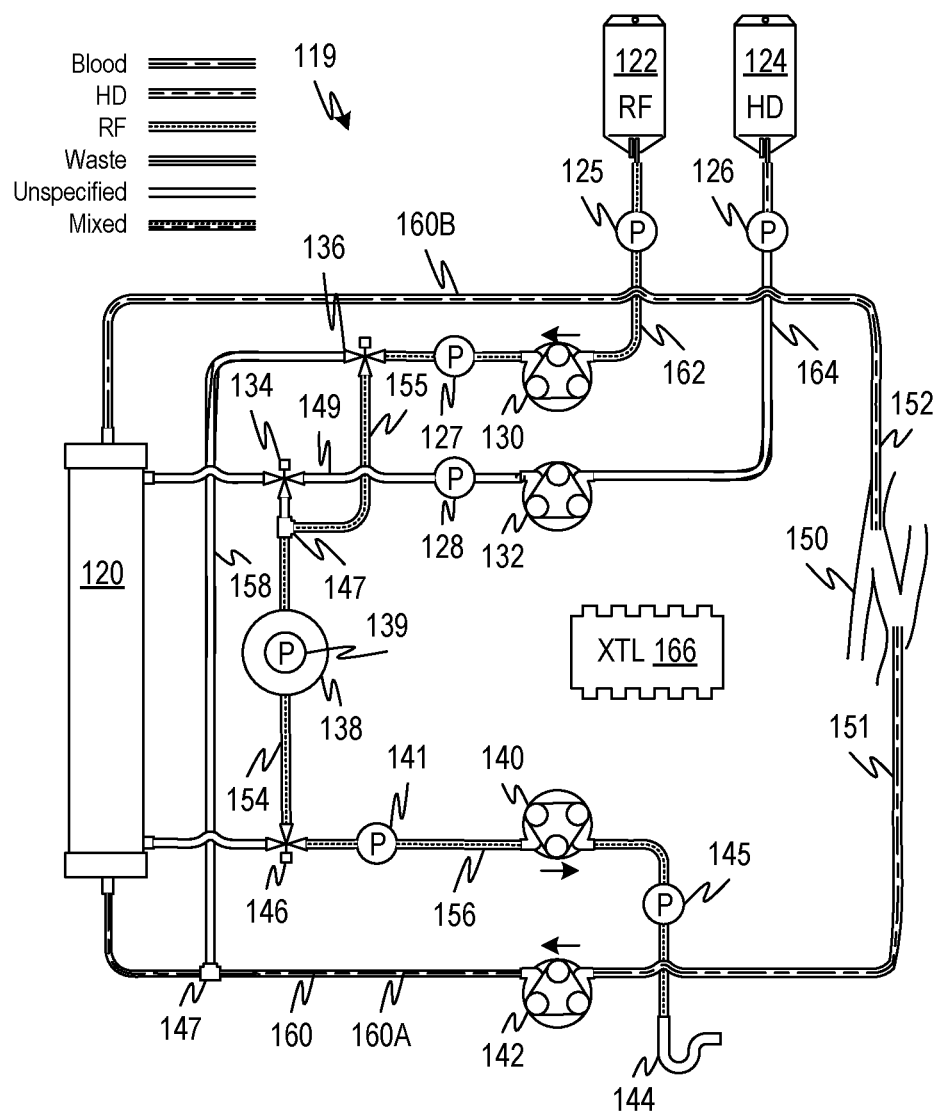
FIG. 2C is a schematic diagram of an extracorporeal blood treatment system as in FIG. 2A in a configuration in which flow from a second source is diverted directly through a branch line to the effluent output to permit the calibration, or confirmation of calibration of a pumping rate of fluid from the second source, to be obtained, according to embodiments of the disclosed subject matter.

FIG. 2C is a schematic diagram of an extracorporeal blood treatment system as in FIG. 2A in a configuration in which flow from a second source is diverted directly through a branch line to the effluent output to permit the calibration, or confirmation of calibration of a pumping rate of fluid from the second source, to be obtained. In this configuration, the controller 166 causes the flow control valves 136 and 146 to divert flow from the source 122 to the branch line 154 and finally to the effluent line 156. The flow path, so-defined, uses two pumps 130 and 140 in a closed circuit such that any difference in the flow rates of the pump 130 and the pump 140 will manifest a pressure change by the pressure sensor 139. The controller may perform a flow test in this configuration for a test interval to measure the degree to which the pump rates differ by calculating the rate of change of pressure indicated by the pressure sensor 139. In this mode, the controller 166 may step through a range of flow rates while sampling and storing pressure signals from pressure sensors 125, 127, 141, and 145, adjusting the speed of one of the pumps 130 and 140 to reduce or eliminate the change in pressure of pressure sensor 139 (thereby matching the pumping rates), and storing the pressure differentials across each pump 130 and 140 that correspond to the matched flow rates. This process may be performed before the beginning of each treatment after a fluid circuit has been changed, after a component has been changed such as a tubing segment, or after any other change in the system that could affect the flow performance.

In the previous, or other, embodiments, the configuration of FIG. 2C can be established briefly during a treatment merely to confirm that the match, or the difference, between the pumping rates of the pumps 132 and 140. The system configuration of FIG. 2A can be modified by eliminating the fluid circuit for fluid from source 122 whereby the only balanced flow that needs to be maintained is from a single source 124. In such a system, the degree to which the flow rates of two independently-controlled pumps match can be tested momentarily, for example over a period of 2 seconds, by switching the control valves 136, and 146 to divert the flow and sampling the pressure signal from pressure sensor 139. In embodiments, the duration of the diversion may be long enough to establish a reliable indication to verify that the pumping rates are equal. The controller 166 may be further programmed to perform a correction of the rate of one of the pumps in order to more closely match the pumping rates of the two pumps 130 and 140. In an embodiment, the rate of rise or fall of the pressure indicated by the pressure sensor 139 is correlated with a correction based on a lookup table, stored in a memory accessible by the controller 166. The lookup table may correlate the rate of rise or fall and the absolute speed of one of the pumps and provide, for each pair, a correction of the speed of one of the pumps 130 and 140. In additional embodiments, a lookup table may store a function that correlates the pressure rise across a pump and an absolute speed that pump with a target pressure rise across the other pump that produces the same flow rate. The function is then corrected using the signal from pressure sensor 139 such that the pressure rises across the pumps, which can be measured continuously, can be used during treatment operation, to maintain a balanced flow. In another embodiment, the controller 166 may progressively change the rate or rates of pumping according to a negative feedback control algorithm to control the speed of one of the pumps 132 and 140 to reduce the pressure change indicated by the pressure sensor 139.

Figure 2D:
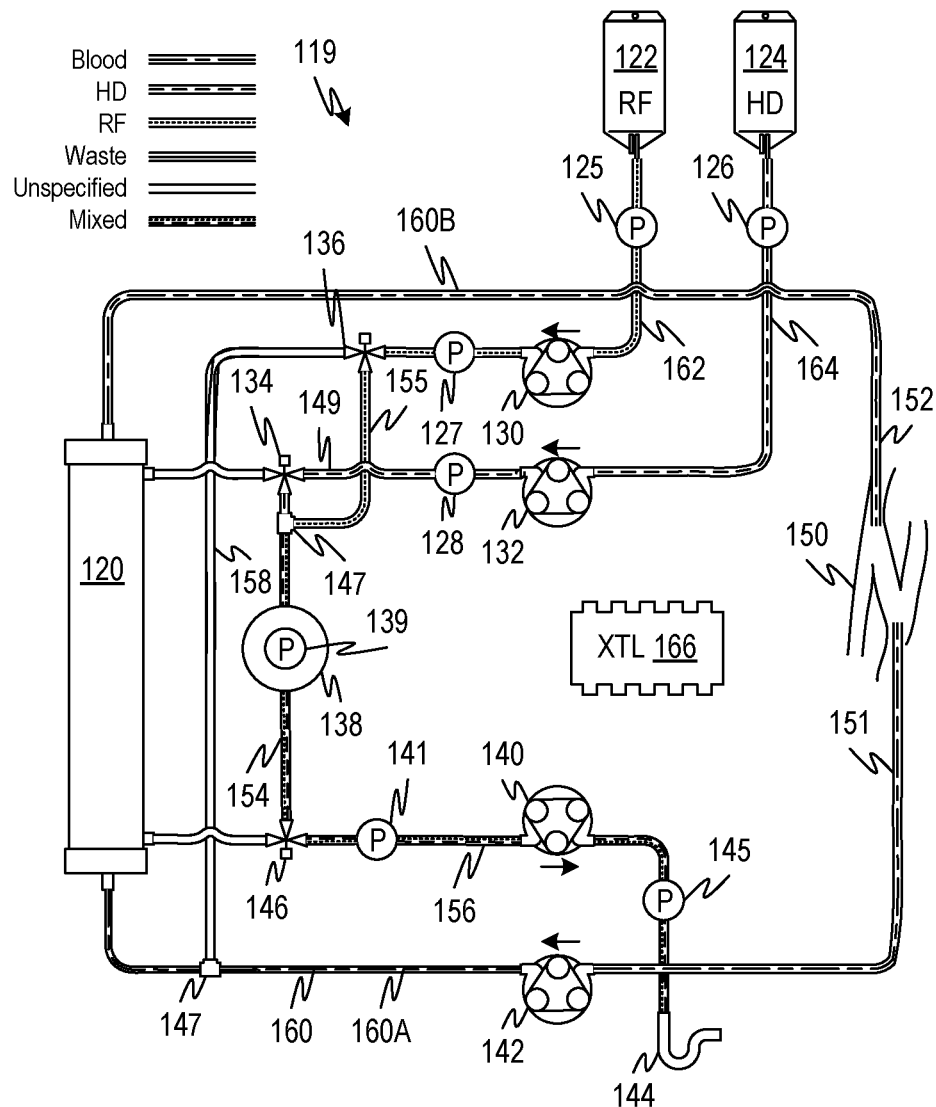
FIG. 2D is a schematic diagram of an extracorporeal blood treatment system as in FIG. 2A in a configuration in which flow from the first and second sources are diverted directly through branch lines to the effluent output to permit the calibration, or confirmation of calibration of a pumping rate for the combined fluids flow from the first and second sources, to be obtained, according to embodiments of the disclosed subject matter.

FIG. 2D is a schematic diagram of an extracorporeal blood treatment system as in FIG. 2A in a configuration in which flow from the first and second sources are diverted directly through branch lines to the effluent output to permit the calibration, or confirmation of calibration of a pumping rate for the combined fluids flow from the first and second sources, to be obtained. In this configuration, the controller 166 causes the flow control valves 134, 136, and 146 to divert flow from both the source 122 and the source 124 to the branch line 154 and finally to the effluent line 156. The flow path, so-defined, uses the two pumps 130 and 132 to push the flow and one pump 140 to pull the flow through the branch line 154 in a closed circuit such that any difference in the pushed and pulled flow rates will a cause a pressure change in the accumulator 138 indicated the pressure sensor 139. The controller may perform a flow test in this configuration for a test interval to measure the degree to which the pump rates differ by calculating the rate of change of pressure indicated by the pressure sensor 139. In this mode, the controller 166 may step through a range of flow rates while sampling and storing pressure signals from pressure sensors 125, 127, 126, 128, 141, and 145, adjusting the speed of one or two of the pumps 130 and 140 to reduce or eliminate the change in pressure of pressure sensor 139 (thereby matching the pumping rates), and storing the pressure differentials across each of the pumps 130, 132, and 140 that correspond to the matched flow rates. This process may be performed before the beginning of each treatment after a fluid circuit has been changed, after a component has been changed such as a tubing segment, or after any other change in the system that could affect the flow performance.

In the previous, or other, embodiments, the configuration of FIG. 2D can be established briefly during a treatment merely to confirm that the match, or the difference, between the combined pumping rates of the pumps 130 and 132 and the individual pump 140. The degree to which the flow rates of the independently-controlled pumps match can be tested momentarily, for example over a period of 2 seconds, by switching the control valves 134, 136, and 146 to divert the flow and sampling the pressure signal from pressure sensor 139. In embodiments, the duration of the diversion may be long enough to establish a reliable indication to verify that the combined pumping rate of pumps 130 and 132 is equal to that of pump 140. The controller 166 may be further programmed to perform a correction of the rate of one or two of the pumps in order to more closely match the push and pull pumping rates. In an embodiment, the rate of rise or fall of the pressure indicated by the pressure sensor 139 is correlated with a correction based on a lookup table, stored in a memory accessible by the controller 166. The lookup table may correlate the rate of rise or fall and the absolute speed of one of the pumps and provide, for each pair, a correction of the speed of one or two of the pumps 130, 132, and 140. In this and any of the foregoing embodiments, the speed of both push and pull pumps may be adjusted rather than a single one of the push and pull pumps. In additional embodiments, a lookup table may store a function that correlates the pressure rise across a pump and an absolute speed that pump with a target pressure rise across the other pump that produces the same flow rate. The function may then be corrected using the signal from pressure sensor 139 such that the pressure rises across the pumps, which can be measured continuously, can be used during treatment operation, to maintain a balanced flow. In another embodiment, the controller 166 may progressively change the rate or rates of pumping according to a negative feedback control algorithm to control the speed of one, two, or three of the pumps 130, 132 and 140 to reduce the pressure change indicated by the pressure sensor 139.

As explained, it is possible to control the fluid balance in the extracorporeal circuit by simply matching the cumulative pump rates of multiple inflows with the pump rate of the effluent outflow. In practice, it may be difficult to maintain pump rates with sufficient accuracy to achieve clinically effective fluid balance. As described above, switching in a push-pull arrangement of pumps whose flows are to be balanced, allows a pressure signal to indicate to a controller whether the pumping rates are equal and also, by sampling the pressure signal, the rate of change of the pressure of an accumulator can indicate the magnitude of the imbalance of pumping rates. Thus the change of pressure per unit time can be correlated to a magnitude of pumping speed difference based on the properties of the accumulator and the fluid circuit. This relationship may be experimentally determined and stored in a lookup table or a formula and used by the controller to adjust the speed of one or more of the push and pull pumps.

Although in the foregoing embodiments, pumps, pressure sensors, and flow control valves were described as separate elements, it is possible for composite devices to be employed which provide the same functionality in integrated devices in order to reduce the parts count. Further pumps of varying types may be used, including piston pumps, turbine pumps, and other types of pumps. Permanent and disposable circuits may also be employed to form the fluid circuits described above and below. In additional embodiments, instead of diverting flow to a branch of tubing and measuring a change in pressure due to differing flow rates of pushing and pulling pumps, it is possible to temporarily divert the flow to a gravimetric sensor which can measure a mass of fluid in a fixed period of time to provide a calibration against the pressure sensor which may then be used by the controller 166 to regulate the flow of fluid. Such a gravimetric device may use a self-emptying chamber attached to a self-zeroing scale.

Figure 3A:
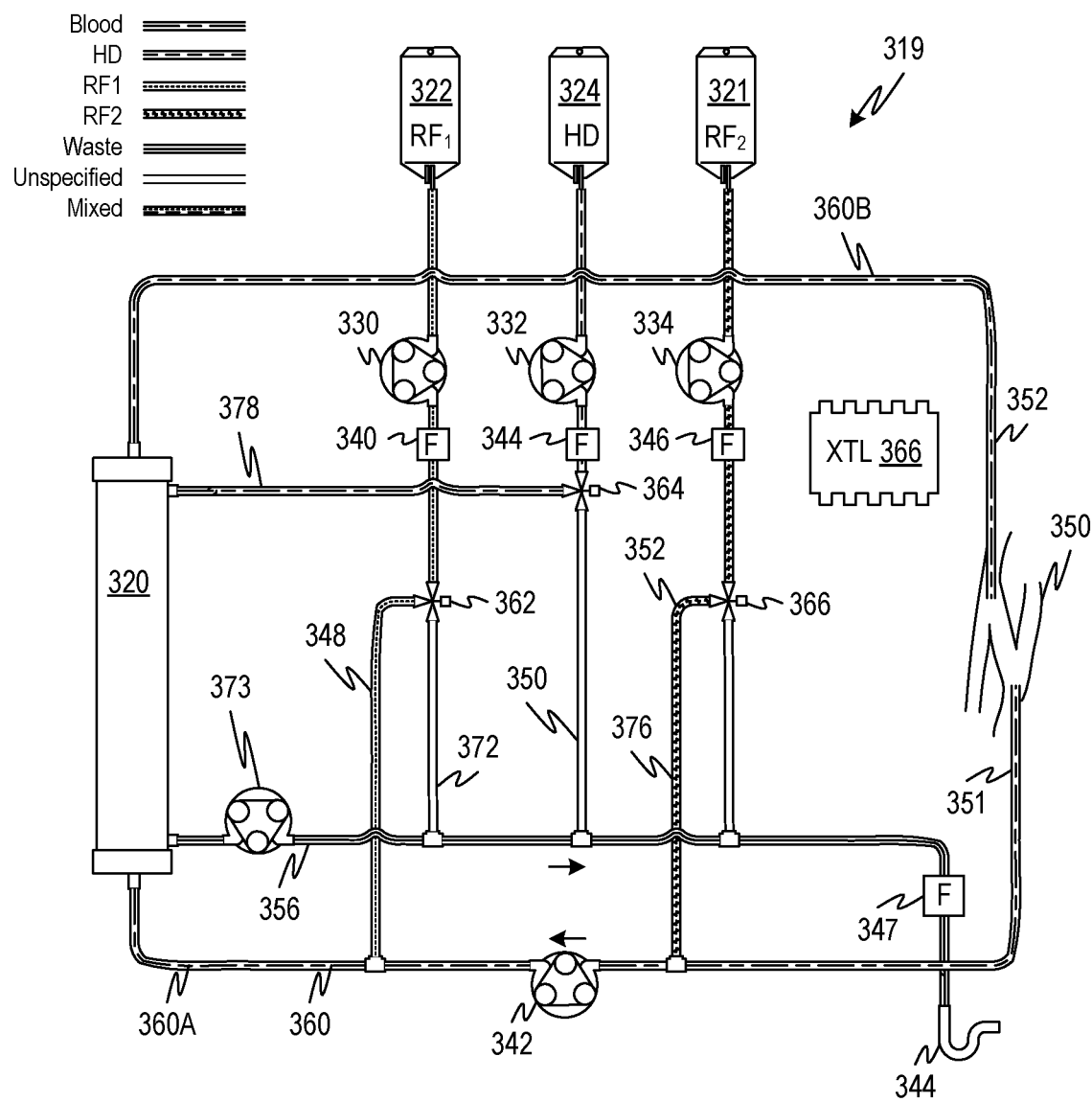
FIG. 3A is a schematic diagram of a further extracorporeal blood treatment system, for example, a dialysis system, in which multiple additional infusion streams are provided and balanced against an effluent stream, according to embodiments of the disclosed subject matter.

FIG. 3A is a schematic diagram of an extracorporeal blood treatment system 319, for example, a dialysis system in which two additional infusion streams are provided and balanced against an effluent stream. A blood circuit 360 has arterial line 360A and venous line 360B that transfer blood from a patient access 350 to a treatment device 320, here a dialyzer 320, and back to the patient access 350. The patient access 350 is illustrated by a fistula, which may be accessed by a dual lumen needle or by a pair of needles (not shown). Other types of accesses may be used to provide for a continuous flow of blood. Blood is pumped through the blood circuit 160 by a pump 342, for example a peristaltic pump 342. Fluid from a source of a first medicament 324, for example, dialysate 324 is pumped by a pump 332 into a dialysate compartment of the dialyzer 320 and spent dialysate is transferred out of the dialysate compartment of the dialyzer 320 by a pump 373 through line 356. The pumps 330, 332, 334, and 373 are controlled in such a fashion that a net fluid balance (of the patient including a target net ultrafiltration) is maintained. This may be achieved by controlling the rate ratios of the pumps 330, 332, 334, and 373. Note that pumps 330, 332, and 334 provide flow fluid into the system and their combined flow is balanced against the flow through the effluent pump 373. Here, fluids are exemplified by dialysate from a source 324 and two replacement fluids or medicaments RF1 and RF2, from respective sources 322 and 321. Here and elsewhere, the sources may be any source of fluid and may provide any type of fluid, although here they are illustrated using containers as examples. In the present or any of the embodiments, examples of types of medicaments include citrate, prediluent, replacement fluid, blood-normal replacement fluid or saline, any medicament or a drug.

The rate of the pumps may be indicated to the controller 366 by signals from an encoder in each pump 330, 332, 334, and 373 which informs a controller 166 of the exact number of rotations per unit time of the pump (assuming the pumps are peristaltic pumps, but a corresponding method may be used for other types of pumps). Note that other pumping rate sensors are also possible, for example where stepper motor drives are used with the peristaltic pumps, the drive pulses may be counted to determine the speed of the pumps rather than an encoder. In the present embodiment, controller 366 may control the rates of all the pumps or a subset sufficient to provide the balance described. For example, one of the pumps may run at a predefined rate that is not actively adjusted by the controller 366, for example, the effluent pump, and the others may be adjusted by the controller 366. In embodiments, all the pumps 330, 332, 334, and 373 are regulated by the controller.

As in the foregoing embodiments, embodiments of the extracorporeal blood treatment system 319 may present the problem that the precision with which the rates of flow through the pumps 330, 332, 334, and 373 can be controlled and/or measured is insufficient for the desired precision of fluid balance of the patient over the length of a predefined treatment. To allow for the regulation of the flow rates contributing to the balancing described, flow sensors 340, 344, 346, and 347 are provided. In embodiments, the flow sensor for each pump is used by the controller 366 to regulate the balance based on a stored ultrafiltration rate or total ultrafiltrate volume (mass) to be removed in a treatment. The net fluid withdrawal or infusion can be controlled by suitable regulation of the flow rate and numerical accumulation of volume or mass ultrafiltered from (infused into; i.e., negative ultrafiltered from) the patient. The rate or total amount of each medicament from sources 321, 322, and 324 can be regulated accordingly. During normal operation the flow configuration of FIG. 3A may be used whereby the fluids from the three sources 321, 322, and 324 are pumped, by pumps 330, 332, 334, into the blood line 360A and the treatment device 320, respectively and effluent fluid is drawn from the treatment device 320 by pump 373. In variations of the system a greater or smaller number of fluids are used.

To calibrate or confirm the calibration of flow sensor 340, the control valve 362 may be set to establish a flow of fluid from source 322 directly into the effluent line 356 where the flow is additional measured by flow sensor 347. Since flow sensor 347 is in an effluent line, it may be based on a permanent flow measurement system with high accuracy that need not provide for a sterile flow path. For example, a high accuracy flow meter of a positive displacement type with pistons and a crank connected to an encoder may be used. High precision transit-time flow meters may also be used, which may label the effluent fluid using a thermal label without concern about rendering it physiologically incompatible or denatured in any way. Other examples in include turbine meters, vortex shedding flow meters, and dynamic gravimetric mass flow meters. In the embodiment 319, control valves 362, 364, and 366 permit the flow from each source 321, 322, and 324 to be individually or collectively conveyed directly to the drain line 356 and thereby through the flow sensor 347. In embodiments, the flow sensor 347 is of a higher accuracy than the flow sensors 340, 344, and 346. By flowing from each source 321, 322, and 324 individually or collectively through a respective one of the flow sensors 340, 344, and 346 and conveying the fluid directly to the drain line 356 and thereby through the flow sensor 347, the flow sensors 340, 344, and 346 may be individually or collectively verified or calibrated based upon a more accurate flow given by flow sensor 347. In embodiments, the flow sensor 347 is based on a standard traceable measurement mechanism, such as National Institute of Standards and Technology. In embodiments, the flow sensor 347 provides a direct measurement of volume or mass and the flow sensors 340, 344, and 346 indicate flow by measuring a quantity that is indirectly connected with volume or mass such as pressure loss in a flow restriction, a parameter associated with flow velocity such as time of flight of a fluid label, a turbine speed, etc.

Figure 3B:
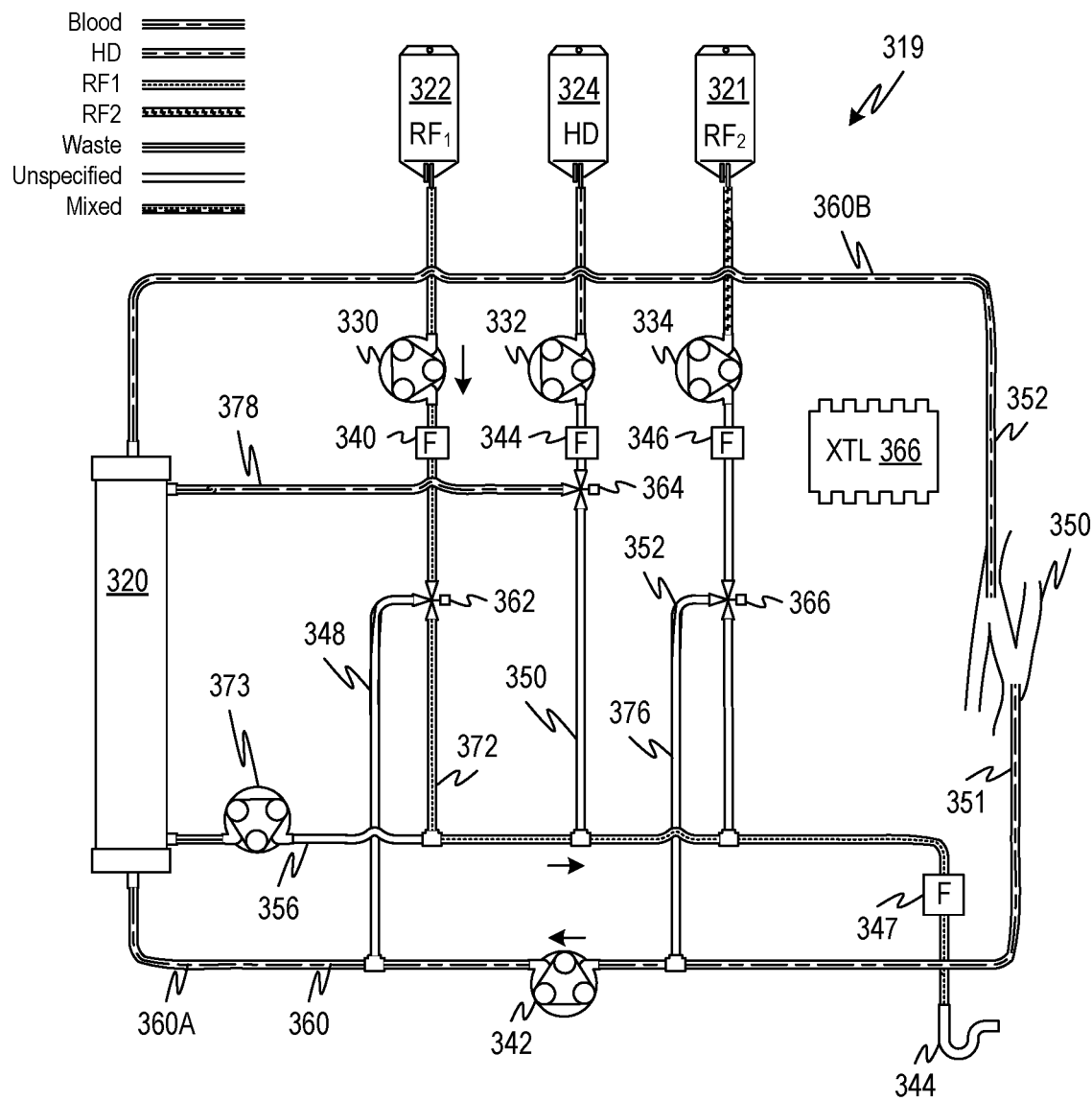
FIG. 3B is a schematic diagram of the extracorporeal blood treatment system of FIG. 3A, in a configuration in which a flow is established to permit a controller to compare the indication of a flow sensor of a selected ingoing stream to that of a flow sensor of an effluent stream, according to embodiments of the disclosed subject matter.
Figure 3C:
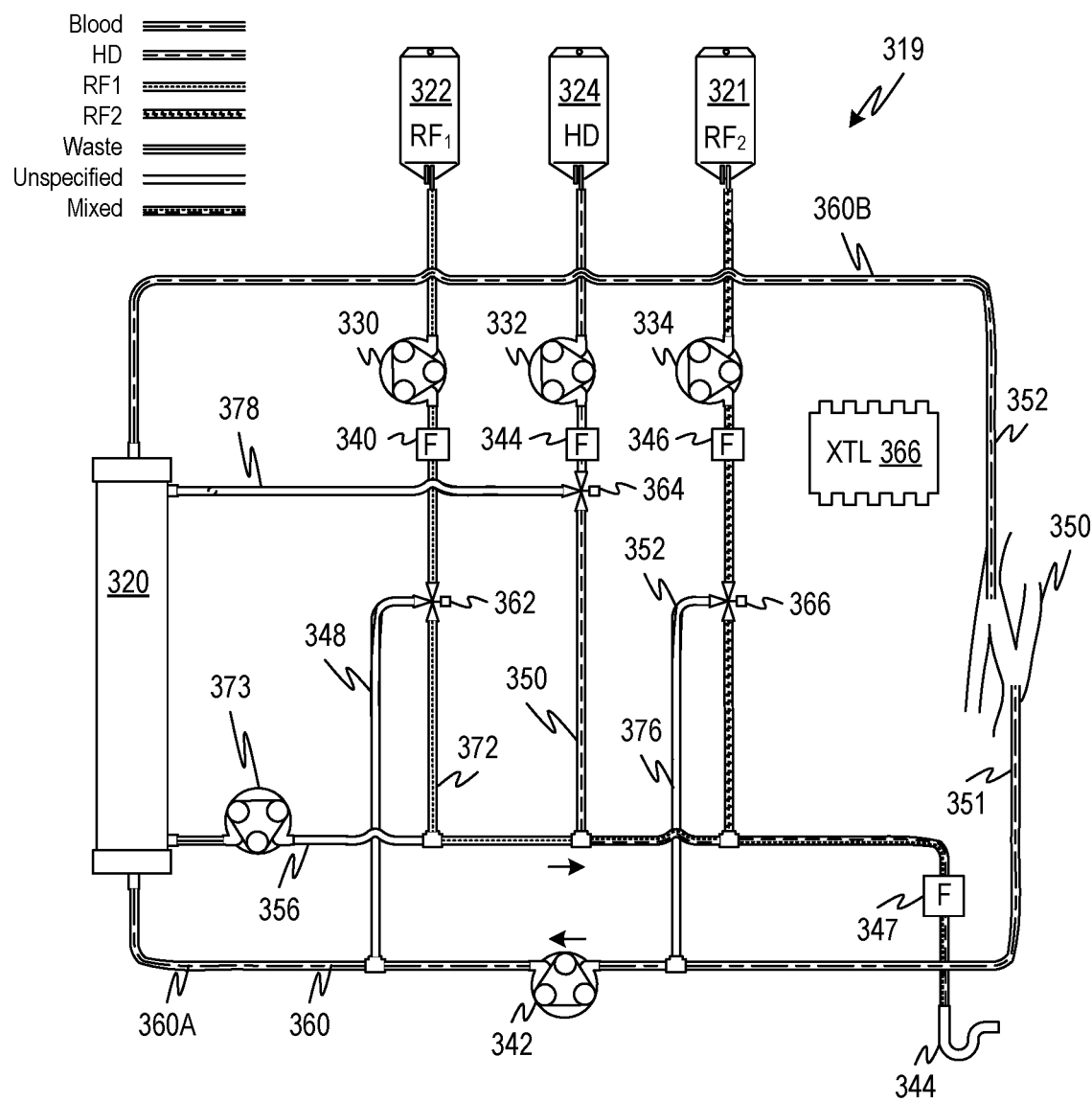
FIG. 3C is a schematic diagram of the extracorporeal blood treatment system of FIG. 3A, in a configuration in which a flow is established to permit a controller to compare the indication of multiple flow sensors of multiple ingoing streams to that of a flow sensor of an effluent stream, according to embodiments of the disclosed subject matter.

In embodiments, at the start of a treatment, fluid from each source 321, 322, and 324 is individually conveyed through a respective one of the flow sensors 340, 344, and 346 and further conveyed through the drain line 356 and thereby through the flow sensor 347. The controller 366 configures the control valves 362, 364, and 366 so as to establish each flow so that each of the flow sensors 340, 344, and 346 is individually, in turn, connected by a fixed flow path with the flow sensor 347. An example configuration is shown in FIG. 3B where the fluid from source 322 (RF1) is diverted to the drain line 356 and only the pump 330 is operated so that there is a direct flow path through the flow sensor 340, to be calibrated or checked, and the true flow sensor 347 and out to a drain 344. The other flow sensors 332 and 334 would have corresponding configurations and pump operations. Note that the effluent pump 373 is not operated during these individual calibrations. For each configuration, a range of flow rates may be established and a correction factor recorded by the controller, based on the difference between the true flow rate given by flow sensor 347 and the flow rate indicated by the respective one of the flow sensors 340, 344, and 346. The set of corrections provides calibration data to allow a more correct flow rate indication by each of the flow sensors 340, 344, and 346 during a treatment. In further embodiments, each of the flow sensors 340, 344, and 346 is connected in turn during treatment for a brief time to confirm the accuracy of its respective flow rate indication to the controller 366. During each such test, a calibration adjustment may be stored by the controller 366 and used to correct the later flow rate indication of the tested one of the flow sensors 340, 344, and 346. Further, the controller may back-correct the net fluid volume transfers to or from the patient based on the error indicated by such tests. In response to the magnitude of the error, the controller 366 may modify the net fluid transfer to or from the patient by adjusting the commanded ultrafiltration rate or the rate of flow of replacement fluid to the patient. The controller 366 may also command the injection of a bolus of replacement fluid after or during the treatment. The controller 366 may output an indication on a user interface of a recommended net change in ultrafiltration or bolus injection to permit an operator to override. The output may show the magnitude of the error and the correction. The error may be stored in a treatment log or machine performance log or both. In an example, a total cumulative volume reverse ultrafiltered to the patient (i.e. infused) may be reduced by an interpolated calibration factor retroactively applied between two calibration intervals during a treatment. The controller 366 may store the historical flow data and apply the corrected calibration factor to the historical data to arrive thereby at a correct cumulative reverse ultrafiltered volume (i.e., volume infused) to the patient. The pump rates may then be adjusted by the controller responsively to a remaining treatment time to arrive at a target net ultrafiltration volume.

Figure 4A:
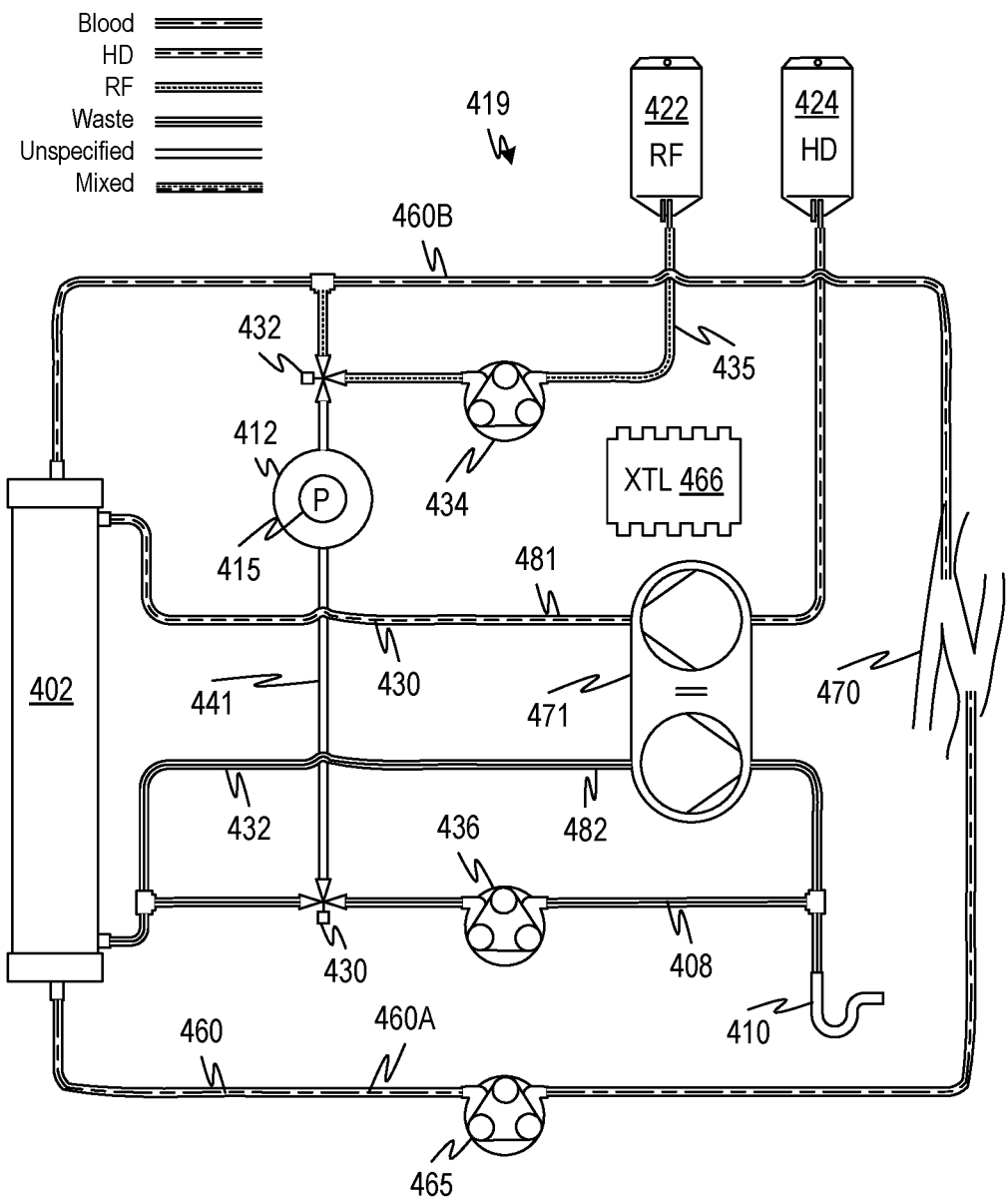
FIG. 4A shows a volumetric balancing system of an extracorporeal blood treatment system with a secondary flow that is selectively connectable in a push pull relationship with an ultrafiltration branch of the balancing system, according to embodiments of the disclosed subject matter.

FIG. 4A shows a volumetric balancing system of an extracorporeal blood treatment system with a secondary flow that is selectively connectable in a push pull relationship with an ultrafiltration branch of the balancing system, according to embodiments of the disclosed subject matter. In extracorporeal blood treatment system 419, for example, a dialysis system balances a dialysis stream and an additional infusion stream. A blood circuit 460 has arterial line 460A and venous line 460B that transfer blood from a patient access 470 to a treatment device 402, here a dialyzer 402, and back to the patient access 470. The patient access 470 is illustrated by a fistula, which may be accessed by a dual lumen needle or by a pair of needles (not shown). Other types of accesses may be used to provide for a continuous flow of blood. Fluid from a source 424 of a first medicament, for example, dialysate is pumped by a volumetric balancing mechanism 471 into a dialysate compartment of the dialyzer 402 and spent dialysate is transferred out of the dialysate compartment of the dialyzer 402 through line 432. An infusion stream flows medicament or drug or any other fluid from a source 422 to the venous line 460B via pump 434. Although one infusion stream from source 422 is illustrated, any number of infusion streams may be added to form variations of the present embodiment. The volumetric balancing mechanism 471, which may be, for example, any type that volumetrically balances (provides equal flow volumes) of the flows in ingoing 481 and outgoing 482 streams, balances the flow of dialysate from source 424 flowing in line 430 against the flow of spent dialysate in line 432. During a treatment, blood is pumped through the blood circuit 460 by a pump 465, for example a peristaltic pump 465. During treatment, fluid flows from source 422 into a venous blood line 460B, from source 422, through a control valve 432, pumped by pump 434. Although the flow of fluid from source 422 is shown being added to the venous blood line 460B, in other embodiments, the fluid is conveyed to the arterial blood line 460A using suitable connections. A net ultrafiltrate volume is controlled by an additional effluent stream that is pumped by pump 436 through ultrafiltrate bypass line 408, which joins the balanced spent dialysate flow in line 432 and exits the drain 410. A controller 466 controls the pump 434 and may control the pump 436. To balance the flow of fluid from source 422, the ultrafiltrate bypass flow may be increased to include both a target ultrafiltrate and a new flow of fluid from the source 422. Thus, the volume flowing through line 408 during treatment would be the total of the flow from the source 422 through line 435 plus the rate corresponding to the target ultrafiltrate.

Figure 4B:
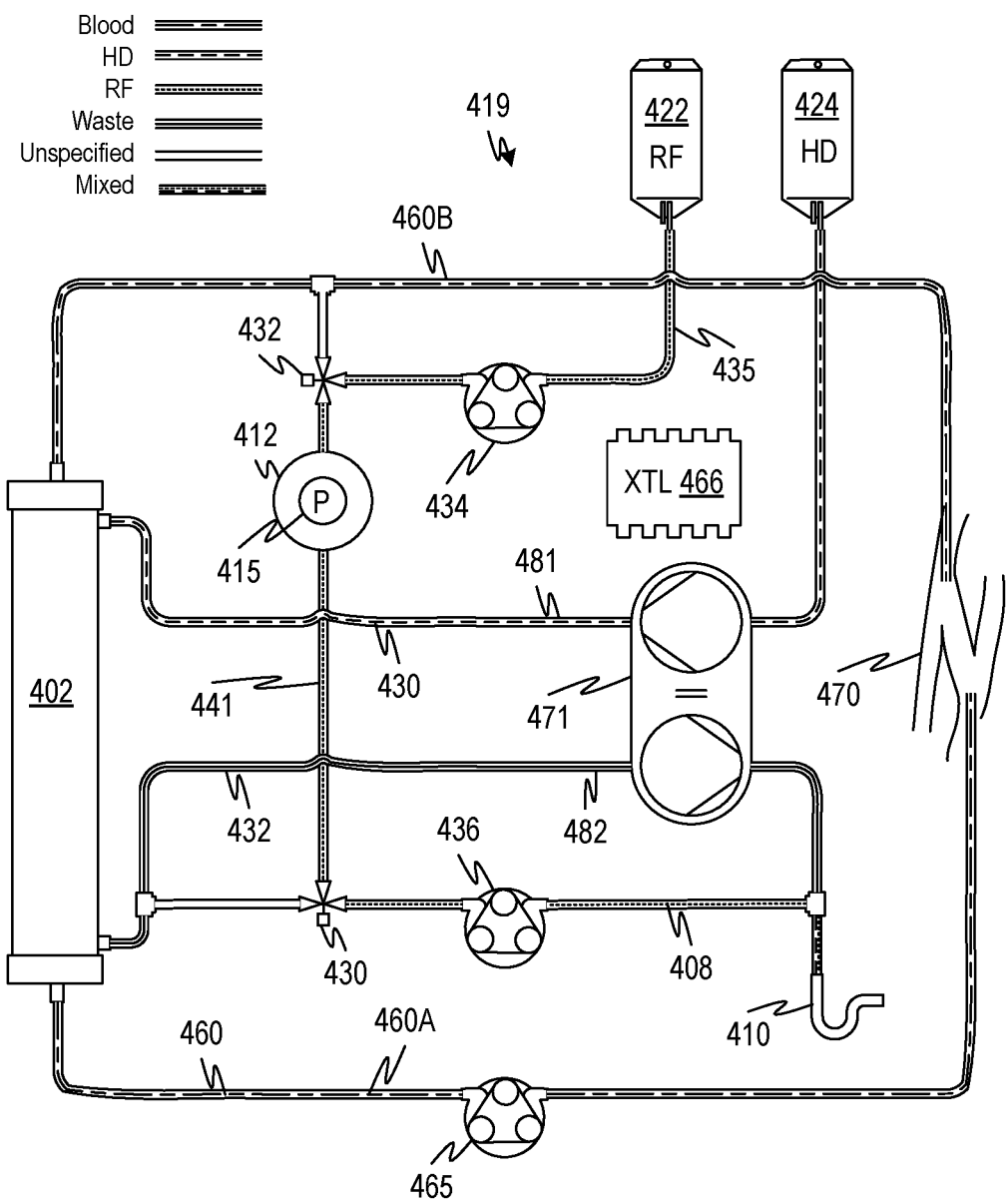
FIG. 4B shows a volumetric balancing system of an extracorporeal blood treatment system with a secondary flow that is selectively connectable in a push pull relationship with an ultrafiltration branch of the balancing system, where flow through the secondary line is connected in push pull relationship to the flow in the ultrafiltration branch in order to compare the pumping rates, according to embodiments of the disclosed subject matter.

FIG. 4B shows a volumetric balancing system of an extracorporeal blood treatment system with a secondary flow that is selectively connectable in a push pull relationship with an ultrafiltration branch of the balancing system, where flow through the secondary line is connected in push pull relationship to the flow in the ultrafiltration branch in order to compare the pumping rates, according to embodiments of the disclosed subject matter. At a time of calibration (illustrated in FIG. 4B), the rate of pumping of pump 436 and of pump 434 can be controlled by controller 466 to be equal while the pumps are placed, temporarily, in a push-pull relationship by diverting all flow in line 435 to the branch line 441 and into line 408 such that a pressure change in an accumulator 412 will be indicated by a pressure sensor 415 connected to the accumulator whose signal is applied to the controller 466. The control parameters used to determine the flows in pumps 434 and 436 may be adjusted to compensate the fluid balance error for multiple different flow rates thereby permitting a balance calibration. Note this calibration does not permit an error in absolute flow rates to be compensated but rather merely an error in the flow balance between the commanded rate of pump 436 and that of pump 434. The push-pull flow is established by controlling control valves 432 and 430. The calibration procedure can be performed during a treatment or prior to each treatment. The calibration process may be preceded by a verification procedure which indicates whether the commanded flows are balanced (by a pressure change in the accumulator 412 indicated by pressure sensor 415). If the verification procedure indicates that the flows are balanced, the calibration may be skipped. The verification procedure may be performed for a smaller number of flow rates than a calibration procedure.

Here, fluids are exemplified by dialysate from a source 424 and a replacement fluid or medicaments RF from source 422. Here and elsewhere, the sources may be any source of fluid and may provide any type of fluid, although here they are illustrated using containers as examples. In the present or any of the embodiments, examples of types of medicaments are citrate, prediluent, replacement fluid, blood-normal replacement fluid or saline, any medicament or a drug. The rate of the pumps may be indicated to the controller 466 by signals from an encoder in each pump which informs the controller 466 of the exact number of rotations per unit time of the pump (assuming the pumps are peristaltic pumps, but a corresponding method may be used for other types of pumps). Note that other pumping rate sensors are also possible, for example where stepper motor drives are used with the peristaltic pumps, the drive pulses may be counted to determine the speed of the pumps rather than an encoder. The accumulator 412 and pressure sensor 415 may be as discussed with reference to the corresponding element of earlier embodiments. The volumetric balancing mechanism 471 may be as described in U.S. Pat. No. 7,112,273 to Weigel et al. The volumetric balancing mechanism 471 may be replaced by any type of flow balancing system including ones that use scales to weigh the cumulative total of fresh and spent fluids.

Figure 5A:
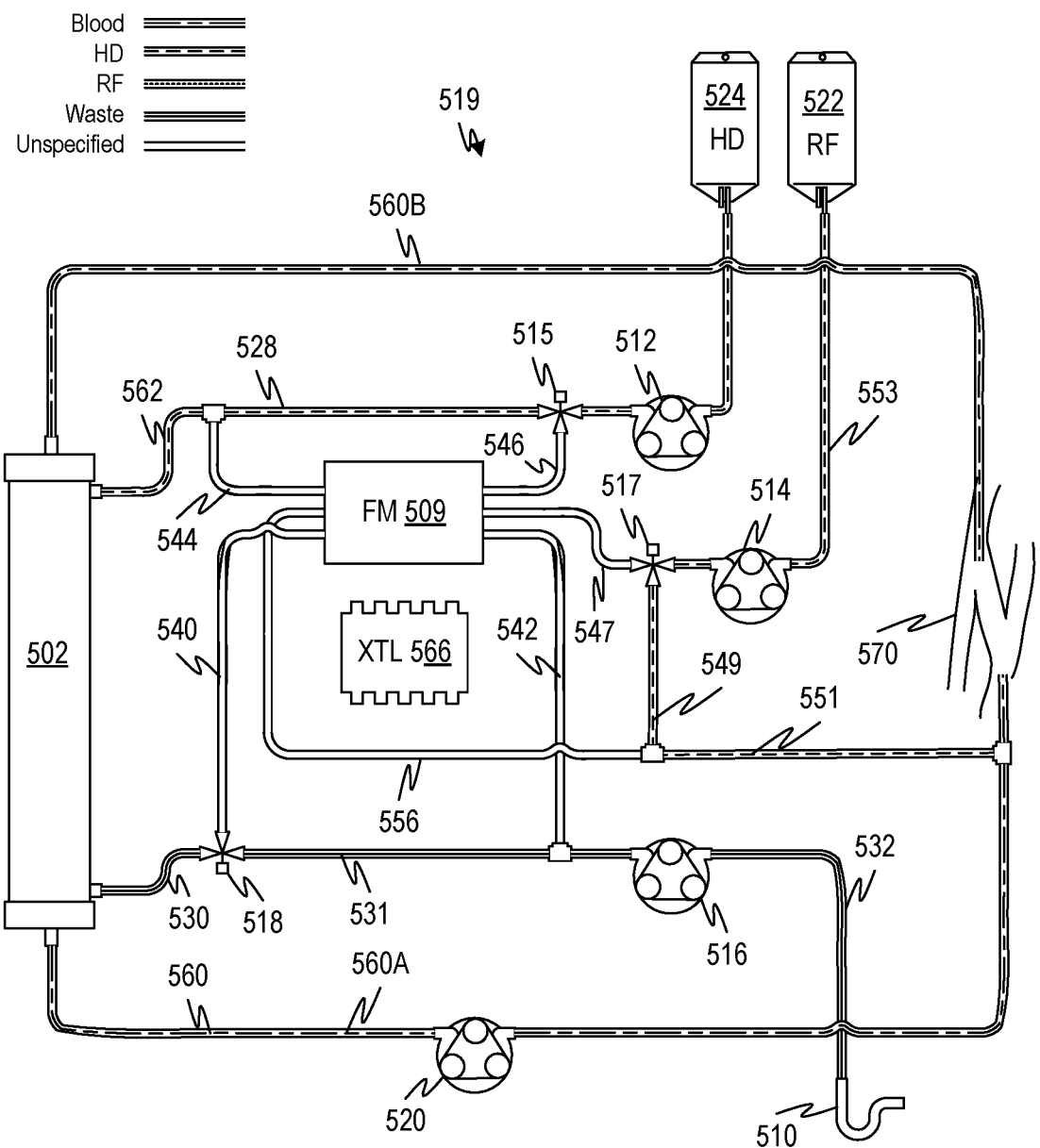
FIG. 5A shows a further pumping system which may be used for balancing multiple fluids under control of a controller and which is automatically selectively configurable to permit calibration of pumps respective to each fluid to permit higher accuracy of fluid balancing, according to embodiments of the disclosed subject matter.
Figure 5B:
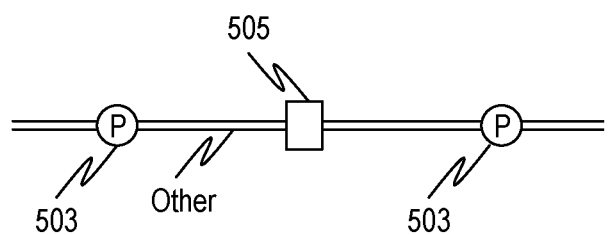
FIG. 5B shows an embodiment of a flow sensor that may be used in place of any of the flow sensors of the embodiments disclosed herein.

FIG. 5A shows a further pumping system which may be used for balancing multiple fluids under control of a controller and which is automatically selectively configurable to permit calibration of pumps respective to each fluid to permit higher accuracy of fluid balancing, according to embodiments of the disclosed subject matter. Independent pumps 512, 514, 516, and 520 flow fluids from source 524 (which may be dialysate or other medicament, for example), fluid from source 522, which may be a medicament, and effluent fluid from a blood treatment device 502 (e.g., a dialyzer) at rates dependent command signals from a controller 566. In an embodiment, dialysate circulates from source 524 though the pump 512 through line 528 and line 562 into a dialysate compartment of a dialyzer 502. Spent dialysate flows from the dialysate compartment of the dialyzer 502 through lines 530 and 531 pump 516 and to a drain 510 through line 532. Blood is circulated through the blood compartment of the dialyzer 502 by a blood circuit 560 which has an arterial line 560A and a venous line 560B. Replacement fluid flows from source 522 through line 553, pump 514, and lines 549, and 551 into the arterial line 560A. The pumps 512, 514, and 516 are controlled in a manner that allows the combination of ingoing fluids (fluids from sources 522, 524 flowing at rates of pumps 512 and 514) to be balanced against the flow of effluent pumped by pump 516. Any of the fluids can be selectively pumped through a flow sensor 509 using control valves 515, 517, and 518. FIG. 5B shows an embodiment of a flow sensor that may be included in flow sensor 509. A fluid flows through a line 507 through a flow restriction 505. The fluid pressure on either side of the restriction indicates the flow rate. Pressure sensors 503 indicate the pressure on either side and are connected to the controller 566 which may convert the pressure signals to a flow rate by means of a calibration data table or formula stored in the controller 566. Other types of flow sensors 509 can also be used. The flow restriction 505 may be a length of tubing of a precise inner diameter of non-compliant material and with a coefficient of thermal expansion. Instead of a low coefficient of thermal expansion, the length of tubing may be temperature controlled during calibration or by compensating for size changes due to temperature numerically during the calibration procedure.

Figure 5C:
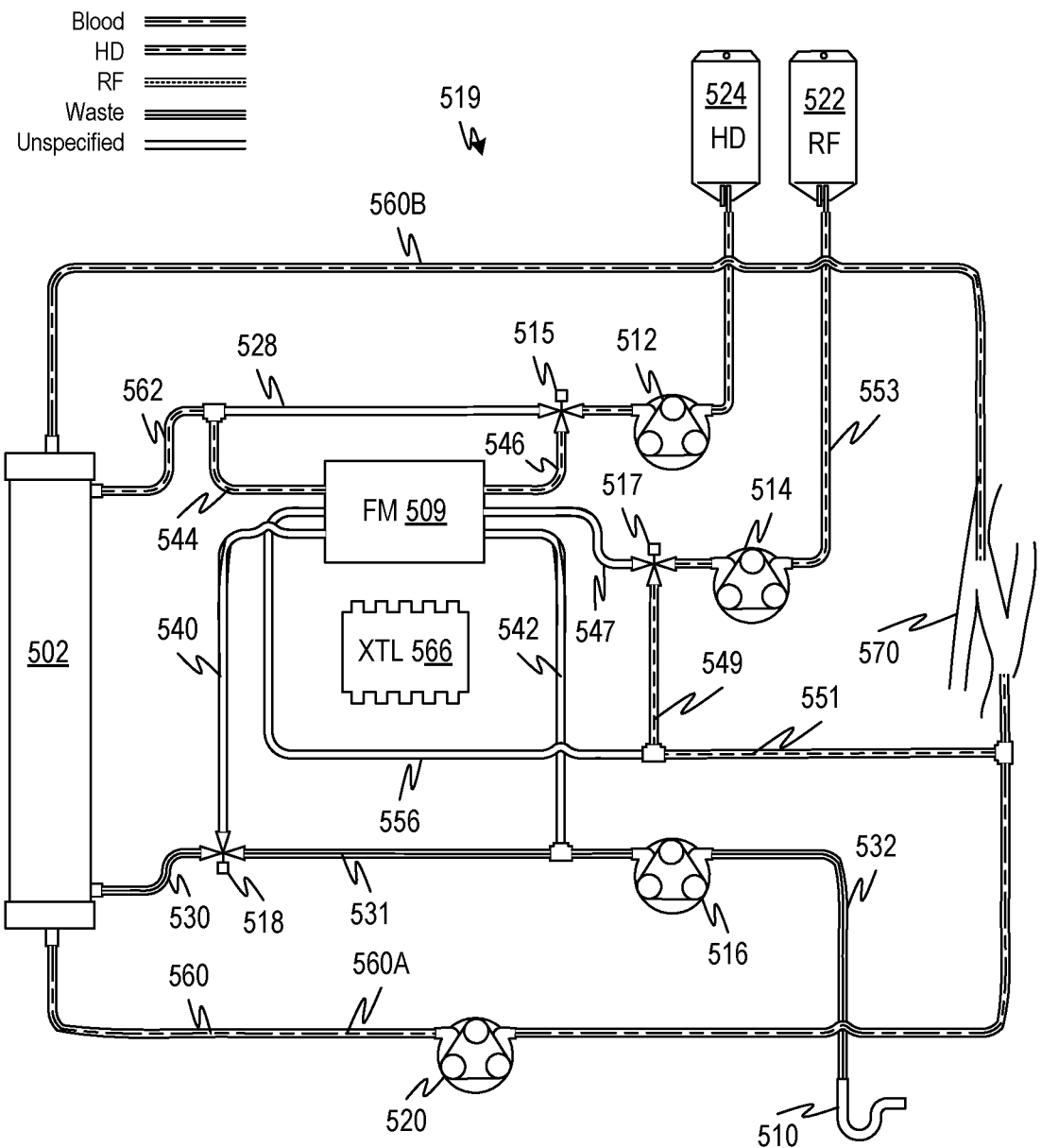
FIG. 5C shows the pumping system of FIG. 5A in a configuration for calibrating a flow rate, according to embodiments of the disclosed subject matter.

At a time of calibration (illustrated in FIG. 5C), the rate of pumping of each of the pumps 512, 514, and 516 can be measured using the flow sensor 509 by diverting a respective one of the flows through the flow sensor 509. The control valves may be configured automatically by the controller before treatment or during a treatment and pumping rates may be varied according to a calibration protocol. The stored calibration data may show a flow rate corresponding to each pump rate, the pump rate being the final measured or commanded rate, for example, the rotational velocity of the shaft of a peristaltic actuator, the drive pulses of a stepping motor, or the pulses from an encoder. Data from the flow sensor 509 indicating the flow rate may be use calibrate each of the pumps 512, 514, and 516. FIG. 5C illustrates the configuration in which the flow is diverted through the flow sensor 509 by the control valve 515. It can be confirmed by inspection that the lines 540, 542, 547, 556, and control valves 517 and 518 are arranged to permit other fluids, including effluent, to flow through the flow sensor 509. Here, fluids are exemplified by dialysate from a source 524 and a replacement fluid or medicament RF from a source 522. Here and elsewhere, the sources may be any source of fluid and may provide any type of fluid, although here they are illustrated using containers as examples. In the present or any of the embodiments, examples of types of medicaments are citrate, pre-diluent, replacement fluid, blood-normal replacement fluid or saline, any medicament or a drug. The rate of the pumps may be indicated to the controller 566 by signals from an encoder in each pump which informs the controller 466 of the exact number of rotations per unit time of the pump (assuming the pumps are peristaltic pumps, but a corresponding method may be used for other types of pumps). Note that other pumping rate sensors are also possible, for example where stepper motor drives are used with the peristaltic pumps, the drive pulses may be counted to determine the speed of the pumps rather than an encoder.

Figure 6:
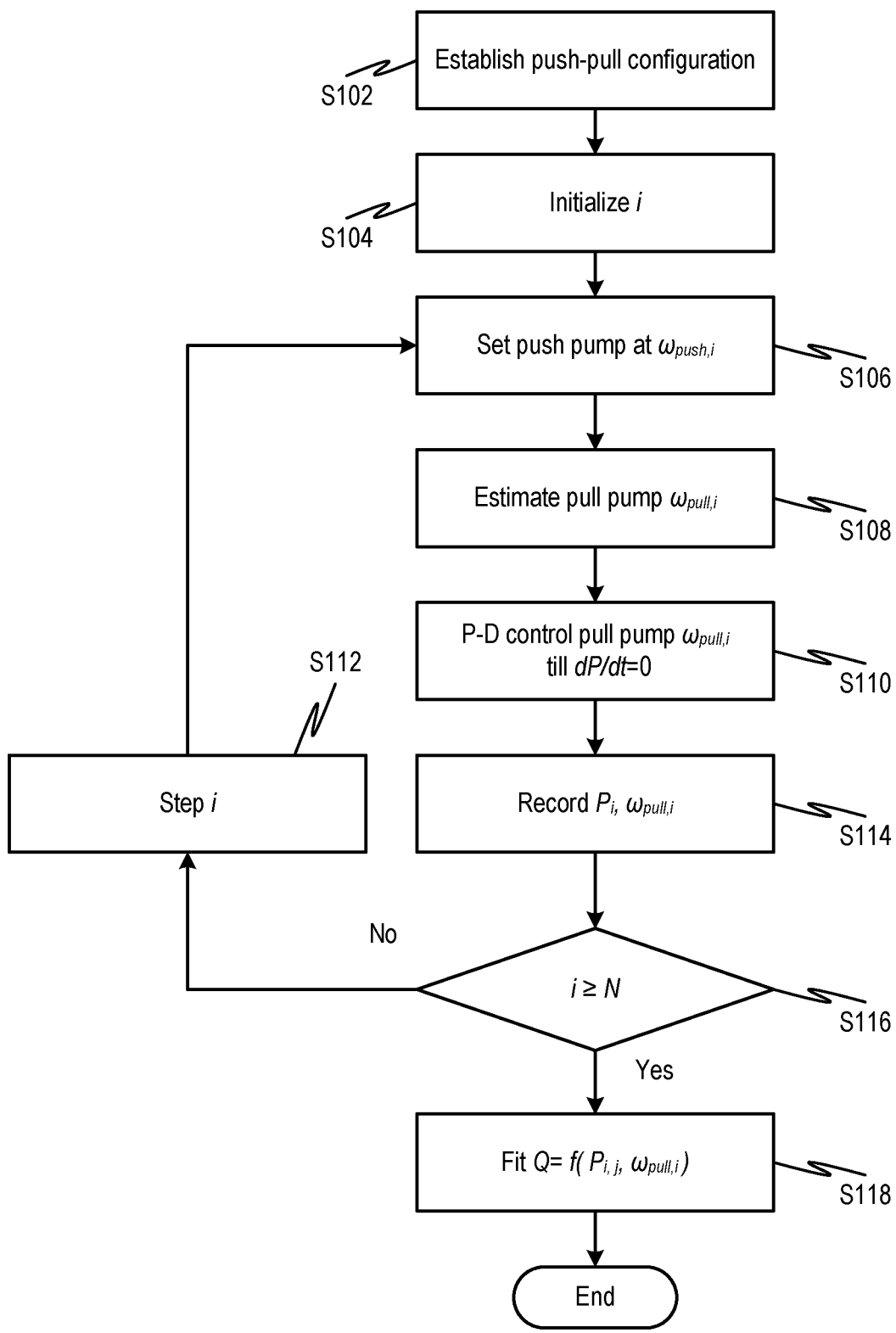
FIG. 6 illustrates control embodiments for performing a calibration for multiple flow rates for various balancing system embodiments of the disclosed subject matter.

FIG. 6 illustrates control embodiments for performing a calibration for multiple flow rates applicable to any of the various extracorporeal blood treatment or balancing system embodiments of the disclosed subject matter. According to the embodiments of FIG. 6, a controller controls the pumping rate of one or more pumps as well one or more control valves to establish configurations of flow balancing systems or devices, for example those of the foregoing or later figures. A digital controller may be programmed to perform the operations presently described, during a set-up phase after a new treatment configuration is established, for example by installing a new disposable and during a priming operation or during an initial phase of treatment. Alternatively, the operation may be performed in a production facility and the calibration parameters needed for the flow model described with reference to S114 may be enclosed with a disposable tubing set.

In an initial operation S102, a push-pull configuration is established between pumps whose flows are to be balanced or proportioned as described herein. This configuration may be established by suitable operation of one or more valves as described herein and in other embodiments capable of establishing a closed circuit between the two pumps, a flow imbalance between which may be detected. The controller may store multiple preselected values of pump speed or a series of values may be computed according to a formula such that, at S104, a value of pump speed may be selected. Then at S106, the pump speed for the push pump may be set at the selected value and at S108, a pump speed for the pull pump may be estimated to match the push pump responsively to a flow model stored in a memory or other data storage in the controller. Then at S110, the estimated value of the pull pump speed may be dynamically changed based on a proportional-differential control algorithm or some other algorithm until, using the accumulator pressure sensor, a match of the push and pull flows, within a predefined range, is established. The match may be determined by seeking a control goal of zero rate of change of accumulator pressure. At S114, one or more pressures (e.g., one or more of the pump inlet and outlet pressures as described in the above-described figures) and the pull pump speed for the currently selected push pump speed are recorded by the controller. Next, at S116, the controller determines if further pump speeds of N pump speeds (N being a predefined number of pump speeds selected to cover a range of flow rates suitable for generating a sufficiently accurate flow model of the pull pump speeds corresponding to any predefined push pump speeds) remain to be selected to complete a calibration operation. If further push pump speeds are to be implemented, then a next push pump speed in a predefined schedule of N pump speeds is selected (S112) and the push pump speed is established by the controller at S106. If the $N^{th}$ push pump speed has already been established at S116, then the controller takes the calibration data (all the pressures and pump speeds recorded at S114) and generates a model by fitting the data at S118. Alternatively, the calibration data may be stored and used directly or by interpolating or extrapolating to identify the pull pump speed that best corresponds to a balanced flow given a given push pump speed.

In the foregoing it was assumed the push pump speed was established and the pull pump speed was determined to match the push pump speed, but it should be clear that in alternative embodiments, the pull pump speed may be first selected and a matching push pump speed determined in S110. Note also that the calibration procedure may be applied to multiple push pumps in push-pull relation to one or more pull pumps. This increases the dimensionality of the model $Q=f(P_{i,j}, \omega_{pull,i})$ and the combination of pumping speeds to be established but otherwise follows the same operations described above. The model may be formed and calibrated to provide a flow rate that is proportional (approximately equal) to the flow rate of the tandem pump.

Note that in the present embodiment, it is assumed that pump speed may be controlled by selecting a shaft speed of a peristaltic pump but other types of pumps may be employed and speed selected by an appropriate control mechanism.

Figure 7:
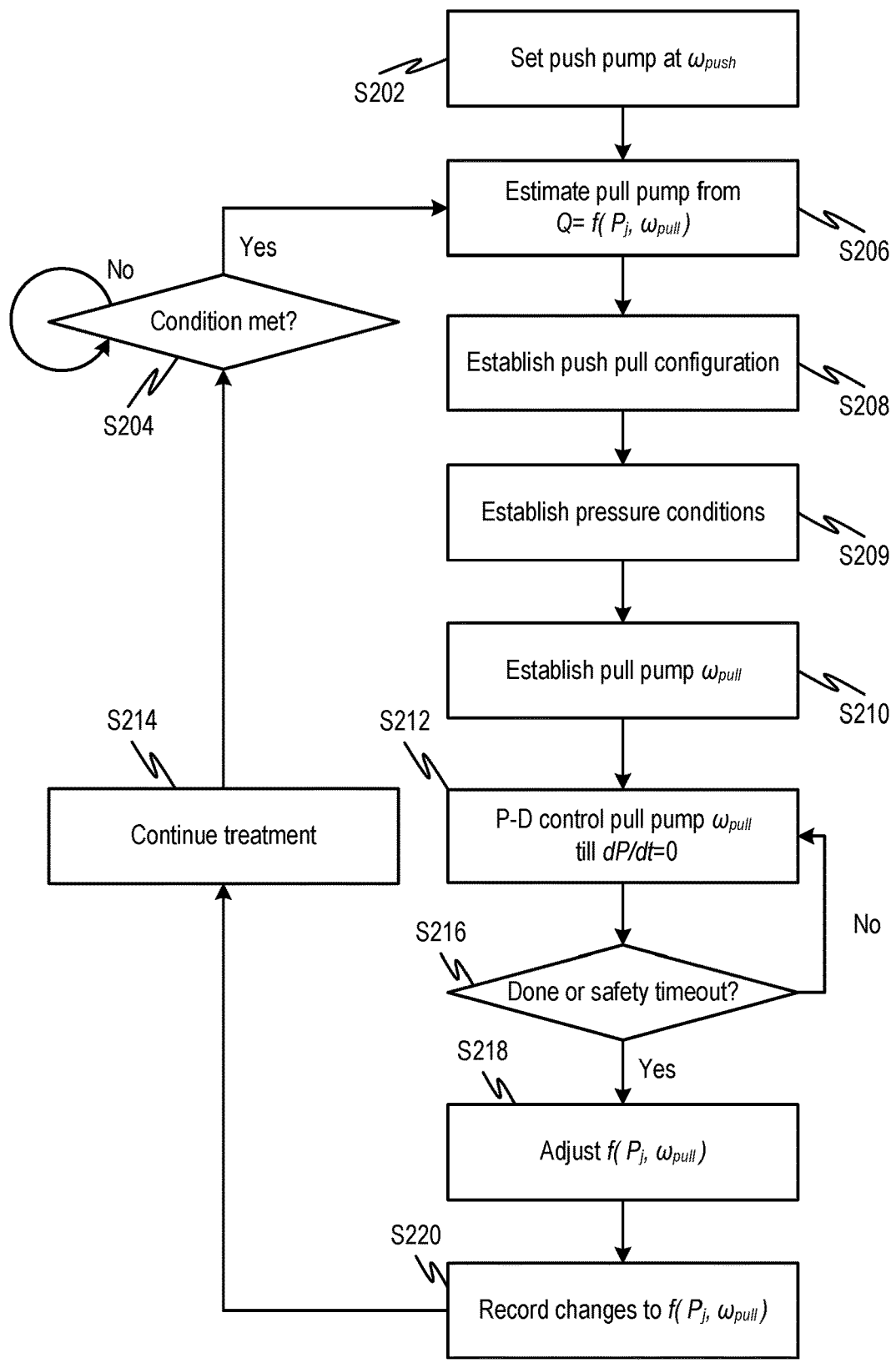
FIG. 7 illustrates control embodiments for checking and/or adjusting flow balance prediction models for various balancing system embodiments of the disclosed subject matter.

FIG. 7 illustrates control embodiments for checking and/or adjusting flow balance prediction models for various extracorporeal blood treatment or balancing system embodiments of the disclosed subject matter. According to the embodiments of FIG. 7, a controller controls the pumping rate of one or more pumps as well one or more control valves to establish configurations of flow balancing systems or devices, for example those of the foregoing or later figures. A digital controller may be programmed to perform the operations presently described, during a set-up phase after a new treatment configuration is established, for example by installing a new disposable and during a priming operation or during an initial phase of treatment. Alternatively, the operation may be performed in a production facility and the calibration parameters needed for the flow model described with reference to S220 may be enclosed with a disposable tubing set. The method of FIG. 7 differs from that of FIG. 6 in that the one or more pumps are calibrated to generate a model that is responsive to both inlet pressure or inlet and outlet pressure as well as rotor speed. The embodiment of FIG. 6 may be modified so that indexes I and j are stepped through where j is an index for an inlet pressure and the calibration prediction function represents flow rate of the pump against both rotor speed and inlet pressure. A third parameter could be added such that pressure difference is stepped through as well. The embodiments of FIG. 7 and FIG. 6 also differ in that the calibration procedure in FIG. 7 may be followed during a usage of the system (such as a treatment).

To begin a usage such as a treatment, a pump, such as a push pump may be set by a controller at a rate selected to establish a predefined flow at S202. At S206, a complementary rotor rate is estimated from a calibration function stored by the controller or accessible to it in some fashion (e.g. stored on the cloud or a web site) to estimate a pull pump rate. At S208, a push-pull configuration is established between pumps whose flows are to be balanced or proportioned as described herein. This configuration may be established by suitable operation of one or more valves as described herein and in other embodiments capable of establishing a closed circuit between the two pumps, a flow imbalance between which may be detected. The controller may store multiple preselected values of pump speed and pressure conditions or a series of values may be computed according to a formula and these pressure conditions and pump speeds may be stepped through in a calibration procedure. This is the above-noted modification of the FIG. 6 embodiment. Alternatively, as discussed with reference to FIG. 7, a new commanded pump rate which is selected based on a production requirement (e.g., a treatment selection) is selected at S202 and the following steps are performed to calibrate at that pump speed (or in a modification, at a number of speeds near that pump speed). At S208, the push pull configuration is established. At S209, selectable flow restrictors are adjusted to establish a selected pressure condition (again, inlet pressure of one or both of the pumps or an outlet pressure of one or both of the pumps or a combination of any or all of these). A S210, the pull pump is run. This latter step may be done simultaneously with S209. At S212, the estimated value of the pull pump speed may be dynamically changed based on a proportional-differential control algorithm or some other algorithm until, using the accumulator pressure sensor, a match of the push and pull flows, within a predefined range, is established. In this embodiment or those described with reference to FIG. 6, the push pump speed may be altered to match that of the pull pump instead or both speeds may be modified to match each other. The match may be determined by seeking a control goal of zero rate of change of accumulator pressure. During the S212, control may loop through S216 to bail out of the PID control function if it is taking too long. Once the flow rates are matched, the function mapping the pressure conditions and pump rotor speeds to flow is adjusted for the current conditions at S218 and the current selected flow rates established according to the revised function. If necessary depending on how or where the data are stored, the update may be stored elsewhere at S220, such as on a cloud storage. At S214, the production mode continues until a period of time lapses, or a change in the condition of the production mode occurs such as a lapse of time as indicated at S204.

The calibration procedure may be repeated by step S204 for a number of different conditions during a production run (e.g., treatment) or between consecutive production runs. Possible conditions include number of rotations of a pumps rotor per the pump tubing segment or per the pump itself, or both, since the last calibration; the number of occlusions of a roller per the pump tubing segment or per the pump itself, or both, since the last calibration; total run time on the pump tubing segment or the pump, total time the pump tubing segment has been installed on the pump, Any of these factors may be established according to temperature, temperature change between production runs or during a production run, maximum potential flow rate, a predefined allowed error rate, temperature change, pressure change, etc.

At S212, one or more pressures (e.g., one or more of the pump inlet and outlet pressures as described in the above-described figures) and the pull pump speed for the currently selected push pump speed are recorded by the controller. Next, at S116, the controller determines if further pump speeds of N pump speeds (N being a predefined number of pump speeds selected to cover a range of flow rates suitable for generating a sufficiently accurate flow model of the pull pump speeds corresponding to any predefined push pump speeds) remain to be selected to complete a calibration operation. If further push pump speeds are to be implemented, then a next push pump speed in a predefined schedule of N pump speeds is selected (S112) and the push pump speed is established by the controller at S106. If the N th push pump speed has already been established at S116, then the controller takes the calibration data (all the pressures and pump speeds recorded at S114) and generates a model by fitting the data. Alternatively, the calibration data may be stored and used directly or by interpolating or extrapolating to identify the pull pump speed that best corresponds to a balanced flow given a given push pump speed.

Figure 9:
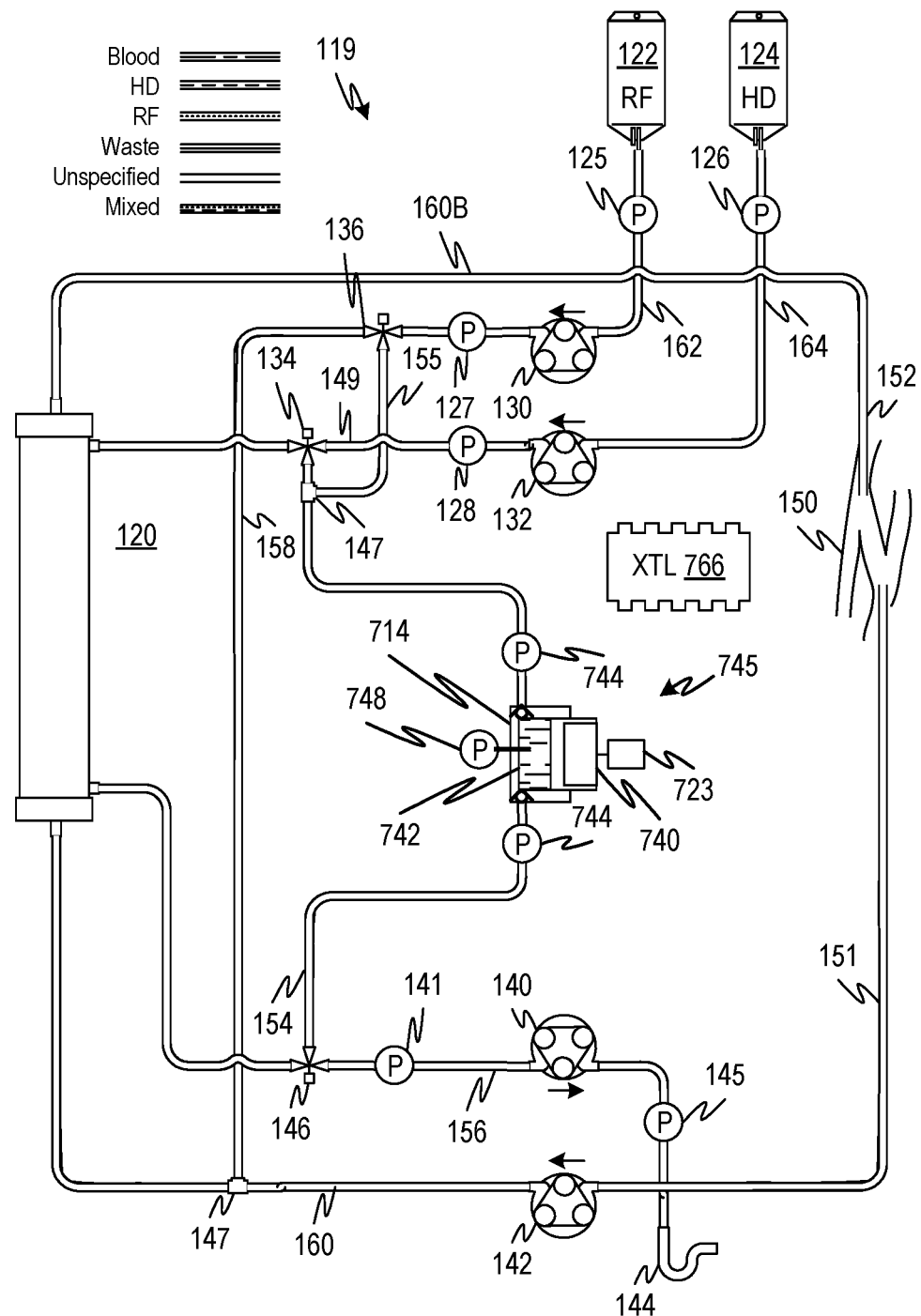
FIG. 9 illustrates an active accumulator that may be used with any of the embodiments in place of a passive accumulator to create new embodiments, according to embodiments of the disclosed subject matter.

FIG. 9 shows a flow balancing system that is substantially the same as described with reference to FIGS. 2A through 2D and operable in the same modes described in connection with respect to those figures. The embodiment of FIG. 9 includes an active accumulator 745 in place of the fixed accumulator 138. The active accumulator has a pressure sensor 748 that detects pressure in an interior volume 742 whose size is selectable by a piston 740 actuated by an actuator 723 under control of a controller 766. Pressures into and out of the accumulator may be measured by respective pressure sensors 744, respectively. During calibration, the suction head of the pull pump may be different from the suction head of the pull pump during normal production mode operation because of the flow path change. Since peristaltic pumps are sensitive to suction head variability, the volumetric efficiency of the pump during calibration may be different from that during operation which is undesirable. The controller can regulate the volume of the accumulator so as to establish a predefined pressure at the pull pump and then use the rate of change of volume indicated by the actuator 723 displacement as an indicator of the mismatch in flow rate rather than the pressure of the accumulator. Thus, the synchronization process is fed an error indicative of the volume of the accumulator not the pressure. Synchronization may be performed otherwise as in any of the disclosed embodiments. Preferably, the active accumulator 745 is of such design that its interior volume is precisely known given the displacement of the actuator 723. For example, a cylinder and piston arrangement of stiff materials may be used.

Figure 10:
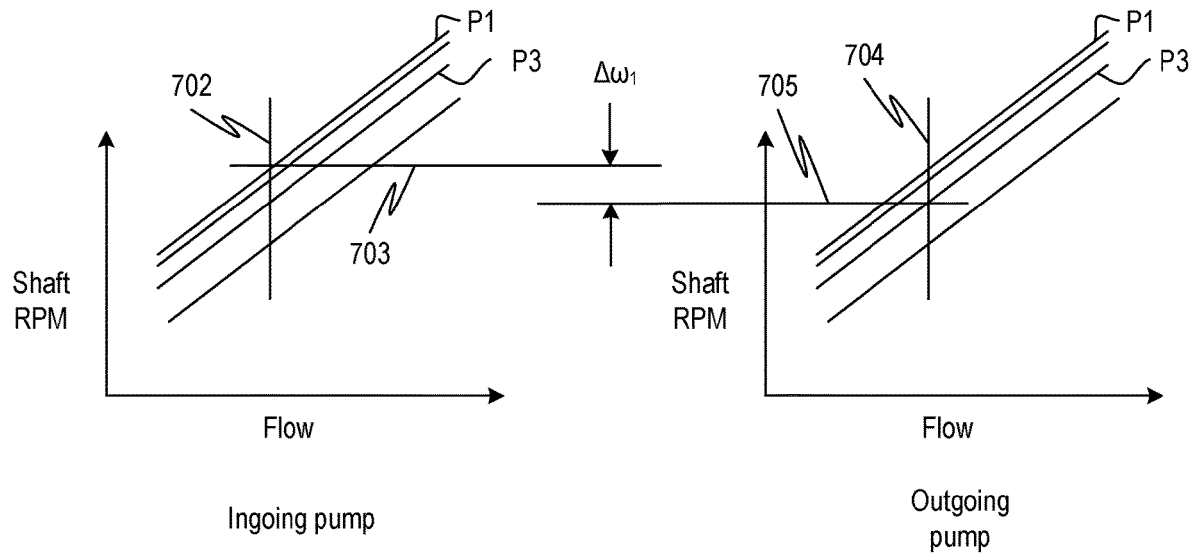
FIG. 10 shows a method for calibrating one pump against another in which a volumetric efficiency of one of the pumps is altered so as to speed the matching of flow rates in a push-pull arrangement, according to embodiments of the disclosed subject matter.

FIG. 10 shows a method for calibrating one pump against another in which a volumetric efficiency of one of the pumps is altered so as to speed the matching of flow rates in a push-pull arrangement, according to embodiments of the disclosed subject matter. The graphs show a characteristic pump curve correlating shaft RPM with flow for different inlet pressures or "suction head." In any of the embodiments, when operated in push-pull mode, the controller may choose suction head or volumetric efficiency of pump so that the net flow rate into the branch does not coincide predefined pulse rate and/or phase relationships of the push and pull pump pulsatile flow that makes it difficult to converge quickly and accurately to a synchronous pumping rate coinciding with zero average net flow into the branch (i.e., equal flow rates of the push and pull pumps). In the illustrated example, the inlet pressure of one of the pumps has been adjusted to P3 with the other pump remaining at P1 thereby creating a matching flow condition with a selected difference in the angular speeds of the pumps Awi as illustrated.

Figure 11:
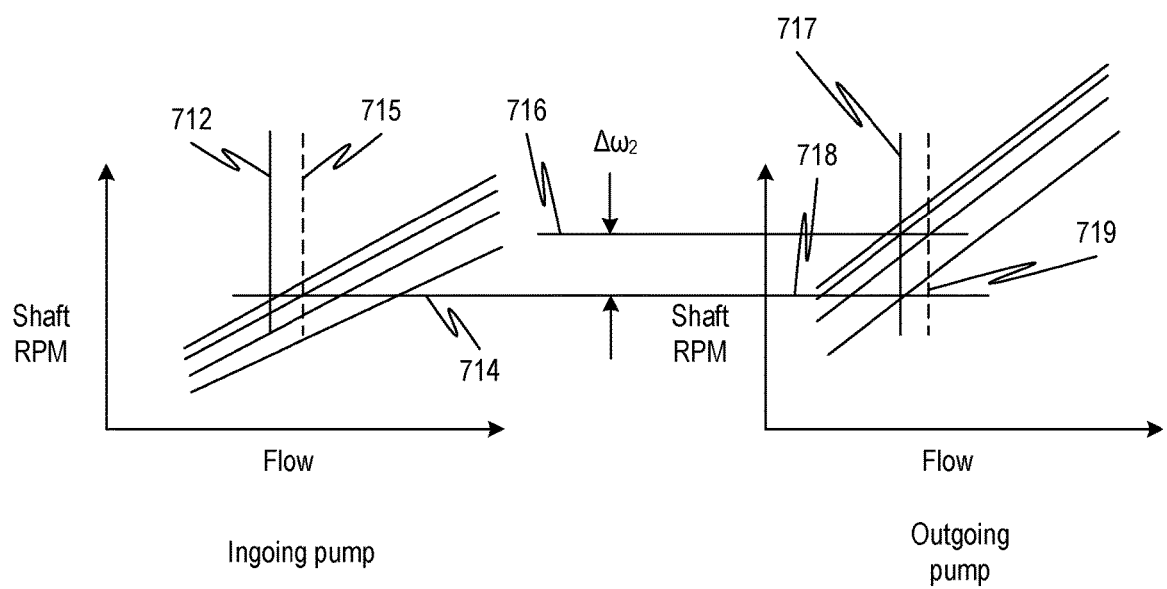
FIG. 11 shows a method for calibrating one pump against another in which a calibration is set up by controlling total flow so as to avoid conditions that are predicted to result in a slow speed of matching of flow rates in a push-pull arrangement, according to embodiments of the disclosed subject matter.

FIG. 11 shows a method for calibrating one pump against another in which a calibration is set up by controlling total flow so as to avoid conditions that are predicted to result in a slow speed of matching of flow rates in a push-pull arrangement, according to embodiments of the disclosed subject matter. In the FIG. 11 example, instead of changing the conditions of one of the pumps, the total flow rate is adjusted to avoid the difficult-to-synch condition identified with reference to FIG. 10. In this case, the pumps may be non-identical and under certain flow rate conditions, the two pumps may produce a pulsatile pattern that causes the synchronization process to converge slowly due to, for example, very slow beats which may introduce a sample bias in the average pressure estimation of the branch.

FIGS. 12A and 12B show multiple line peristaltic pump configurations in which the flow in two lines are adjusted relative to each other by restricting flow into or out of the pumps by a control valve such that the flow can be matched, according to embodiments of the disclosed subject matter. A single rotor 750 has multiple rollers 751, for example the eight shown. Two or more pumping tube segments 752 and 754 engage the rollers for substantially balanced flow to and from a treatment device. The flow of either line 752 or 754 may be adjusted independently of the other by adjusting a flow restriction on the inlet (760 and/or 761) or the outlet (762 and/or 766) or both. In this way, pumping can be synchronized and calibration done according to the various embodiments by changing a flow restriction rather than a pumping rate. In the embodiment of FIG. 12B, two different rotors 781 and 782 which may or may not be driven by the same motor. In this embodiment, the flow rate is controlled by regulating flow restrictors 760 and/or 761 as in the embodiment of FIG. 12A. Outlet restrictors may also be provided. Any number of pumping tube segments or segment-rotor combinations may be used.

FIG. 13 shows properties of a peristaltic pump with a variable rotation rate, according to embodiments of the disclosed subject matter. Peristaltic pumps alternately pump and occlude as the rotor rotates producing a pulsatile flow. The variability of this pulsation be reduced by shorting the occlusion interval by increasing the rotor speed to shorten the occlusion interval. The variable speed rotation rate and volume rate curves illustrate this for comparison between conventional and variable speed. This may be implemented using a stepper motor, for example. The point of occlusion can be detected by a pressure or flow sensor connected to a controller and used by the controller to regulate the pump rate with angle of displacement to achieve the effect shown.

Figure 14:
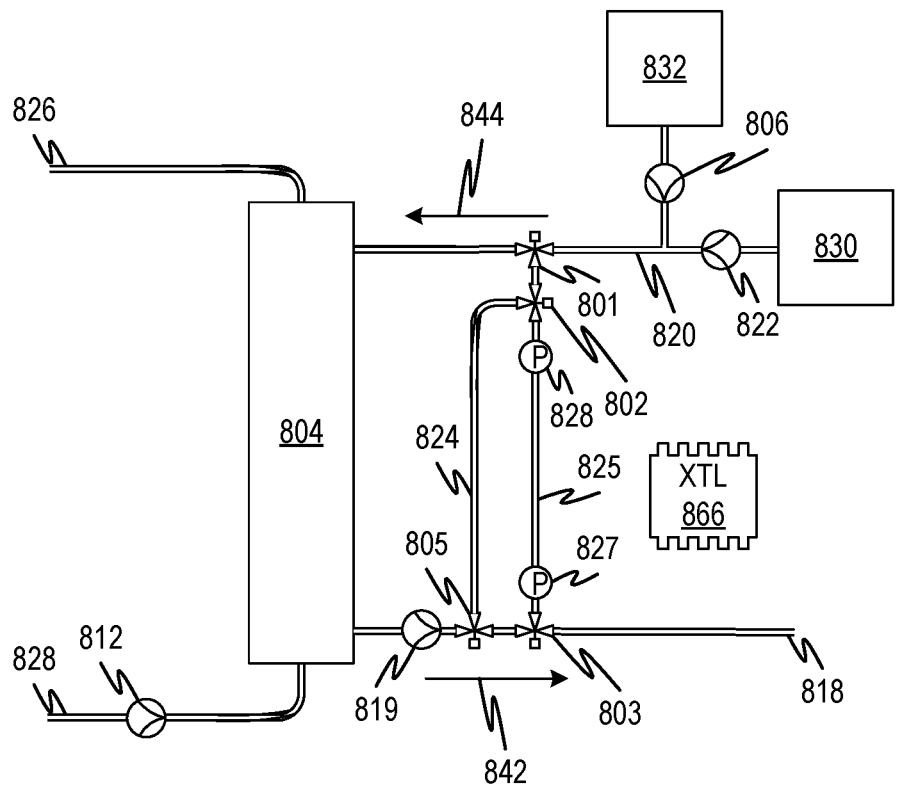
FIGS. 14 and 15 illustrate methods and systems for matching flows between pumps for purposes of calibration using a common flow path according to embodiments of the disclosed subject matter.

FIG. 14 illustrates a system and method of matching flows between pumps for purposes of calibration using a common flow path 825 according to embodiments of the disclosed subject matter. Blood is pumped by blood pump 812 through venous 828 and arterial blood lines through a dialyzer 804. Fluids 832 and 830 are pumped through the dialyzer 804 through line 820 by pump 822 and 806 and removed from the dialyzer 804 by pump 819. To synchronize pump combination 806 and 822 with pump 819, pump 819 may flow through a common segment 825 with pressure sensors 828 and 827 positioned to measure a pressure drop therealong. The flow path through the common segment 825 may be defined by the controller which may set control valves 801, 802, 803, and 804 to flow fluid from 832 and 830 through the common segment 825 and then flow from the dialyzer 824 through the common segment 825 at separate times.

During treatment, the flow may be as indicated by arrows 842 and 844. During a first calibration mode, pump 806 is not run and flow from pump 822 passes through valve 801 though valve 802 through common segment 825, through valve 803 and out through waste line 818. The pressure drop in the common segment 825 as indicated by pressure sensors 828 and 827 is recorded. This may be repeated for several flow rates at a single time. The first calibration mode may be instantiated at times during treatment, during a priming operation, after manufacturing, or at other times. The instantiation during treatment may be triggered by various events as identified below. During a second calibration mode flow from pump 806, pump 822 is not run and flow passes through valve 801 though valve 802 through common segment 825, through valve 803 and out through waste line 818. The pressure drop in the common segment 825 as indicated by pressure sensors 828 and 827 is recorded. This may be repeated for several flow rates at a single time. The second calibration mode may be instantiated at times during treatment, during a priming operation, after manufacturing, or at other times. The instantiation during treatment may be triggered by various events as identified below. During a third calibration mode flow from pump 819 passes through valve 805 though valve 802 through common segment 825, through valve 803 and out through waste line 818. The pressure drop in the common segment 825 as indicated by pressure sensors 828 and 827 is recorded. This may be repeated for several flow rates at a single time. The third calibration mode may be instantiated at times during treatment, during a priming operation, after manufacturing, or at other times. The instantiation during treatment may be triggered by various events as identified below. During a fourth calibration mode, both pumps 806 and 822 may be operated simultaneously with suitable settings of the valves to cause the flow to pass through the common segment 825. Any combination of these calibration modes may be instantiated at various times as indicated. See FIG. 20 for an example method embodiment which is applicable to any of the embodiments disclosed herein.

The pressure drop data captured during the calibration instances may be used to adjust stored pump functions that relate pressure, flow, and pump axis speed as discussed elsewhere herein. Note that the calibration may be based on a common reference pump and all the other pumps may be calibrated to that standard. This bases the accuracy of all the pumps dependent on the accuracy of the reference pump. But the accuracy of the pumps relative to each other can be much greater. In dialysis treatment, the rate of flow of dialysate can vary by 10% but it is desirable for the accuracy of differential flow, upon which ultrafiltration is based, to be much more accurate than that. Examples of reference pumps are any of the pumps in the system. Note that more than one reference pump may be used in a single embodiment.

Note that although the embodiment of FIG. 14 shows two fluid sources 826 and 828, other fluids could be added or one of these two could be subtracted to form new embodiments. Also, the fluids could be used for predilution or post-dilution of blood, for drug or medicament infusion into blood, or for various other purposes as described in connection with the various embodiments. It should be clear from the above that there is a benefit to flowing fluid through the exact same common tube 825. This eliminates any error due to difference in the size or other properties of the tube 825 thereby ensuring more accurate pressure drop data.

The common segment 815 may be calibrated with a standard solution such as blood normal saline in order to obtain a flow vs. pressure drop curve. Thereafter, the flow can be calculated based on the flow vs. pressure drop curve for calibration of pumps. The curve data may be generated for multiple temperatures and multiple fluids. The common segment 825 may be made of a durable material with consistent mechanical properties. Upon manufacture, the common segment 825 may be permanently sealed to a fluid circuit to complete manufacture thereof.

Figure 15:
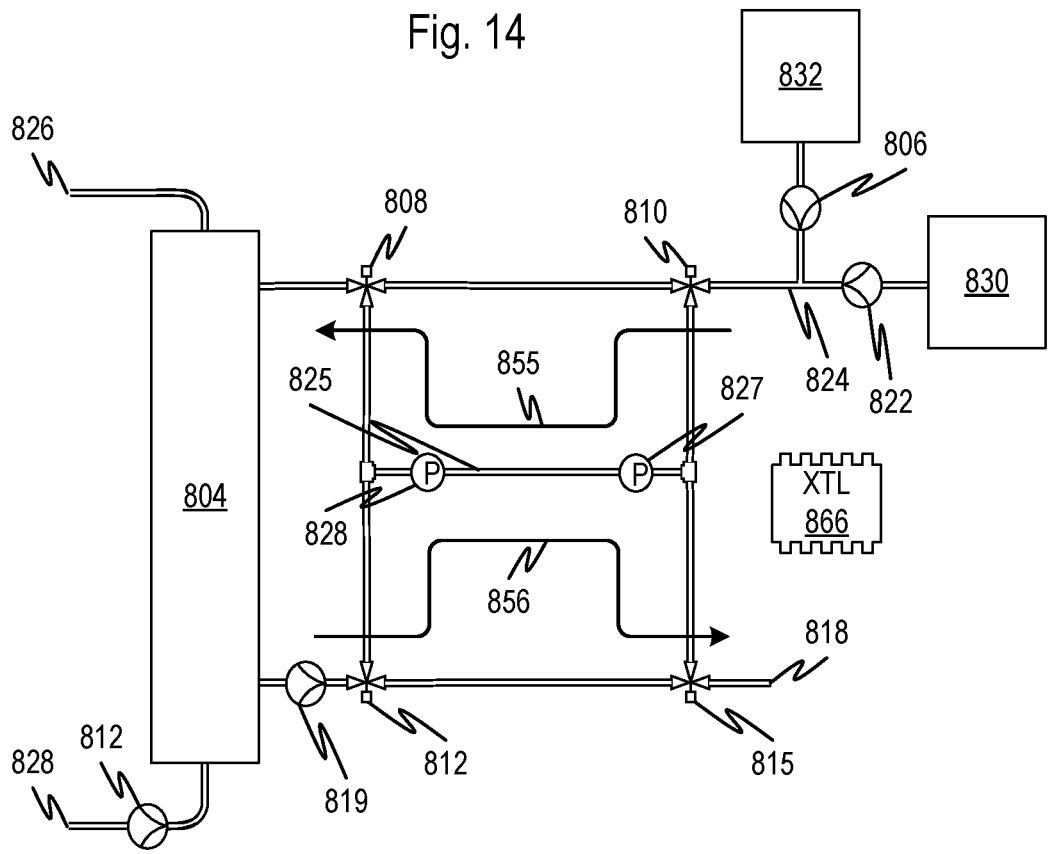

FIG. 15 illustrates a system with a common segment 830 configured in such a way that the pressure loss of fluid as it flows through the common segment 830 can be obtained without can be used without wasting fluid. The ingoing pump or combination thereof (e.g., 806, 822 and/or others) can be directed by valves 810 and 808 to flow through the common segment 825 as indicated by arrow 855 at first times. The outgoing pump or combination thereof (e.g., 819 and/or others) can be directed by valves 815 and 812 to flow through the common segment 825 as indicated by arrow 856 at second times. The pressure drop data acquired may be used as discussed with reference to FIG. 15.

Figure 16:
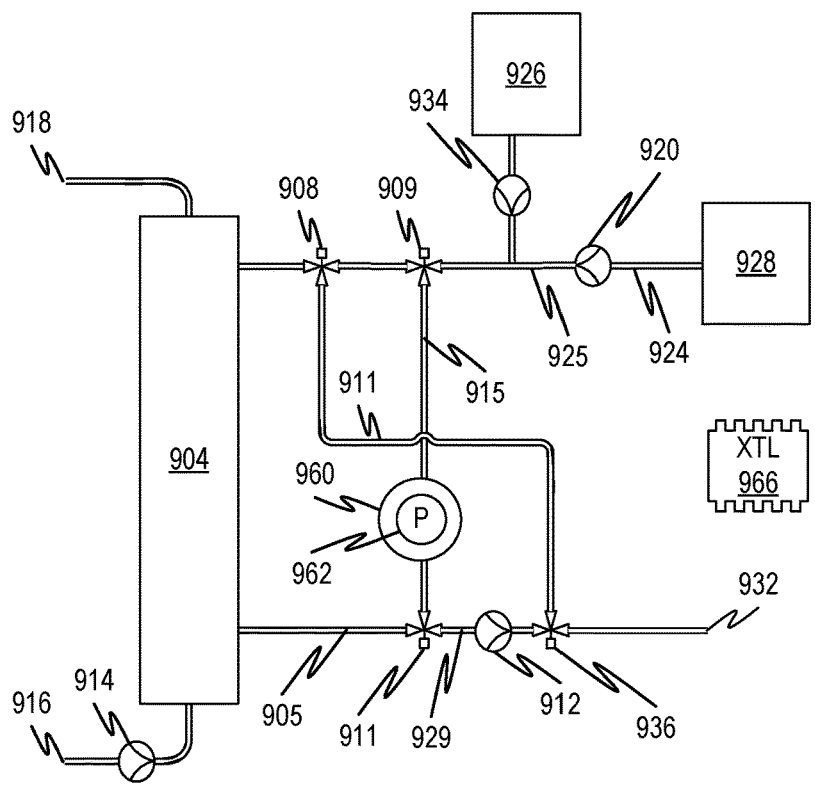
FIGS. 16 through 19 illustrate systems for conserving treatment fluid used for calibration according to embodiments of the disclosed subject matter.

FIGS. 16 through 19 illustrate systems for conserving treatment fluid used for calibration according to embodiments of the disclosed subject matter. In FIG. 16, a branch channel 915 serves the same function as in 154, 441 in prior embodiments and others described but not shown in figures. Unlike the earlier embodiments, during calibration, the flow through the branch channel 915 is recovered after it flows through the pull pump 912 through a line 911 where it is flows into the treatment device 904. An accumulator 960 may be provided. A pressure sensor 962 may also be provided. These serve the same functions described above and elsewhere herein, namely, to synchronize flow between pumps 920, 934, and/or 912 calibrated against a reference one of the pumps 920, 934, or 912.

During treatment, pump 920 and 934 pump fluid into a fresh medicament line 925 through valves 908 and 909. The fluid passing into fresh medicament line 925 passes through the treatment device 904 to a spent medicament line 905, through the valves 911 and 936 pumped by pump 912. Finally spent medicament is discarded through a spent medicament waste line 932.

During respective calibration procedures, fluid may be pumped by pump 920 and/or 934 through the branch line 915 through pump to synchronize with pump 912 and then pass out through the spent medicament waste line 932 where it is discarded. The calibrating flow may be established by valves 909, 911 and 936 and the operation/non-operation of the pumps 920 and 934 such that one or both of pumps 920 and 934 are in push-pull relationship with pump 912. Initially, upon establishment of a calibration instance, valve 936 may send fluid from a pumping channel 929 between valves 911 and 936 out through spent medicament waste line 932 until fresh medicament clears the pumping channel 929. This may be determined by the controller 966 as the passing of a sufficient volume through it upon instantiation of the calibration responsively to flow rate and time. After an interval during the respective calibration procedure, the interval being long enough for spent medicament to clear the pumping channel 929 between valve 911 and valve 926 (which may be longer than the minimum required for certainty that spent medicament is flushed), the valve 936 may set to convey fluid through fresh medicament line 911 through valve 908, which may be set to convey the fresh medicament to the treatment device 904. In this way, the quantity of fresh medicament used for calibrating can be minimized.

Figure 17:
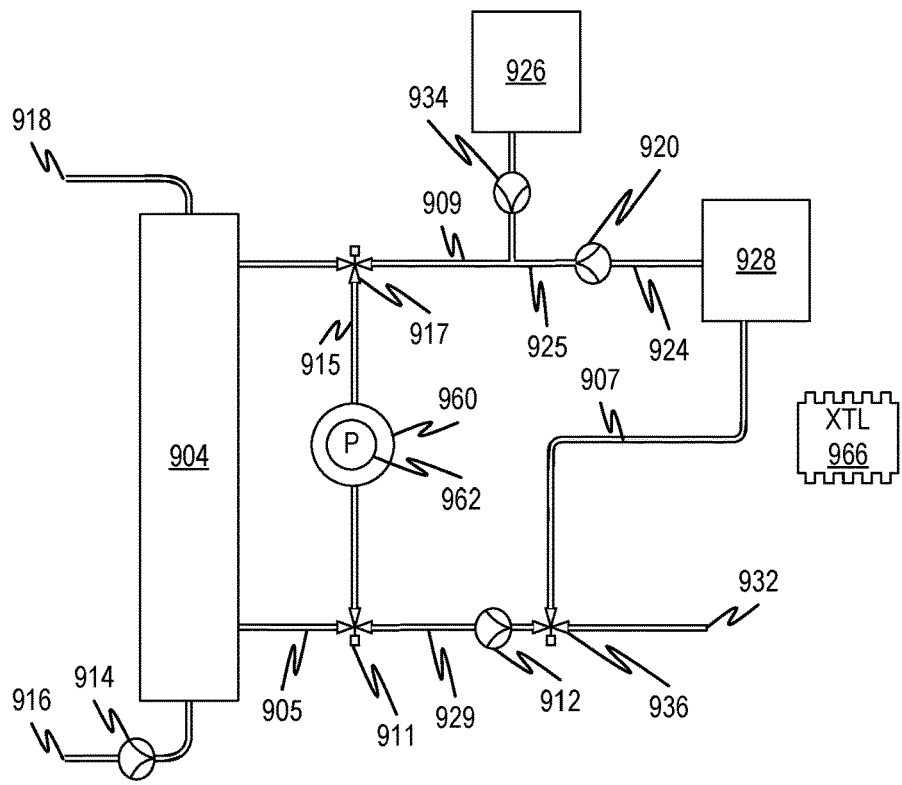

The configuration of FIG. 16 may be suitable for online medicament generation (embodiment of source 928) such as provided in dialysate clinics. The configuration of FIG. 17 may be suitable for medicament supplied using a container (embodiment of source 928). In FIG. 17, a branch channel 915 serves the same function as 915 of FIG. 16 and previous figures (e.g. 154, 441) in prior embodiments and others described but not shown in figures. As in the embodiment of FIG. 16, during calibration, the flow through the branch channel 915 is recovered after it flows through the pull pump 912 through a line 907 where it is flows into a source container embodiment of source 928 thereby recovering it.

An accumulator 960 may be provided. A pressure sensor 962 may also be provided. These serve the same functions described above and elsewhere herein, namely, to synchronize flow between pumps 920, 934, and/or 912 calibrated against a reference one of the pumps 920, 934, or 912.

During treatment, pump 920 and 934 pump fluid from sources 926 and 928 into a fresh medicament line 907 through valves 908 and 909. The fluid passing into fresh medicament line 907 passes through the treatment device 904 to a spent medicament line 905, through the valves 911 and 936 pumped by pump 912.

During respective calibration procedures, fluid may be pumped by pump 920 and/or 934 through the branch line 915 through pump to synchronize with pump 912 and then pass out through the spent medicament line waste line 932 where it is discarded. The calibrating flow may be established by valves 909, 911 and 936 and the operation/non-operation of the pumps 920 and 934 such that one or both of pumps 920 and 934 are in push-pull relationship with pump 912. Initially, upon establishment of a calibration instance, valve 936 may send fluid from a pumping channel 929 between valves 911 and 936 out through spent medicament waste line 932 until fresh medicament clears the pumping channel 929. This may be determined by the controller 966 as the passing of a sufficient volume through it upon instantiation of the calibration responsively to flow rate and time. After an interval during the respective calibration procedure, the interval being long enough for spent medicament to clear the pumping channel 929 between valve 911 and valve 926 (which may be longer than the minimum required for certainty that spent medicament is flushed), the valve 936 may set to convey fluid through fresh medicament line 907 to the source 928, which may a container or a manifold connected to multiple containers. In this way, the quantity of fresh medicament used for calibrating can be minimized.

Figure 18:
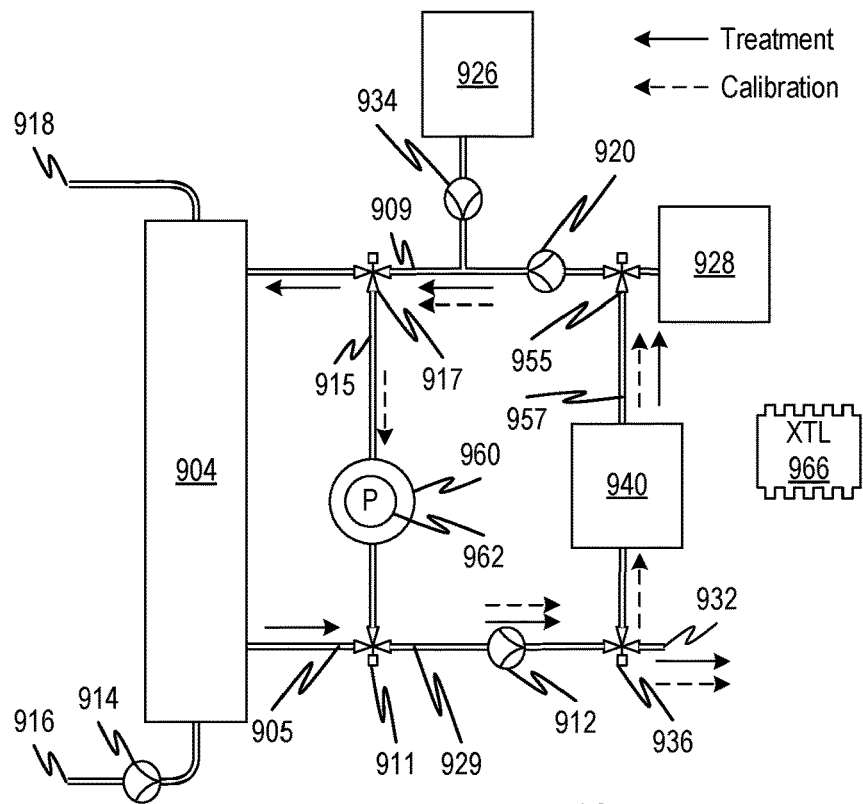

The configuration of FIG. 18, like the configuration of FIG. 16, may be suitable for online medicament generation (embodiment of source 928) such as provided in dialysate clinics. In the embodiment of FIG. 18, a branch channel 915 serves the same function as 915 of FIG. 16 and previous figures (e.g. 154, 441) in prior embodiments and others described but not shown in figures. During calibration, the flow through the branch channel 915 is recovered after it flows through the pull pump 912 through a line 957 where it is flows into a recovery container 940 where it is stored until the collected medicament therein can be pumped by the pump 920 by selecting a corresponding position of the valve 955. The valve 955 may be controlled to select either an online source 928 (or other source, such as a container embodiment) or the recovery container 940 depending on the fill status of the recovery container 940.

An accumulator 960 may be provided. A pressure sensor 962 may also be provided. These serve the same functions described above and elsewhere herein, namely, to synchronize flow between pumps 920, 934, and/or 912 calibrated against a reference one of the pumps 920, 934, or 912.

During treatment, pump 920 and 934 pump fluid from sources 926 and 928 into a fresh medicament line 907 through valves 908 and 909. The fluid passing into fresh medicament line 907 passes through the treatment device 904 to a spent medicament line 905, through the valves 911 and 936 pumped by pump 912.

During respective calibration procedures, fluid may be pumped by pump 920 and/or 934 through the branch line 915 through pump to synchronize with pump 912 and then pass out through the spent medicament line waste line 932 where it is discarded. The calibrating flow may be established by valves 909, 911 and 936 and the operation/non-operation of the pumps 920 and 934 such that one or both of pumps 920 and 934 are in push-pull relationship with pump 912. Initially, upon establishment of a calibration instance, valve 936 may send fluid from a pumping channel 929 between valves 911 and 936 out through spent medicament waste line 932 until fresh medicament clears the pumping channel 929. This may be determined by the controller 966 as the passing of a sufficient volume through it upon instantiation of the calibration responsively to flow rate and time. After an interval during the respective calibration procedure, the interval being long enough for spent medicament to clear the pumping channel 929 between valve 911 and valve 926 (which may be longer than the minimum required for certainty that spent medicament is flushed), the valve 936 may set to convey fluid through fresh medicament line 907 to the recovery container 940. In this way, the quantity of fresh medicament used for calibrating can be minimized.

Figure 19:
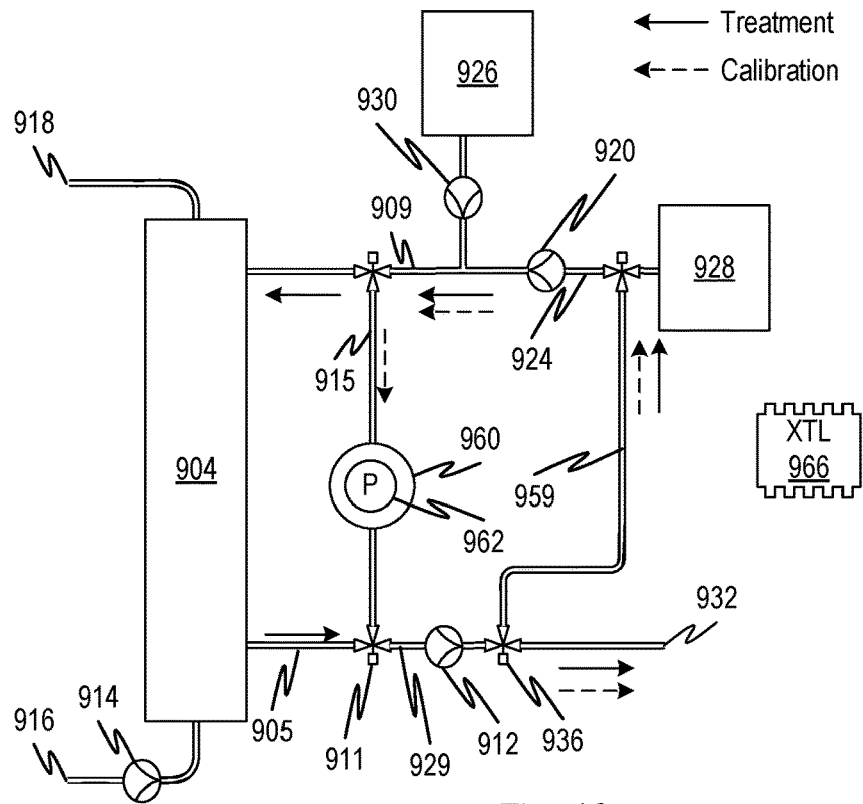

The configuration and operation of the embodiment of FIG. 19 is similar to that of FIG. 18, except that there is no recovery container in a line 959 such that during calibration, a closed loop may be formed whereby fresh medicament recirculates in channels 959, 909, 915 and 929 once the pumping channel 929 is cleared after initiation of the calibration procedure. Note that an accumulator may be included in the line 959 to mitigate pressure interaction between the pumps 920 and 912.

In variants of the embodiments of FIGS. 17, 18, and 19, if pump 930 is desired to be calibrated against pump 912, the fluid in source 926 may be passed through medicament waste line 932 and discarded, during calibration. In these embodiments, medicament may be recovered during calibration of pump 920. In the embodiments of FIGS. 16-19, all references to medicament may be replaced by drug or infusate or other descriptor in alternative embodiments as it should be clear the embodiments are not limited to the particular fluids identified in the description of the operation and configuration.

Figure 20:
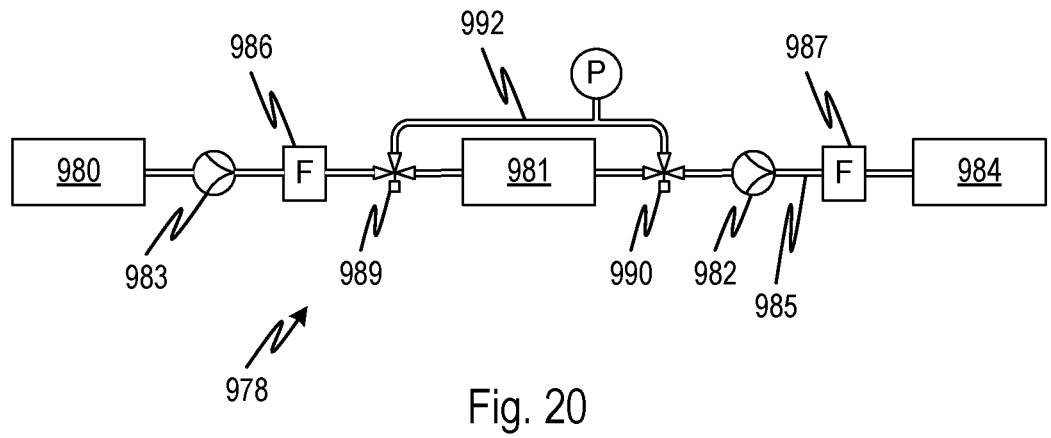
FIG. 20 shows a generalized schematic diagram of a system for balancing flows according to embodiments of the disclosed subject matter.

Referring to FIG. 20, a general flow system 978 has a fluid source, a channel that may have a component 981 thereal-ong, and a fluid receiver 984 which may or may not be the same as the source 980. All of these are connected by a fluid channel 985 and pumped by peristaltic pumps 982 and 983. In embodiments, the fluid carried by the system is any fluid. In further embodiments, the fluid is aqueous. In further embodiments, the fluid is incompressible. It should be evident the previous embodiments have the characteristics of the system of FIG. 20 during production or treatment mode. In embodiments, the component 981 permits the flow rates of the two pumps 982 and 983 to differ, for example, if it is a dialyzer, there may be a net fluid flow into or out of the component 981. In the embodiment, it is desired to have a predefined relationship between the flow rates created by the two peristaltic pumps 982 and 983. This relationship may be maintained by controlling the rates of the pumps 982 and 983. However, peristaltic pumps 982 and 983 it may not be possible to determine the rate of flow by controlling the flow conditions of peristaltic pumps 982 and 983, for example their inlet pressures and shaft speeds, since these may change during operation, vary due to manufacturing variability, and other factors. Thus, flow sensors may be used such as flow sensors 986 and 987. Flow sensors 986 and 987 may be used to measure flow into component 981 and out of component by sampling and averaging over a time window in order to obtain a time-moving average that may be used to control the speeds of the pumps to maintain the desired flow ratio and net volume transferred into or out of the component 981. Alternatively, as described with embodiments herein-described, a branch channel 992 may be selectively interposed by valves 989 and 990 under control of a controller. In this temporary calibrating flow configuration, as discussed elsewhere, the flow rates of the pumps are actively matched using a pressure signal in the branch channel 992. There may be no need for the flow sensors 986 and 987.

In the system 978, in the production (or treatment) or calibrating configuration, the peristaltic pumps 982 and 983 can interact in such a way as to cause instability in the flow which can cause the flow to be non-repeatable or such that a computed sum of the individual flow rates, predicted by the rotation speed (even if derived from a calibration) of the two peristaltic pumps 982 and 983 departs substantially from the net flow rate when the two peristaltic pumps 982 and 983 are connected as shown. It has been found that this variability can be minimized by operating such that a substantial difference in the frequencies of the pulses produced by the two peristaltic pumps 982 and 983 is always maintained during operation. For example, in a dialysis system, where the component 981 is a dialyzer and nearly equal flow rates are desired to be maintained in the two pumps to produce a balanced inflow and outflow to/from the component 981, the two peristaltic pumps 982 and 983 may have a different number of rollers. Alternatively, the pumping tube diameters used with identical peristaltic pumps 982 and 983 may be different from each other sufficiently to ensure the frequency difference. In other embodiments, the suction head of the pumps may be selected using a flow resistance to ensure the frequency difference.

In embodiments, the system of FIG. 20 operates over a predefined range of flow rates and the combination of pump tube diameters, number of rollers, and suction side flow resistances of the pumps are such that, over substantially all of the predefined range of flow rates, the pulse rates of the pumps are different and they are never operated during an operating function where the flow balance is required, such that the frequencies are within 5% of each other. In embodiments, the ratio of the inverse of the difference between the pulse frequencies of the pumps is multiple times the calibration interval. In embodiments, the ratio is always greater than 3 times the calibration interval. In embodiments, the ratio is always greater than 5 times the calibration interval. In embodiments, the ratio is always greater than 8 times the calibration interval. In embodiments, the ratio is always greater than 12 times the calibration interval.

In the embodiments of FIG. 20, the fluid circuit connecting the pumps may lack a pressure dampening device such as one or more chambers in the fluid circuit. It has been demonstrated that pressure pulses can be substantially mitigated by dampeners but this adds considerable cost to a disposable fluid circuit. The flow predictability features of the foregoing can be implemented with a lower cost disposable fluid circuit than one that includes dampers.

As described in the various embodiments, a net flow into or out of a component, such as a dialyzer, filter, or other treatment device or a fluid circuit component, the disclosed embodiments permit the adjustment of a calibration of a pump to achieve a desired ratio of the ingoing and outgoing flows to/from the dialyzer, filter, or other treatment device or a fluid circuit component. As described, the calibration may be performed at predetermined times during a treatment or other type of production operation. Once a pump is recalibrated, the change in the numerical calibration data required to adjust the prediction of the flow rate from the axis speed and pump pressure conditions (inlet and/or outlet pressure) may provide a means for estimating a magnitude of the error in the net flow into or out of the component before the adjustment. This provides an opportunity for the control system to compensate that error based on the estimate, thereby improving the overall control of the system. Even if a pump's calibration data drifts from its prior calibration significantly, it may be possible to sufficiently compensate the consequences of that error that overall net flow into or out of the component, for the entire treatment or other type of production, achieves its target. In extracorporeal blood treatment or peritoneal dialysis treatment, this means the net water removed from, or added to, a patient may be closer to the target. This technique may be performed by any and all of the embodiments disclosed herein.

In embodiments, to use new calibration data and previous calibration data to compensate net inflow/outflow, the controller may adjust the parameters of calibration formula that gives flow volume as a function of suction head and pump speed (RPM). This could represented by, for example, a suitable quadratic surface such as $Q=a\omega(bPi2+cPi)$ or a lookup table that is linearly or curvilinearly interpolated/extrapolated. In an embodiment, the target flow rates may be calculated from the previous and adjusted model and the actual total displaced volume calculated based on the assumption of a linear change in the flow rates over the interval between the calibrations. This effectively determines, based on the assumption of a linear change over time of the actual flow rate versus the flow rate assumed by the model as it was from the last adjustment at the start of the interval. From this, the cumulative error in the net flow into the component or out of the component during the interval can be determined. The future pumping rates may then be adjusted to correct the defect in the cumulative flow such that a target cumulative volume into or out of the component is achieved by the end of the process. In embodiments, the ratio of flow rates of the net inflow pumps and net outflow pumps may be adjusted to take into account the corrected cumulative volume transferred. Note that the adjustment for intervals during which the pumping rate has changed can be done by keeping a record of the flow rate changes over the interval between calibrations and calculating at each change point, the difference in the flow estimated by the assumption of linear progression of the error and the assumed error based on the calibration at the start of the interval. In an embodiment, the cumulative net flow into or out of the component at each calibration during a production period may be calculated based on an assumed linear change (note that the interpolation could have other forms, such as quadratic or any other smooth or non-smooth function, based on theoretical or experimental data) in the flow rate per the corrected model and the assumed flow rate at the time the model was last corrected by calibration. Then, toward the end of the production operation, a single correction operation such as a bolus transfer to or from the component may be performed.

Figure 21:
FIG. 21 shows a graph that illustrates correcting for error in flow balancing in systems such that shown in FIG. 20 and elsewhere herein according to embodiments of the disclosed subject matter.
Figure 21:
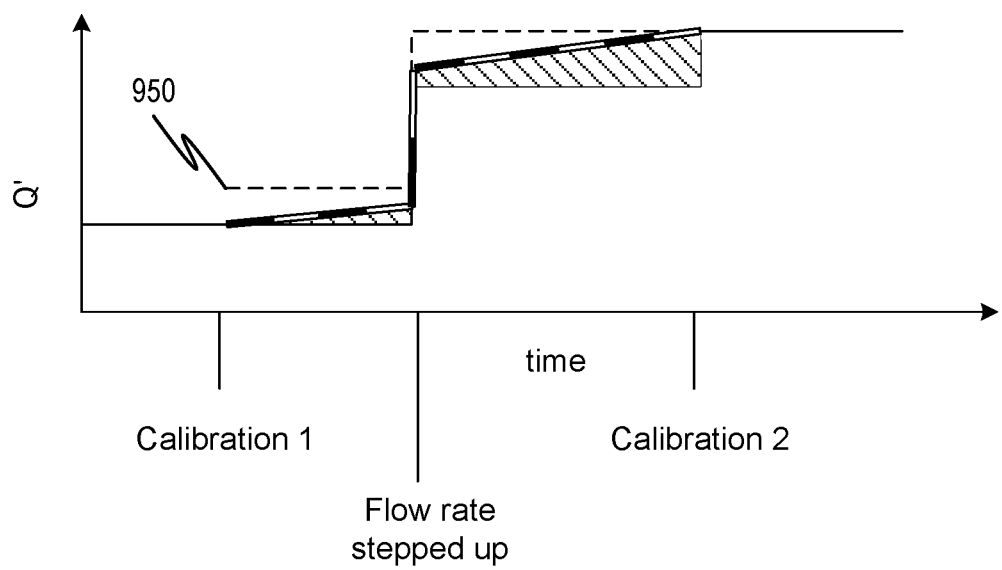

FIG. 21 illustrates the interpolation technique described above in the form of a flow rate vs. time graph for predictions of flow rate based on two calibrated models of flow rate and an interpolated model based on both. Two calibrations are performed during a single operation such as a dialysis treatment at respective points in time. At a point between the calibrations, the flow rate (Q') is stepped up. The lines represent the instantaneous flow rate out of the component (e.g., dialyzer) calculated per the calibration 1, the instantaneous flow rate out of the component (e.g., dialyzer) calculated per the calibration 2, and the instantaneous flow rate out of the component (e.g., dialyzer) according to a linear interpolation representing a corrected instantaneous flow rate. From the interpolated curve, the cumulative error can be calculated as shown by the shaded area. The interpolation may be based on, for example, the linear interpolation of coefficients of a polynomial or other representation of the pump characteristics so the shape need not be straight lines as shown.

Note in all the embodiments in which a change in pressure is measured, or a change in pressure drop, the unsteady pressure change may be derived by various numerical methods from sampled pressure data. An averaging window may be used such as a triangular window or a Gaussian window. The window size may be selected for the particular function. For example for flow synchronization some variability in the averaged pressure may be tolerated. For a stored representation of pressure drop as in the embodiment of FIG. 14, a larger averaging window may be employed to obtain a single pressure or pressure drop representative of a point in time or interval of time.

In the foregoing it was assumed the push pump speed was established and the pull pump speed was determined to match the push pump speed, but it should be clear that in alternative embodiments, the pull pump may be first selected and a matching push pump speed determined in S110. Note also that the calibration procedure may be applied to multiple push pumps in push-pull relation to one or more pull pumps. This increases the dimensionality of the model $Q=f(P_{i,j}, \omega_{pull,i})$ and the combination of pumping speeds to be established but otherwise follows the same operations described above. The model may be formed and calibrated to provide a flow rate that is proportional (approximately equal) to the flow rate of the tandem pump.

Note that in any of the embodiments, the rotor speed of pumps can vary with phase angle and it will be understood that the referenced speed of the embodiments may be understood as an average speed taken over multiple full rotations, RMS rotational velocity, or some other statistic or representation of the rotor's rate.

It should be clear that the methods, devices, and systems for balancing flows are applicable to any type of flow balancing application in which fluid flows are desired to be balanced or proportioned in same manner including medical and non-medical applications.

Although in the examples herein, fluid balancing devices, methods, and systems were described in application to dialysis and extracorporeal blood treatment, the same may also be applied to the balancing of other physiological fluids such as in peritoneal dialysis, apheresis, hemodiafiltration, hemofiltration, hemodialysis, liver dialysis, etc. Also, the principles are applicable to balancing system of any type in which net flow into or out of a component is desired to be maintained, including zero flow.

Figure 8:
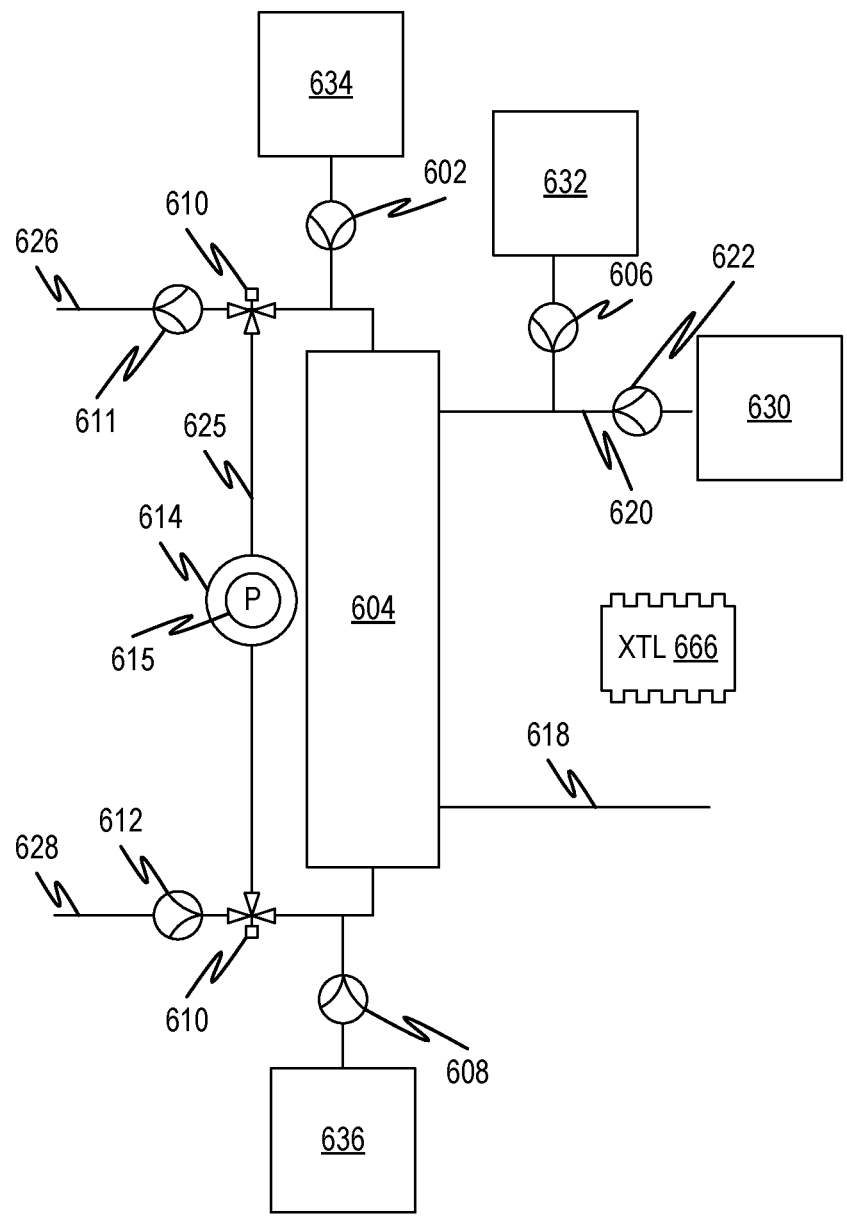
FIG. 8 shows how all the embodiments may be modified such that blood side flow is regulated in order to control transmembrane pressure to create variants of the disclosed subject matter.

Although in the above embodiments, the flow of non-blood fluids is regulated to regulate transmembrane pressure, and thereby convection of fluid across the filter membrane, it is also possible to regulate the blood side flow to achieve a similar result, in embodiments. For example, blood side flow may be regulated by ingoing and outgoing blood pumps whose flow balance may be calibrated and/or confirmed by a common flow meter or pressure sensor as in the above embodiments. FIG. 8 illustrates an example of such a variant. A 502 filter 604 receives blood via blood arterial 626 and venous 628 blood lines. The flow of blood and transmembrane pressure in the filter 604 is regulated by the pumping rates of blood pumps 611 and 612. Blood flow can be selectively diverted through a branch line 625, with an accumulator 614 and pressure sensor 615, by control valves 610 under control of a controller 666. Medicaments 630, 632 such as dialysate, citrate, drugs, or other fluids can flow through line 620 into the blood or the non-blood compartment of filter 604 from the various sources 630 through 636, each at rates determined by respective pumps 606, 608, 622 or directly into the blood from sources 634, 636 for pre and post-dilution of blood under control of pumps 602 and 608 respectively. Various pressure transducers may be positioned in the system to indicate one or both of upstream and downstream pressures in order to permit prediction of the flow rates of the pumps based on shaft speed to be refined. The net fluid balance under all conditions can be maintained by regulating the pumping rates of the blood pumps 611 and 612 because there is only one non-blood side pump thereby allowing transmembrane pressure to be mediated by the blood side. The pumping rates of non-blood fluids can be predictive as disclosed above.

In the same or additional embodiments, the active accumulator can be used with pressure sensing as in the fixed accumulator embodiments. However the volume can be adjusted to compensate for the overall flow rate through the branch channel thereby making the rate of net flow into or out of the accumulator more for synchronizing at different flow rates similar. So when synchronizing pumps flowing at low flow rates, the accumulator volume may be low. When synchronizing pumps flowing at high flow rates, the accumulator volume may be adjusted to be higher.

As described, in any of the foregoing embodiments, the indication of flow difference between balancing pumps may be indicated by a flow or pressure signal during a calibration (or balance confirmation) flow configuration and procedure. For example, pressure rise or fall may be detected when flow runs through a branch line. It is desirable to make the detection of the flow synchronization as rapid as possible. However, minor variations in the pumping flow rates or pressures are overlayed on the average flow or pressure due to inherent pulsing of certain types of pumps, for example peristaltic pumps. This effect is exacerbated when multiple pumps are operating in series, both of which can affect the flow or pressure. The worst level of interference is when the pumps are operating at close to the same speed and in a pressure- or flow-reinforcing phase relationship. The resulting beats can cause an enhancement of the sample bias resulting from a limited detection interval. For example if the pressure is sampled over only a fraction of a beat, one of the other of the pressure peaks (mutually reinforcing cycles) or troughs (mutually destructive cycles) may contribute disproportionately to the average signal. This can occur even when an average is taken over multiple beats, where the number of beats is small, for example, less than 5. Of course a very long sampling interval can avoid this problem, but it is preferred to achieve an accurate pressure indication in a short time.

In the various embodiments, the branch channel leads to a drain. Fluid otherwise directed to a dialyzer or hemofilter or other treatment device can be selectively diverted through the branch channel to the drain for other reasons besides the pump synchronization, providing a double function. For example, if a fluid anomaly such as temperature or air is detecting in the fluid heading for the dialyzer, it could be diverted until the anomaly clears. This may facilitate priming of the dialysate side of the dialyzer.

In the various embodiments, two pumps are used for flowing dialysate into and out of the dialyzer (or equivalent for other types of treatment devices). The pumps may operate in either direction. This allows priming to be performed on the blood and dialysate sides of the treatment circuit at the same time. According to embodiments, the two dialysate pumps include an inflow pump and an outflow pump, two outflow pumps, or two inflow pumps, depending on the controller's selection of speed and rotational direction (so either pump could play either role). In embodiments, priming may be done by pumping dialysate such that the pump rate out of the filter is lower than the pump rate in to the filter or both pumps may be operated in an outflow mode such that the net rate into the filter is such that dialysate is forced through the membrane into the blood circuit. In other embodiments, fluid can be drawn from a fluid source connected to the blood circuit by dialysate pumps that pull fluid through the membrane into the dialysate side, thereby, again, priming both sides of the circuit. In this latter embodiment, the inflow and outflow pumps may operate to different rates to generate a net flow from the blood side to the dialysate side or both pumps may operate in an outflow mode.

In all the various embodiments, a valve can be provided in the spent dialysate path to return fluid that is used for synchronization to a recovery channel where it may be used for treatment rather than wasted. A vessel may be used to hold recovered dialysate in online dialysate systems or recovered dialysate may be flowed into a container for bagged dialysate setups.

To mitigate the sample bias that attends operating multiple pumps such that they mutually interfere to reinforce or cancel pressure fluctuations, any of the embodiments may include the additional features as follows.

1. The pump tube segments of the respective pumps (or pumping tube segments as appropriate for the type of pump embodiment) that contribute to the pressure in the accumulator may be chosen to have different diameters selected to ensure that the pressure pulse rates they contribute are substantially non-synchronous over the range of predicted flow rates. For example, the pressure pulses of one pump, at a worst case condition, may be at least 2 times that of any other. Alternatively another predefined multiple may be used (other than 2). As a consequence, pumps that operate at similar flow rates, different tubing diameters of peristaltic pumps would require one pump rotor to turn at a different rate than the other thereby avoiding the reinforcing effect.
2. For peristaltic pumps, the numbers of rollers of peristaltic pumps may be selected such that the reinforcing effect is reduced. For example, the dialysate pumps (or blood pumps of FIG. 8) may have different numbers of rotors, since these pumps pump fluid at close flow rates. Obviously pumps that operate normally at very different rates do not produce the reinforcing effects if the number of rollers or tubing diameters are similar so the requirement may be to choose tubing diameters and roller numbers to ensure the reinforcing effect is minimized, or more broadly stated, choosing number of rollers and/or pump tubing segment diameters responsively to the pulsing rate of the respective pumps. A configuration may be provided such that the pressure pulses of one pump, at a worst case condition, are at least 2 times that of any other as a result of one or both of the number of rollers and/or the diameter of the respective pump tubing segments. Alternatively another predefined multiple may be used (other than 2).
3. The controller may be programmed to select operating conditions that avoid the sample bias effect. Thus, in programming the controller, the operating states associated with the condition of excess sample bias may be predicted and stored in the controller. Alternatively, a numerical model of the system may be stored in the controller that predicts the sample bias or data responsive to the sample bias with an optimization algorithm that seeks an operating state that has the largest pressure pulse rate difference for those pumps contributing to pressure in the accumulator (e.g. 412). The goal state of such an optimization algorithm may simply be vectors representing a predefined range of the multiple and the targeted flow rates of the respective pumps. To support the controllers freedom to select a flow rates according to treatment operation requirements while still avoiding operating states with high sample bias, one or more pumps or flow channels can have selectable flow restrictors or peristaltic pump occlusion to selectively change the volumetric efficiency of the pumps whereby the relationship between RPM and flow rate for a given suction pressure head is changed making the volumetric efficiency of one pump different from the other (i.e., volume displaced per revolution).
4. In any of the foregoing embodiments, the pumps may have a fixed ratio of pressure pulses, for example by attaching the pump rotors to a common shaft, while managing the pumping rates by regulating an active flow restrictor upstream or downstream of one or more of the pumps in order to control the relative flow rates of the pumps. The fixed ratio may be selected at design time and it may remain constant for all operating conditions, according to this scheme.
5. The same scheme as number 4 may be implemented using active control to ensure a predefined ratio of rotor speeds rather than a mechanical interconnect between the rotors.
6. In any of the embodiments, the pumps in a push-pull arrangement may be run at rates that produce identical flow pulse frequencies while still adjusting the net flow rate into the branch channel (accumulator and branch line) changing the volumetric efficiency of one of the pumps by restricting flow upstream of one of the pumps. This allows the flow rates to be synchronized while maintaining identical flow rates of the two pumps. This can be done with separate pumps controlled to run at the same pulse frequency or by mechanically interconnected pump rotors (See FIGS. 12A, 12B, and 13 and related discussion, for example). Preferably the down-regulated pump experiences an increased flow restriction at its inlet since peristaltic pumps are more readily and precisely regulated by upstream flow restriction.

7. In the scheme of 6, the pumps may be operated so that they remain in precisely a phase difference such that their flow pulsations are mutually canceling, with the pulling pump drawing at the same time as the pushing pump is pushing and with both pumps constricted at the same times. In this way the pulsations in the branch channel are minimized.
8. Each time a calibration is done, it can be done at one or more different inlet and, optionally, outlet, pressure conditions that cover the ranges of variability that the system may experience due to manufacturing variability, setup variability, mechanical changes in the hardware components, and any factors that may cause differences in the inlet and outlet pressures or causative flow restrictions experienced by the pumps. The different pressure conditions can be created by flow restrictions in combination with the selection of pump speed using features as discussed herein.

The accuracy of the pump calibration/synchronization procedures and systems described herein can be undermined by variability or faults in disposable parts and the proper mechanical operation of the machinery. For poor engagement of a pumping tube segment in a peristaltic pump may cause a lack of repeatability or unreliable operation of the pump. To ensure the integrity and accuracy of the procedures and devices supporting synchronization, various devices and methods may be employed alone or in combination with any of the embodiments. Any of these indications can be used to halt operation or to generate an alarm using the system controller of any of the embodiments. The following are examples.

1. Measuring pressure at various points along the circuit to detect anomalous pressure changes indicating occlusion of a line.
2. Measuring pressure into and/or out of pumps to detect improper pump function.
3. Pressure on peristaltic pump shoe, for example by means of one or more strain gauges, the force exerted through the pump tube segment by the rotor can generate a force temporal pattern or average that may indicate incorrect setup or some other problem with the pump.
4. Acoustic or vibration detection on the pump or any of the tubing segments may be used to indicate an anomalous operation or misconfiguration.
5. One of the pumps to which other pumps or combinations are slaved by the synchronization calibration procedures may be tested for flow calibration using an independent flow measurement such as time-of-flight of a label such as temperature, composition property such as salinity, or air. See examples of this type of flow measurement in US Patent Publication 20150005699.
6. The same as 5 but applied to all the pumps to determine whether any are out of bounds.
7. Air detection at any points in the fluid circuit where air should not be present.
8. Position encoders on all control valve actuators to ensure full range of motion and speed of operation.
9. Force detection for control valves using a strain gauge on the actuators driving valve pinching elements.
10. Position encoding to detect full engagement of disposable with pump and valve actuators.
11. External leak detectors such as water detection or resistivity sensors so that water leaking from engaged tubing sets will be detected.
12. Using the same sensor in a funnel configuration to detect blood leaks as well as non-blood fluid leaks.
13. Temperature sensors in the fluid circuit to detect temperature anomaly.
14. During priming, the blood pump may be run to force priming fluid through a dialyzer into the treatment fluid circuit. Pressure sensors in the treatment fluid circuit may detect, and thereby verify, the connections of the treatment fluid to the dialyzer thereby.

Note that in any of the embodiments, where a flow meter is used to determine the flow rate, a precise flow restrictor with upstream and downstream pressure sensors, or a pressure differential sensor across the segment, may be used to measure the flow rate. Such a device, as is known, for given fluid properties, can be used to measure flow rate. In the present application, such a device may allow flow to be measure in an inexpensive disposable so a novel benefit may arise. The synchronization of any of the method or system embodiments may be accomplished without the use of an accumulator by programming the controller to flow each pump in turn through the flow restrictor, measuring the flow, and then switching in another pump. This may be done for multiple flow rates.

Note that in any and all embodiments, instead of the controller regulating the flow by changing the pump rotor speed, selectable flow restrictors or recirculation channels may be used with a fixed pump rotor speed to selectively regulate flow. Such variations may help to mitigate the pulse reinforcement effect described immediately above. In embodiments, the pumps may be operated such as to permit the phase relationship to be controlled by the controller or mechanically-fixed (e.g., pump rotors on the same shaft). Where the pumps are controlled to run at the same speed, with flow rate regulated by controlling the inlet or outlet pressure (i.e., pump head) or by using a selectable bypass rate, the pressure or flow pulses can be regulated by adjusting the phase such that the pressure or flow pulses cancel at the point of measurement.

In any of the embodiments, a virtual pressure-based synchronization can be performed. In the embodiments, the flow sync system pump rates are adjusted to match by detecting pressure in a branch channel. In alternatives, the flow synchronization operation is performed but neither pumping rate is slewed. Rather the rate of change of the pressure (or volume of the active accumulator is detected and used to make numerical compensation to the commanded pumping rates.

In any of the embodiments, virtual pressure compensation may be performed. In most embodiments, pressure-dependent gains are applied to adjust pumping rates to compensate changes in inlet pressure. As an alternative, the same pressure signals can merely be tracked/recorded, and used to make periodic adjustments to relevant pump rates at discrete intervals. The cumulative effect of pump inlet pressure changes over a prescribed period of time can be accumulated to calculate a "net volume error" for that time interval; rates for the next time interval can be adjusted to compensate for the previous interval's net pressure-based error.

Note that in any of the embodiments, the passive accumulators may be replaced with active device with a controllable interior volume. The controller is programmed to seek and establish a predefined pressure in the accumulator when the system is configured for synchronization, i.e., the pumps are connected through the accumulator to test their pumping relationship. The predefined pressure may be chosen to minimize the pressure change experienced by each when the treatment/synchronization switchover occurs. The active accumulator pressure regulation may be accomplished by means of a separate pump in communication with the accumulator or by controlling one or both of the pumps being synched. FIG. 9 shows an example of an active accumulator 745.

In any of the foregoing embodiments, the controller may be configured to perform the synchronization at multiple pressure set points (pressure conditions at the inlets and outlets of the connected pumps) in order to generate a dynamic pressure calibration curve that represents synchronized conditions at multiple pressure conditions. This is discussed above in embodiments, but it should be clear that the feature is applicable to any of the embodiments.

The synchronization process can be triggered, within a treatment cycle, on a predefined chronological schedule (every 15 minutes during treatment, for example) or upon the displacement of a calculated volume of medicament (e.g. dialysate) or blood. Other trigger events are also possible.
1. The number of rotations of a pump actuator exceeds a predefined value;
2. A change in fluid temperature or ambient temperature beyond a predefined magnitude; and
3. A change in pressure at any, or one or more predefined points in the system or a pressure differential at any point in the fluid circuit.

In any of the embodiments, the controller may be configured to recalculate or update the total accumulated ultrafiltrate of a treatment cycle based on the changes in calibration generated from the synching process.

In any of the embodiments, when a synchronization is done, one of the pumps may be identified as a master pump (one whose predicted pumping rate is identified as true or accurate). In embodiments, the controller may subject that master pump to an additional test in order to resets its individual calibration by independently measuring flow against one or more flow rate conditions. The resulting calibration data may be used to adjust the prediction models for the master pump as well as the pump with which it was, or is going to be, synchronized. The independent measure of flow rate may be obtained using time of flight of a fluid label such as air bubbles injected and detected ultrasonically or a temperature label. An accurate flow meter may be used. Further fluid circuit tests may be also be done to ensure the accuracy of the synchronization process, for example, a pump occlusion test may be done to ensure a predicted pressure rise occurs when a pump flow if blocked, line leaks may be detected, pressures in and out of the pump match stored predefined values, for example.

In any of the embodiments, an active accumulator may be used to change the total volume of the branch line that bypasses the device to be balanced (e.g., a treatment device, dialyzer or any of the devices identified with the described embodiments in which a controlled inflow and outflow ratio is targeted), so that the rate of increase of pressure due to the net inflow of fluid into the branch line and accumulator (total branch volume) together provides for rapid matching of the flows into and out of the branch line and stability of the control parameters used for matching. In an embodiment, a digital proportional-integral-derivative control (PID control) method may be implemented on the relevant controller.

In any of the embodiments, an accumulator may not need to be provided as a separate element in that natural compliance of the present fluid circuit may be sufficient to allow calibration (synchronization) of the inflow and outflow pumps.

In any of the embodiments, including the claims, the calibration flow used for pump synchronization can be established in a same portion of the fluid circuit as used during treatment and thus flow does not necessarily need to be diverted during calibration. For example, pinch clamps could be used to halt the flow of blood during calibration, including flow synchronization of the pumps, such that flow from the pumps governing flow into and out of a dialyzer (or blood treatment device, hemofilter, patient interface or other terms equivalent to the dialyzer in terms of the calibration requirement) exists in a fixed volume channel. As such, the pressure in the channel is determined by any difference in the flow rate thereby permitting synchronization and calibration in a simpler arrangement. Similarly, the flow of non-blood fluid such as dialysate can be pinched off (forming a direct channel between the two blood pumps (Such as the FIG. 8 embodiment) such that they can then be synchronized through the dialyzer. This eliminates the need for branch line 625. Again as elsewhere the accumulator 614 would not necessarily be needed.

According to first embodiments, the disclosed subject matter includes a medical treatment system. A first fluid management element pumps fluid from a patient interface device during a treatment. A second fluid management element pumps fluid into a patient interface device during a treatment. A controller is connected to at least one of the first and second fluid management elements and has a processor programmed to regulate a rate of flow to or from the patient in order to achieve a predefined net removal of fluid from the patient during a therapeutic treatment implemented under control of the controller. A fluid circuit switch allows a flow from the at least one of the first and second fluid management elements to be selectively and automatically configured under control of the controller between a therapy configuration for delivering said therapeutic treatment to a calibration configuration in which flow through said at least one of the first and second fluid management elements is temporarily diverted to a flow or pressure sensor that outputs a signal indicating a difference between the flow rates of the first and second fluid management elements that occurs during a treatment. The controller is programmed to calculate and store flow correction data representing a correction to be applied to a rate of flow of said at least one of the first and second fluid management elements responsively to said signal. The controller is further programmed to modify a flow rate of said at least one of the first and second fluid management elements responsively to said flow correction data.

The first embodiments may be modified to form additional first embodiments in which a diverted flow in the calibration configuration flows between the first and second fluid management elements through a fluid accumulator connected to a pressure sensor that outputs said signal. The first embodiments may be modified to form additional first embodiments in which an accumulator is configured such that pressure increases as fluid fills said accumulator, whereby a difference in the flow rates of said first and second fluid management elements results in an increasing or decreasing pressure.

The first embodiments may be modified to form additional first embodiments in which the accumulator has a residual volume of fluid to permit the measurement of a pressure change caused by a net removal or a net addition of fluid from or to said accumulator. The first embodiments may be modified to form additional first embodiments in which the first fluid management elements include a peristaltic pump. The first embodiments may be modified to form additional first embodiments in which the fluid circuit includes a disposable plastic tubing set and at least one control valve. Here and in any of the embodiments, the at least one control valve (or any control valve) can be made of lengths of tubing of the disposable plastic tubing set, which lengths are joined by at least one junction, such as a T junction or a Y junction, or a H, or 4-way crossing junction. Any kind of junction may be used. The tubing lengths are engageable with pinch clamps that selectively seal the tubing lengths under control of a controller. The pinch clamps may be permanent reusable elements of a system that pinch respective portions of the tubing set to selectively form different flow paths.

The first embodiments may be modified to form additional first embodiments that include a third fluid management element that pumps fluid into the patient during a treatment, the third fluid management element being coupled to a synchronization mechanism that causes the first and third fluid management elements to pump equal amounts of fluid per unit time during a treatment. The first embodiments may be modified to form additional first embodiments that include a third fluid management element that pumps fluid into the patient during a treatment, the third fluid management element being coupled to a mechanical synchronization mechanism that causes the first and third fluid management elements to move in mechanical synchrony such that they pump equal amounts of fluid per unit time during a treatment through the fluid circuit.

The first embodiments may be modified to form additional first embodiments that include a blood circuit connected to the fluid circuit by a membrane. The first embodiments may be modified to form additional first embodiments in which the flow or pressure sensor is a flow sensor. The first embodiments may be modified to form additional first embodiments that include a blood circuit connected to the fluid circuit by a membrane and wherein a diverted flow in the calibration configuration flows through a flow path between the first and second fluid management elements through a fluid accumulator connected to a pressure sensor that outputs said signal, wherein the membrane is separated from the flow path. The first embodiments may be modified to form additional first embodiments in which the second fluid management element is connected to a source of a medicament.

The first embodiments may be modified to form additional first embodiments in which the controller is connected to a user interface and programmed to accept and store ultrafiltration data representing a target net ultrafiltration, wherein the controller is further programmed to control flow through said at least said one of said first and second fluid management elements responsively to said ultrafiltration data.

According to second embodiments, the disclosed subject matter includes medical treatment system. A first pump pumps fluid from a patient interface device during a treatment. A second pump that pumps fluid into a patient interface device during a treatment. A controller is connected to at least one of the first and second pumps and has a processor programmed to regulate a rate of flow to or from the patient in order to achieve a predefined net removal of fluid from the patient during a therapeutic treatment implemented under control of the controller. A fluid circuit switch allows a flow from the at least one of the first and second pumps to be selectively and automatically configured under control of the controller between a therapy configuration for delivering said therapeutic treatment to a calibration configuration in which flow through said at least one of the first and second pumps is temporarily diverted to a flow or pressure sensor that outputs a signal indicating a difference between the flow rates of the first and second pumps. This may be done during treatment, during priming, or during calibration operations or testing. The controller is programmed to calculate and store flow correction data representing a correction to be applied to a rate of flow of said at least one of the first and second pumps responsively to said signal. The controller is further programmed to modify a flow rate of said at least one of the first and second pumps responsively to said flow correction data.

The second embodiments may be modified to form additional second embodiments in which a diverted flow in the calibration configuration flows between the first and second pumps through a fluid accumulator connected to a pressure sensor that outputs said signal.

The second embodiments may be modified to form additional second embodiments in which an accumulator is configured such that pressure increases as fluid fills said accumulator, whereby a difference in the flow rates of said first and second pumps results in an increasing or decreasing pressure. The second embodiments may be modified to form additional second embodiments in which the accumulator has a residual volume of fluid to permit the measurement of a pressure change caused by a net removal or a net addition of fluid from or to said accumulator. The second embodiments may be modified to form additional second embodiments in which the first pumps include a peristaltic pump.

The second embodiments may be modified to form additional second embodiments in which the fluid circuit includes a disposable plastic tubing set and at least one control valve. Here and in any of the embodiments, the at least one control valve (or any control valve) can be made of lengths of tubing of the disposable plastic tubing set, which lengths are joined by at least one junction, such as a T junction or a Y junction, or a H, or 4-way crossing junction. Any kind of junction may be used. The tubing lengths are engageable with pinch clamps that selectively seal the tubing lengths under control of a controller. The pinch clamps may be permanent reusable elements of a system that pinch respective portions of the tubing set to selectively form different flow paths.

The second embodiments may be modified to form additional second embodiments that include a third pump that pumps fluid into the patient during a treatment, the third pump being coupled to a synchronization mechanism that causes the first and third pumps to pump equal amounts of fluid per unit time during a treatment.

The second embodiments may be modified to form additional second embodiments that include a third pump that pumps fluid into the patient during a treatment, the third pump being coupled to a mechanical synchronization mechanism that causes the first and third pumps to move in mechanical synchrony such that they pump equal amounts of fluid per unit time during a treatment through the fluid circuit. The second embodiments may be modified to form additional second embodiments that include a blood circuit connected to the fluid circuit by a membrane. The second embodiments may be modified to form additional second embodiments in which the flow or pressure sensor is a flow sensor.

The second embodiments may be modified to form additional second embodiments that include a blood circuit connected to the fluid circuit by a membrane and wherein a diverted flow in the calibration configuration flows through a flow path between the first and second pumps through a fluid accumulator connected to a pressure sensor that outputs said signal, wherein the membrane is separated from the flow path. The second embodiments may be modified to form additional second embodiments in which the second pump is connected to a source of a medicament. The second embodiments may be modified to form additional second embodiments in which the controller is connected to a user interface and programmed to accept and store ultrafiltration data representing a target net ultrafiltration, wherein the controller is further programmed to control flow through said at least said one of said first and second pumps responsively to said ultrafiltration data.

According to third embodiments, the disclosed subject matter includes a medical treatment system with a controller and control valve actuators and first and second pumps, the control valve actuators and pumps is controlled by the controller. The first pump is controlled to regulate flow toward a patient interface device and the second pump is controlled to regulate flow from the same patient interface device. The patient interface device is a device that is separate from the claimed treatment system that interfaces with a patient fluid compartment includes at least one of a dialyzer, a hemofilter, a hemodiafilter, an ultrafilter, and a plasmapheresis device. The controller includes a processor programmed to regulate the speed of the first and second pumps to achieve a predefined net removal of fluid from the patient interface device during a treatment interval. The processor is further programmed to control the control valve actuators to switch between a first position that configures a fluid circuit, when attached to the control valves, in a bypass configuration which defines a bypass flow path that bypasses the patient interface device, and a second position which defines a flow path into and out of the patient interface device. A pressure transducer is connected to convey pressure signals to the controller, the pressure signals indicating pressure in the bypass flow path. the controller is programmed to calculate and store flow correction data representing a correction to be applied to a rate of flow of the at least one of the first and second fluid management elements responsively to the signal. The controller is further programmed to modify a flow rate of the at least one of the first and second fluid management elements responsively to the flow correction data.

The third embodiments can be modified to form additional third embodiments in which a diverted flow in the calibration configuration flows between the first and second fluid management elements through a fluid accumulator connected to a pressure sensor that outputs the signal. The third embodiments can be modified to form additional third embodiments in which the accumulator is configured such that pressure increases as fluid fills the accumulator, whereby a difference in the flow rates of the first and second fluid management elements results in an increasing or decreasing pressure. The third embodiments can be modified to form additional third embodiments in which the accumulator has a residual volume of fluid to permit the measurement of a pressure change caused by a net removal or a net addition of fluid from or to the accumulator. The third embodiments can be modified to form additional third embodiments in which the first fluid management element includes a peristaltic pump. The third embodiments can be modified to form additional third embodiments in which the fluid circuit includes a disposable plastic tubing set and at least one control valve, the control valve includes a tubing junction that interfaces with one or more pinch clamps to form selectable flow paths, the pinch clamps is permanent reusable elements that pinch respective portions of the tubing set. The third embodiments can be modified to form additional third embodiments in which a third fluid management element pumps fluid into the patient interface device during a treatment, the third fluid management element is coupled to a synchronization mechanism that causes the first and third fluid management elements to pump equal amounts of fluid per unit time during a treatment.

The third embodiments can be modified to form additional third embodiments in which a third fluid management element pumps fluid into the patient interface device during a treatment, the third fluid management element is coupled to a mechanical synchronization mechanism that causes the first and third fluid management elements to move such that they pump equal amounts of fluid per unit time during a treatment through the fluid circuit. The third embodiments can be modified to form additional third embodiments in which a blood circuit interfaces with the patient interface device and, through the latter, to the fluid circuit. The third embodiments can be modified to form additional third embodiments in which the flow or pressure sensor is a flow sensor. The third embodiments can be modified to form additional third embodiments in which a blood circuit interfaces with the patient interface device and, through the latter, to the fluid circuit and wherein a diverted flow in the calibration configuration flows through a flow path between the first and second fluid management elements through a fluid accumulator connected to a pressure sensor that outputs the signal, wherein a fluid circuit portion connected to the patient interface device is separate from the flow path. The third embodiments can be modified to form additional third embodiments in which the second fluid management element is connected to a source of a medicament. The third embodiments can be modified to form additional third embodiments in which the controller is connected to a user interface and programmed to accept and store ultrafiltration data representing a target net ultrafiltration, wherein the controller is further programmed to control flow through the at least the one of the first and second fluid management elements responsively to the ultrafiltration data.

According to fourth embodiments, the disclosed subject matter includes a method of regulating the balanced flow of fluids with in a system has first and second fluid channels each with at least one respective pump for each of the first and second fluid channels. The method includes using a controller to control the rate of pumping of one or more of the respective pumps to establish flows in the first and second channels of equal volume flow rate based on calibration data stored in the controller. The first and second channels connect to a fluid handling device in which a ratio of flow rates of entering and leaving flows to and from the fluid handling device is maintained by the controller. The method further includes using the controller, temporarily establishing a flow from the first channel to the second channel through a test flow branch with a pressure sensor and receiving a signal of a test branch pressure in the test branch at the controller. The method further includes, in response to the test branch pressure signal, using the controller, adjusting the calibration data. thereafter, using the controller, adjusting one or more of the respective pumps according to the calibration data adjusted by the adjusting.

The fourth embodiments can be modified to form additional fourth embodiments in which the controller receives a local pressure upstream and/or downstream of at least one of the respective pumps, the adjusting being responsive to both the test branch pressure signal and the local pressure signal. The fourth embodiments can be modified to form additional fourth embodiments in which the receiving a local pressure includes receiving local pressures upstream and downstream of the at least one of the respective pumps. The fourth embodiments can be modified to form additional fourth embodiments in which the controller controls a valve that selectively permits flow through the test flow branch and the controller automatically selects a time of the temporarily establishing. The fourth embodiments can be modified to form additional fourth embodiments in which the controller controls a valve that selectively permits flow through the test flow branch and the controller automatically selects multiple instances of the temporarily establishing. The fourth embodiments can be modified to form additional fourth embodiments in which the fluid handling device is a blood treatment device. The fourth embodiments can be modified to form additional fourth embodiments in which the blood treatment device is a dialyzer or a hemofilter and replacement fluid source. The fourth embodiments can be modified to form additional fourth embodiments in which the respective pumps are peristaltic pumps. The fourth embodiments can be modified to form additional fourth embodiments in which the respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing. The fourth embodiments can be modified to form additional fourth embodiments in which the respective pumps are peristaltic pumps and pumping tube segments of no one of the respective pumps responsible for the entering flow has an inner diameter the same as a pumping tube segment inner diameter of a one of the respective pumps responsible for the leaving flow. The fourth embodiments can be modified to form additional fourth embodiments in which the respective pumps are peristaltic pumps and the number of rollers for no one of the respective pumps responsible for the entering flow is the same as the number of rollers of a one of the respective pumps responsible for the leaving flow. The fourth embodiments can be modified to form additional fourth embodiments in which the controller stores data representing operating conditions that coincide with respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing.

According to fifth embodiments, the disclosed subject matter includes a method of maintaining a predefined ratio of flow rates in first and second channels with connecting the first and second channels temporarily to create a continuous flow between them. The method includes measuring a static pressure of a channel carrying the continuous flow temporarily generated in the connecting. The method further includes adjusting calibration data of one or more respective pumps that generate at least one of the second flows responsively to a result of the measuring.

The fifth embodiments can be modified to form additional fifth embodiments in which the connecting, measuring, and adjusting are done automatically by a programmable controller, the method further comprising adjusting a speed of the one or more respective pumps in response to the calibration data. The fifth embodiments can be modified to form additional fifth embodiments including limiting low frequency pressure fluctuations in the continuous flow. The fifth embodiments can be modified to form additional fifth embodiments in which the limiting includes selecting the one or more respective pumps whose pulsation frequencies at a rate of the continuous flow produce beats due to superposition of the pulsations that are either multiple times shorter than, or multiple times longer than a period of the measuring, the measuring includes sampling the static pressure multiple times over the period of the measuring. The fifth embodiments can be modified to form additional fifth embodiments in which the limiting includes adjusting the one or more respective pumps to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies. The fifth embodiments can be modified to form additional fifth embodiments in which the one or more respective pumps have different ratios as a result of has differences in one or a combination of tubing inner diameter or number of rollers of a peristaltic pump rotor. The fifth embodiments can be modified to form additional fifth embodiments in which one or both of the first and second channels includes at least two fluid lines. The fifth embodiments can be modified to form additional fifth embodiments in which the connecting, measuring, and adjusting are done automatically by a programmable controller, the method further comprising adjusting a speed of the one or more respective pumps in response to the calibration data. The fifth embodiments can be modified to form additional fifth embodiments further including limiting low frequency pressure fluctuations in the continuous flow. The fifth embodiments can be modified to form additional fifth embodiments in which the limiting includes selecting the one or more respective pumps whose pulsation frequencies at a rate of the continuous flow produce beats due to superposition of the pulsations that are either multiple times shorter than, or multiple times longer than a period of the measuring, the measuring includes sampling the static pressure multiple times over the period of the measuring. The fifth embodiments can be modified to form additional fifth embodiments in which the limiting includes adjusting the one or more respective pumps to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies. The fifth embodiments can be modified to form additional fifth embodiments in which the one or more respective pumps have different ratios as a result of has differences in one or a combination of tubing inner diameter, suction side head pressure, or number of rollers of a respective peristaltic pump rotor. The fifth embodiments can be modified to form additional fifth embodiments in which the first and second flow channels are, at times other than the measuring, connected by a controller to a medical treatment device for the supply and withdrawal of treatment fluid. The fifth embodiments can be modified to form additional fifth embodiments in which the medical treatment device includes a renal replacement therapy system and the treatment fluid includes dialysate or electrolyte.

According to sixth embodiments, the disclosed subject matter includes a system for regulating the balanced flow of fluids with first and second fluid channels each with at least one respective pump for each of the first and second fluid channels. A controller is connected to the respective pumps to control the rate of pumping of one or more of the respective pumps. The controller is connected to one or more valves to permit it to establish flows in the first and second channels of equal volume flow rate responsively to calibration data stored in the controller. The first and second channels connect to a fluid handling device in which a ratio of flow rates of entering and leaving flows to and from the fluid handling device is maintained by the controller. the controller, at selected times, temporarily establishing a flow from the first channel to the second channel through a test flow branch, connected through the one or more valves, with a pressure sensor and sampling a signal of a test branch pressure in the test branch at the controller. In response to the samples, the controller adjusts the calibration data stored in the controller. the controller, using the adjusted calibration data stored in the controller to adjust the one or more of the respective pumps.

The sixth embodiments can be modified to form additional sixth embodiments in which the controller is connected to receive a local pressure upstream and/or downstream of at least one of the respective pumps, the adjusting is responsive to both the test branch pressure signal and the local pressure signal. The sixth embodiments can be modified to form additional sixth embodiments in which the received local pressure includes local pressures upstream and downstream of the at least one of the respective pumps. The sixth embodiments can be modified to form additional sixth embodiments in which the controller controls a valve that selectively permits flow through the test flow branch and the controller automatically selects a time of establishing the continuous flow and performing the sampling. The sixth embodiments can be modified to form additional sixth embodiments in which the controller controls a valve that selectively permits flow through the test flow branch and the controller automatically iteratively establishes the continuous flow and the performance of the sampling. The sixth embodiments can be modified to form additional sixth embodiments in which the fluid handling device is a blood treatment device. The sixth embodiments can be modified to form additional sixth embodiments in which the blood treatment device is a dialyzer or a hemofilter and replacement fluid source. The sixth embodiments can be modified to form additional sixth embodiments in which the respective pumps are peristaltic pumps. The sixth embodiments can be modified to form additional sixth embodiments in which the respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing. The sixth embodiments can be modified to form additional sixth embodiments in which the respective pumps are peristaltic pumps and pumping tube segments of no one of the respective pumps responsible for the entering flow has an inner diameter the same as a pumping tube segment inner diameter of a one of the respective pumps responsible for the leaving flow. The sixth embodiments can be modified to form additional sixth embodiments in which the respective pumps are peristaltic pumps and the number of rollers for no one of the respective pumps responsible for the entering flow is the same as the number of rollers of a one of the respective pumps responsible for the leaving flow. The sixth embodiments can be modified to form additional sixth embodiments in which the controller stores data representing operating conditions that coincide with respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing.

According to seventh embodiments, the disclosed subject matter includes a method for maintaining a predefined ratio of flow rates in first and second channels. The method includes connecting the first and second channels temporarily to create a continuous flow between them. The method further includes measuring a static pressure of a channel carrying the continuous flow temporarily generated in the connecting. adjusting calibration data of one or more respective pumps that generate at least one of the second flows responsively to a result of the measuring.

The seventh embodiments can be modified to form additional seventh embodiments in which the connecting, measuring, and adjusting are done automatically by a programmable controller, the system further comprising adjusting a speed of the one or more respective pumps in response to the calibration data. The seventh embodiments can be modified to form additional seventh embodiments in which the first and second flow channels and/or the test branch and/or the one at least one respective pump are configured to limit low frequency pressure fluctuations in the continuous flow due to the superposition of pressure pulses of the respective pumps that form beats. The seventh embodiments can be modified to form additional seventh embodiments in which the one or more respective pumps have pulsation frequencies at a rate of the continuous flow that produces beats due to superposition of the pulsations that are either multiple times shorter than, or multiple times longer than a period of the measuring, the measuring includes sampling the static pressure multiple times over the period of the measuring. The seventh embodiments can be modified to form additional seventh embodiments in which the one or more respective pumps are controlled to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies. The seventh embodiments can be modified to form additional seventh embodiments in which the one or more respective pumps have different ratios as a result of has differences in one or a combination of tubing inner diameter or number of rollers of a peristaltic pump rotor. The seventh embodiments can be modified to form additional seventh embodiments in which one or both of the first and second channels includes at least two fluid lines. The seventh embodiments can be modified to form additional seventh embodiments in which the connecting, measuring, and adjusting are done automatically by a programmable controller, the system further comprising adjusting a speed of the one or more respective pumps in response to the calibration data. The seventh embodiments can be modified to form additional seventh embodiments in which the first and second flow channels and/or the test branch and/or the one at least one respective pump are configured to limit low frequency pressure fluctuations in the continuous flow due to the superposition of pressure pulses of the respective pumps that form beats. The seventh embodiments can be modified to form additional seventh embodiments in which the one or more respective pumps have pulsation frequencies at a rate of the continuous flow that produces beats due to superposition of the pulsations that are either multiple times shorter than, or multiple times longer than a period of the measuring, the measuring includes sampling the static pressure multiple times over the period of the measuring. The seventh embodiments can be modified to form additional seventh embodiments in which the one or more respective pumps are controlled to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies. The seventh embodiments can be modified to form additional seventh embodiments in which the one or more respective pumps have different ratios as a result of has differences in one or a combination of tubing inner diameter or number of rollers of a peristaltic pump rotor. The seventh embodiments can be modified to form additional seventh embodiments in which the first and second flow channels are, at times other than at times that the continuous flow is established by the controller, connected by the controller to a medical treatment device for the supply and withdrawal of treatment fluid. The seventh embodiments can be modified to form additional seventh embodiments in which the medical treatment device includes a renal replacement therapy system and the treatment fluid includes dialysate or electrolyte.

According to eighth embodiments, the disclosed subject matter includes a blood treatment device with one or more inflow pumps and one or more outflow pumps that are configured to be interoperable with a replaceable tubing set that engages with the one or more inflow and outflow pumps to establish flows into and out of a treatment device and/or a patient access connectable to the tubing set. The flows into and out of the treatment device are established in inflow and outflow channel portions of the tubing set, respectively. One or more valve actuators interoperable with the tubing set to divert flow through a branch channel thereof, the branch channel fluidly coupling the inflow and outflow channel portions of the tubing set that are in engagement with the one or more inflow and one or more outflow pumps. a programmable controller connected to control speeds of the one or more inflow and one or more outflow pumps. The programmable controller is connected to control the valve actuators. the programmable controller has a pressure terminal that receives pressure signals from a pressure sensor in engagement with the branch channel of a connected tubing set. The programmable controller has a data storage storing calibration data that allows the controller to establish predefined flow rates in the one or more inflow and one or more outflow pumps. The data storage further stores instructions which, when executed, cause the controller to operate the one or more inflow and one or more outflow pumps to perform a blood treatment using the calibration data to control flows in the inflow and outflow channels and automatically and temporarily generate a flow in the branch channel and store pressure samples in the data storage over a sampling period. The controller further corrects at least portions of the calibration data in response to the samples.

The eighth embodiments can be modified to form additional eighth embodiments in which the branch channel has an accumulator chamber with a diaphragm on a side thereof, forming a pressure pod, which transmits pressurized air to the pressure sensor, the pressure sensor includes a pressure transducer. The eighth embodiments can be modified to form additional eighth embodiments in which the one or more inflow and outflow pumps are peristaltic pumps. The eighth embodiments can be modified to form additional eighth embodiments in which inflow ones of the one or more inflow and outflow pumps generate different pressure pulse frequencies for a given flow rate than outflow ones of the one or more inflow and outflow pumps for the given flow rate. The eighth embodiments can be modified to form additional eighth embodiments in which inflow ones of the one or more inflow and outflow pumps generate different pressure pulse frequencies for a given flow rate than outflow ones of the one or more inflow and outflow pumps for the given flow rate as a result of differences in the inner diameters of respective pumping portions of the tubing set. The eighth embodiments can be modified to form additional eighth embodiments in which inflow ones of the one or more inflow and outflow pumps generate different pressure pulse frequencies for a given flow rate than outflow ones of the one or more inflow and outflow pumps for the given flow rate as a result of differences in the number of rollers among the one or more inflow and outflow pumps. The eighth embodiments can be modified to form additional eighth embodiments in which the controller is programmed to modify at least one parameter of pumping by the one or more inflow and outflow pumps such that beats resulting from a superposition of the pulses in the branch channel are either multiple times shorter than, or multiple times longer than a period of the measuring. The eighth embodiments can be modified to form additional eighth embodiments in which the at least one parameter includes a controlling a net flow rate through the branch channel such that predefined ranges of the net flow are avoided.

The eighth embodiments can be modified to form additional eighth embodiments in which the at least one parameter includes a suction head of at least one of the one or more inflow and outflow pumps. The eighth embodiments can be modified to form additional eighth embodiments in which the at least one parameter includes an inlet-outlet pressure differential of at least one of the one or more inflow and outflow pumps. The eighth embodiments can be modified to form additional eighth embodiments in which the at least one parameter includes a volumetric efficiency of at least one of the one or more inflow and outflow pumps. The eighth embodiments can be modified to form additional eighth embodiments in which the at least one parameter includes a phase angle of at least one of the one or more inflow and outflow pumps relative to at least another of the one or more inflow and outflow pumps. The eighth embodiments can be modified to form additional eighth embodiments in which the at least one parameter includes a flow restriction positioned to restrict flow upstream and/or downstream of the one or more inflow and outflow pumps.

According to ninth embodiments, the disclosed subject matter includes a method of regulating the balanced flow of fluids with at production times, in a system has first and second fluid channels each with at least one respective pump for each of the first and second fluid channels. The method includes using a controller to control the rate of pumping of one or more of the respective pumps to establish flows in the first and second channels with volume flow rates of a predefined ratio based on calibration data stored in the controller. The first and second channels connect to a fluid handling device. The method includes, at test times, using the controller, temporarily establishing a flow from the first channel to the second channel through a test flow branch with a pressure sensor and receiving, and storing static pressure data representing, a test branch pressure in the test branch at the controller. The method includes adjusting a flow restriction in the first channel, the second channel, or the test branch to make the inlet and/or outlet pressure of one or more of the at least one respective pumps equal to a predefined pressure. The method includes, in response to the static pressure data, using the controller, revising the calibration data. thereafter, using the controller, adjusting one or more of the respective pumps according to the calibration data adjusted by the adjusting.

The ninth embodiments can be modified to form additional ninth embodiments including, prior to the test times, measuring a pressure into or out of one of the respective pumps and storing a target pressure, the predefined pressure is responsive to the target pressure. The ninth embodiments can be modified to form additional ninth embodiments including, at test times, adjusting a phase angle between two of the respective pumps such that sampling bias in the static pressure data is reduced. The ninth embodiments can be modified to form additional ninth embodiments including, at test times, adjusting a phase angle between two of the respective pumps such that sampling bias in the static pressure data does not exceed a wavelength of that of a pressure pulsation generated by either of the two of the respective pumps. The ninth embodiments can be modified to form additional ninth embodiments in which wherein the adjusting is effective to make any beats due to fluctuations caused by beat interference between pressure pulses generated by the respective pumps to be at a frequency that is multiple times higher than an inverse of the an interval of the test times. The ninth embodiments can be modified to form additional ninth embodiments in which the revising is in response to a moving average of the static pressure data generated using a non-rectangular averaging window. The ninth embodiments can be modified to form additional ninth embodiments in which the sampling frequency of the static pressure data is at least ten times a highest frequency of pressure pulses resulting from either of the one or more respective pumps. The ninth embodiments can be modified to form additional ninth embodiments in which the controller receives a local pressure upstream and/or downstream of at least one of the respective pumps, the adjusting is responsive to both the test branch pressure signal and the local pressure signal. The ninth embodiments can be modified to form additional ninth embodiments in which the receiving a local pressure includes receiving local pressures upstream and downstream of the at least one of the respective pumps. The ninth embodiments can be modified to form additional ninth embodiments in which the controller controls a valve that selectively permits flow through the test flow branch and the controller automatically selects a time of the temporarily establishing. The ninth embodiments can be modified to form additional ninth embodiments in which the controller controls a valve that selectively permits flow through the test flow branch and the controller automatically selects multiple instances of the temporarily establishing. The ninth embodiments can be modified to form additional ninth embodiments in which the fluid handling device is a blood treatment device. The ninth embodiments can be modified to form additional ninth embodiments in which the blood treatment device is a dialyzer or a hemofilter and replacement fluid source. The ninth embodiments can be modified to form additional ninth embodiments in which the respective pumps are peristaltic pumps. The ninth embodiments can be modified to form additional ninth embodiments in which the respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing. The ninth embodiments can be modified to form additional ninth embodiments in which the respective pumps are peristaltic pumps and pumping tube segments of no one of the respective pumps responsible for the entering flow has an inner diameter the same as a pumping tube segment inner diameter of a one of the respective pumps responsible for the leaving flow. The ninth embodiments can be modified to form additional ninth embodiments in which the respective pumps are peristaltic pumps and the number of rollers for no one of the respective pumps responsible for the entering flow is the same as the number of rollers of a one of the respective pumps responsible for the leaving flow. The ninth embodiments can be modified to form additional ninth embodiments in which the controller stores data representing operating conditions that coincide with respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing.

According to tenth embodiments, the disclosed subject matter includes a method of maintaining a predefined ratio of flow rates in first and second channels with connecting the first and second channels temporarily to create a continuous flow between them. The method includes measuring a static pressure of a channel carrying the continuous flow temporarily generated in the connecting and adjusting calibration data of one or more respective pumps that generate at least one of the second flows responsively to a result of the measuring.

The tenth embodiments can be modified to form additional tenth embodiments in which the connecting, measuring, and adjusting are done automatically by a programmable controller, the method further comprising adjusting a speed of the one or more respective pumps in response to the calibration data. The tenth embodiments can be modified to form additional tenth embodiments that include limiting low frequency pressure fluctuations in the continuous flow. The tenth embodiments can be modified to form additional tenth embodiments in which the limiting includes selecting the one or more respective pumps whose pulsation frequencies at a rate of the continuous flow produce beats due to superposition of the pulsations that are either multiple times shorter than, or multiple times longer than a period of the measuring, the measuring includes sampling the static pressure multiple times over the period of the measuring. The tenth embodiments can be modified to form additional tenth embodiments in which the limiting includes adjusting the one or more respective pumps to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies. The tenth embodiments can be modified to form additional tenth embodiments in which the one or more respective pumps have different ratios as a result of has differences in one or a combination of tubing inner diameter or number of rollers of a peristaltic pump rotor. The tenth embodiments can be modified to form additional tenth embodiments in which one or both of the first and second channels includes at least two fluid lines. The tenth embodiments can be modified to form additional tenth embodiments in which the connecting, measuring, and adjusting are done automatically by a programmable controller, the method further comprising adjusting a speed of the one or more respective pumps in response to the calibration data. The tenth embodiments can be modified to form additional tenth embodiments that include limiting low frequency pressure fluctuations in the continuous flow. The tenth embodiments can be modified to form additional tenth embodiments in which the limiting includes selecting the one or more respective pumps whose pulsation frequencies at a rate of the continuous flow produce beats due to superposition of the pulsations that are either multiple times shorter than, or multiple times longer than a period of the measuring, the measuring includes sampling the static pressure multiple times over the period of the measuring. The tenth embodiments can be modified to form additional tenth embodiments in which the limiting includes adjusting the one or more respective pumps to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies. The tenth embodiments can be modified to form additional tenth embodiments in which the one or more respective pumps have different ratios as a result of has differences in one or a combination of tubing inner diameter, suction side head pressure, or number of rollers of a respective peristaltic pump rotor. The tenth embodiments can be modified to form additional tenth embodiments in which the first and second flow channels are, at times other than the measuring, connected by a controller to a medical treatment device for the supply and withdrawal of treatment fluid. The tenth embodiments can be modified to form additional tenth embodiments in which the medical treatment device includes a renal replacement therapy system and the treatment fluid includes dialysate or electrolyte.

According to eleventh embodiments, the disclosed subject matter includes a system for regulating balanced flow of fluids with first and second fluid channels connectable to a fluid handling device, each with at least one respective pump for each of the first and second fluid channels, a controller connected to the respective pumps to control the rate of pumping of one or more of the respective pumps, the controller is connected to one or more valves to permit it to establish flows in the first and second channels. A ratio of flow rates of entering and leaving flows to and from the fluid handling device is controlled by the controller to effect a predefined net transfer of fluid to or from the fluid handling device responsively to calibration data accessible to the controller. The controller, at selected times, temporarily establishes a bypass flow directly from the first channel to the second channel, thereby bypassing connectors to the fluid handling device, through a test flow branch by defining selected flow paths through the one or more valves. a pressure sensor device in the test flow branch, the controller sampling a signal of the bypass flow pressure in the test branch and in response to the samples, the controller adjusting the calibration data. The controller, uses the adjusted calibration data stored in the controller to adjust the one or more of the respective pumps in order to effect the predefined net transfer of fluid to or from the fluid handling device.

The eleventh embodiments can be modified to form additional eleventh embodiments in which the controller is connected to receive a local pressure upstream and/or downstream of at least one of the respective pumps, the adjusting is responsive to both the test branch pressure signal and the local pressure signal. The eleventh embodiments can be modified to form additional eleventh embodiments in which the received local pressure includes local pressures upstream and/or downstream of the at least one of the respective pumps. The eleventh embodiments can be modified to form additional eleventh embodiments in which the controller controls a valve that selectively permits flow through the test flow branch and the controller automatically selects a time of establishing the continuous flow and performing the sampling. The eleventh embodiments can be modified to form additional eleventh embodiments in which the controller controls a valve that selectively permits flow through the test flow branch and the controller automatically iteratively establishes the continuous flow and the performance of the sampling. The eleventh embodiments can be modified to form additional eleventh embodiments in which the fluid handling device is a blood treatment device. The eleventh embodiments can be modified to form additional eleventh embodiments in which the blood treatment device is a dialyzer or a hemofilter and replacement fluid source. The eleventh embodiments can be modified to form additional eleventh embodiments in which the respective pumps are peristaltic pumps. The eleventh embodiments can be modified to form additional eleventh embodiments in which the respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing. The eleventh embodiments can be modified to form additional eleventh embodiments in which the respective pumps are peristaltic pumps and pumping tube segments of no one of the respective pumps responsible for the entering flow has an inner diameter the same as a pumping tube segment inner diameter of a one of the respective pumps responsible for the leaving flow. The eleventh embodiments can be modified to form additional eleventh embodiments in which the respective pumps are peristaltic pumps and the number of rollers for no one of the respective pumps responsible for the entering flow is the same as the number of rollers of a one of the respective pumps responsible for the leaving flow. The eleventh embodiments can be modified to form additional eleventh embodiments in which the controller stores data representing operating conditions that coincide with respective pumps are of a type that produce pressure pulses at regular intervals during pumping, the respective pumps is selected such that the pressure pulses of pumps flowing into and out of the test flow branch differ by at least a factor of two at pumping rates that occur times other than at times of the temporarily establishing.

According to twelfth embodiments, the disclosed subject matter includes a method for maintaining a predefined ratio of flow rates in first and second channels with connecting the first and second channels temporarily to create a continuous flow between them. The method includes measuring a static pressure of a channel carrying the continuous flow temporarily generated in the connecting. The method includes adjusting calibration data of one or more respective pumps that generate at least one of the second flows responsively to a result of the measuring.

The twelfth embodiments can be modified to form additional twelfth embodiments in which the connecting, measuring, and adjusting are done automatically by a programmable controller, the system further comprising adjusting a speed of the one or more respective pumps in response to the calibration data.

The twelfth embodiments can be modified to form additional twelfth embodiments in which the first and second flow channels and/or the test branch and/or the one at least one respective pump are configured to limit low frequency pressure fluctuations in the continuous flow due to the superposition of pressure pulses of the respective pumps that form beats. The twelfth embodiments can be modified to form additional twelfth embodiments in which the one or more respective pumps have pulsation frequencies at a rate of the continuous flow that produces beats due to superposition of the pulsations that are either multiple times shorter than, or multiple times longer than a period of the measuring, the measuring includes sampling the static pressure multiple times over the period of the measuring. The twelfth embodiments can be modified to form additional twelfth embodiments in which the one or more respective pumps are controlled to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies.

The twelfth embodiments can be modified to form additional twelfth embodiments in which the one or more respective pumps have different ratios as a result of has differences in one or a combination of tubing inner diameter or number of rollers of a peristaltic pump rotor. The twelfth embodiments can be modified to form additional twelfth embodiments in which one or both of the first and second channels includes at least two fluid lines. The twelfth embodiments can be modified to form additional twelfth embodiments in which the connecting, measuring, and adjusting are done automatically by a programmable controller, the system further comprising adjusting a speed of the one or more respective pumps in response to the calibration data. The twelfth embodiments can be modified to form additional twelfth embodiments in which the first and second flow channels and/or the test branch and/or the one at least one respective pump are configured to limit low frequency pressure fluctuations in the continuous flow due to the superposition of pressure pulses of the respective pumps that form beats. The twelfth embodiments can be modified to form additional twelfth embodiments in which the one or more respective pumps have pulsation frequencies at a rate of the continuous flow that produces beats due to superposition of the pulsations that are either multiple times shorter than, or multiple times longer than a period of the measuring, the measuring includes sampling the static pressure multiple times over the period of the measuring. The twelfth embodiments can be modified to form additional twelfth embodiments in which the one or more respective pumps are controlled to a rate of the continuous flow that produces beats due to superposition of the pulsations thereof that are either multiple times shorter than, or multiple times longer than a period of the measuring, the measuring includes sampling the static pressure multiple times over the period of the measuring, the one or more respective pumps has different ratios of flow rate to pulsation frequencies. The twelfth embodiments can be modified to form additional twelfth embodiments in which the one or more respective pumps have different ratios as a result of has differences in one or a combination of tubing inner diameter or number of rollers of a peristaltic pump rotor. The twelfth embodiments can be modified to form additional twelfth embodiments in which the first and second flow channels are, at times other than at times that the continuous flow is established by the controller, connected The twelfth embodiments can be modified to form additional twelfth embodiments in which the medical treatment device includes a renal replacement therapy system and the treatment fluid includes dialysate or electrolyte.

According to thirteenth embodiments, the disclosed subject matter includes a blood treatment device with one or more inflow pumps and one or more outflow pumps that are configured to be interoperable with a replaceable tubing set that engages with the one or more inflow and outflow pumps to establish flows into and out of a treatment device and/or a patient access connectable to the tubing set, the flows into and out of the treatment device is established in inflow and outflow channel portions of the tubing set, respectively. One or more valve actuators are interoperable with the tubing set to divert flow through a branch channel thereof, the branch channel fluidly coupling the inflow and outflow channel portions of the tubing set that are in engagement with the one or more inflow and one or more outflow pumps. A programmable controller connects to control speeds of the one or more inflow and one or more outflow pumps. The programmable controller is connected to control the valve actuators. the programmable controller has a pressure terminal that receives pressure signals from a pressure sensor in engagement with the branch channel of a connected tubing set. the programmable controller has a data storage storing calibration data that allows the controller to establish predefined flow rates in the one or more inflow and one or more outflow pumps, the data storage further storing instructions which when executed, cause the controller to operate the one or more inflow and one or more outflow pumps to perform a blood treatment using the calibration data to control flows in the inflow and outflow channels, automatically and temporarily generate a flow in the branch channel and store pressure samples in the data storage over a sampling period, and correct at least portions of the calibration data in response to the samples.

The thirteenth embodiments can be modified to form additional thirteenth embodiments in which the branch channel has an accumulator chamber with a diaphragm on a side thereof, forming a pressure pod, which transmits pressurized air to the pressure sensor, the pressure sensor includes a pressure transducer. The thirteenth embodiments can be modified to form additional thirteenth embodiments in which the one or more inflow and outflow pumps are peristaltic pumps. The thirteenth embodiments can be modified to form additional thirteenth embodiments in which inflow ones of the one or more inflow and outflow pumps generate different pressure pulse frequencies for a given flow rate than outflow ones of the one or more inflow and outflow pumps for the given flow rate. The thirteenth embodiments can be modified to form additional thirteenth embodiments in which inflow ones of the one or more inflow and outflow pumps generate different pressure pulse frequencies for a given flow rate than outflow ones of the one or more inflow and outflow pumps for the given flow rate as a result of differences in the inner diameters of respective pumping portions of the tubing set. The thirteenth embodiments can be modified to form additional thirteenth embodiments in which inflow ones of the one or more inflow and outflow pumps generate different pressure pulse frequencies for a given flow rate than outflow ones of the one or more inflow and outflow pumps for the given flow rate as a result of differences in the number of rollers among the one or more inflow and outflow pumps. The thirteenth embodiments can be modified to form additional thirteenth embodiments in which the controller is programmed to modify at least one parameter of pumping by the one or more inflow and outflow pumps such that beats resulting from a superposition of the pulses in the branch channel are either multiple times shorter than, or multiple times longer than a period of the measuring. The thirteenth embodiments can be modified to form additional thirteenth embodiments in which the at least one parameter includes a controlling a net flow rate through the branch channel such that predefined ranges of the net flow are avoided. The thirteenth embodiments can be modified to form additional thirteenth embodiments in which the at least one parameter includes a suction head of at least one of the one or more inflow and outflow pumps. The thirteenth embodiments can be modified to form additional thirteenth embodiments in which the at least one parameter includes an inlet-outlet pressure differential of at least one of the one or more inflow and outflow pumps. The thirteenth embodiments can be modified to form additional thirteenth embodiments in which the at least one parameter includes a volumetric efficiency of at least one of the one or more inflow and outflow pumps. The thirteenth embodiments can be modified to form additional thirteenth embodiments in which the at least one parameter includes a phase angle of at least one of the one or more inflow and outflow pumps relative to at least another of the one or more inflow and outflow pumps. The thirteenth embodiments can be modified to form additional thirteenth embodiments in which the at least one parameter includes a flow restriction positioned to restrict flow upstream and/or downstream of the one or more inflow and outflow pumps.

According to fourteenth embodiments, the disclosed subject matter includes a flow balancing system for a blood treatment device with one or more inflow pumps and one or more outflow pumps positioned to engage a replaceable fluid circuit to pump fluid into and out of a treatment device, respectively. At least one adjustable flow-restricting actuator generates a flow restriction of a selected magnitude in at least one portion of the replaceable fluid circuit, each located at an inlet of a respective one of the one or more inflow and outflow pumps so as to generate a selectable suction head during pumping. Valve actuators control valve portions of the replaceable fluid circuit. a controller connected to the one or more inflow and outflow pumps to control speeds thereof, connected to control the valve actuators, and connected to control the at least one adjustable flow-restricting actuator. The controller has a data store storing a model that predicts data indicative of a flow rate based on at least one of pump speed and inlet and/or outlet pressure of each of the one or more inflow and outflow pumps. The replaceable fluid circuit has inflow, outflow, and bridge channels, the inflow and outflow channels connecting to the treatment device, the inflow and outflow channels is connected to the bridge channel such that they can be bridged by the valve actuators to cause flow in the inflow channel to bypass the treatment device flowing from the inflow channel through the branch channel to the outlet channel. One or more pressure sensors are interoperable with the bridge channel to detect pressure at a respective one or more points therealong. The controller is programmed to, generate a test command and in response thereto, perform a calibration procedure during which it bridges the inflow and outflow channels through the branch channel and calculate a difference in flow rates between the one or more inflow and the one or outflow pumps through the branch channel and, responsively thereto, calculates adjustments to the model. the controller is programmed to control the one or more inflow and outflow pumps responsively to the model.

The fourteenth embodiments can be modified to form additional fourteenth embodiments in which the difference in flow rates between the one or more inflow and the one or outflow pumps through the branch channel is calculated from pressure signals indicating a pressure drop in the branch channel. The fourteenth embodiments can be modified to form additional fourteenth embodiments in which the difference in flow rates between the one or more inflow and the one or outflow pumps through the branch channel is calculated from a single pressure signal indicating a net inflow or net outflow from the branch channel. The fourteenth embodiments can be modified to form additional fourteenth embodiments in which the controller is programmed to generate the test command upon the detection of a predefined operating time interval of one of the one or more inflow and outflow pumps.

The fourteenth embodiments can be modified to form additional fourteenth embodiments in which the controller is programmed to generate the test command upon the detection of a predefined number of rotations of the one or more inflow and outflow pumps. The fourteenth embodiments can be modified to form additional fourteenth embodiments in which wherein the controller is programmed to generate the test command upon the detection of a predefined net flow volume derived numerically from the number of rotations of the one or more inflow and outflow pumps. The fourteenth embodiments can be modified to form additional fourteenth embodiments in which the controller is programmed to adjust the at least one adjustable flow-restricting actuator to generate an inlet pressure of one of the one or more inflow and outflow pumps during the calibration operation. The fourteenth embodiments can be modified to form additional fourteenth embodiments in which the controller is programmed to adjust the at least one adjustable flow-restricting actuator to generate a first inlet pressure at one of the one or more inflow and outflow pumps during the calibration operation matching a second inlet pressure occurring during a treatment operation. The fourteenth embodiments can be modified to form additional fourteenth embodiments in which the controller is programmed to adjust the at least one adjustable flow-restricting actuator to generate multiple first inlet pressures at one of the one or more inflow and outflow pumps during the calibration operation. The fourteenth embodiments can be modified to form additional fourteenth embodiments in which the difference in flow rates between the one or more inflow and the one or outflow pumps through the branch channel is calculated from pressure signals indicating a pressure drop in the branch channel. The fourteenth embodiments can be modified to form additional fourteenth embodiments in which the difference in flow rates between the one or more inflow and the one or outflow pumps through the branch channel is calculated from a single pressure signal indicating a net inflow or net outflow from the branch channel. The fourteenth embodiments can be modified to form additional fourteenth embodiments in which the controller is programmed to generate the test command upon the detection of a predefined operating time interval of one of the one or more inflow and outflow pumps. The fourteenth embodiments can be modified to form additional fourteenth embodiments in which the controller is programmed to generate the test command upon the detection of a predefined number of rotations of the one or more inflow and outflow pumps. The fourteenth embodiments can be modified to form additional fourteenth embodiments in which wherein the controller is programmed to generate the test command upon the detection of a predefined net flow volume derived numerically from the number of rotations of the one or more inflow and outflow pumps. The fourteenth embodiments can be modified to form additional fourteenth embodiments in which the controller is programmed to adjust the at least one adjustable flow-restricting actuator to generate an inlet pressure of one of the one or more inflow and outflow pumps during the calibration operation. The fourteenth embodiments can be modified to form additional fourteenth embodiments in which the difference in flow rates between the one or more inflow and the one or outflow pumps through said branch channel is calculated from pressure signals indicating a pressure drop in the branch channel. The fourteenth embodiments can be modified to form additional fourteenth embodiments in which the controller is programmed to generate the test command upon the detection of a predefined temperature or temperature change of the replaceable fluid circuit. The fourteenth embodiments can be modified to form additional fourteenth embodiments in which the controller is programmed to generate the test command upon the detection of a predefined pressure or pressure change of at a location in the replaceable fluid circuit. The fourteenth embodiments can be modified to form additional fourteenth embodiments in which the controller is programmed to control the valve actuators to recover fluid flowing through the branch channel for use in a treatment. The fourteenth embodiments can be modified to form additional fourteenth embodiments in which the replaceable fluid circuit includes a storage vessel in communication with the outflow channel and the inflow channel and the controller is configured to direct fluid flowing through the branch channel to the storage vessel and from the storage vessel to the inflow channel during a treatment, whereby fluid flowing in the branch channel is recovered for use during treatment. The fourteenth embodiments can be modified to form additional fourteenth embodiments in which the model includes a lookup table representing a relationship between inlet pressure, pump rotation speed, and flow. The fourteenth embodiments can be modified to form additional fourteenth embodiments in which the model includes a function representing a relationship between inlet pressure, pump rotation speed, and flow. The fourteenth embodiments can be modified to form additional fourteenth embodiments in which the model includes a data structure representing a relationship between inlet pressure, pump rotation speed, and flow. The fourteenth embodiments can be modified to form additional fourteenth embodiments in which the controller calculates a difference in flow rates between the one or more inflow and the one or outflow pumps through the branch channel responsively to a moving time-average pressure drop or pressure. The fourteenth embodiments can be modified to form additional fourteenth embodiments in which the controller calculates a difference in flow rates between the one or more inflow and the one or outflow pumps through the branch channel responsively to a moving time-average pressure drop or pressure generated from a non-rectangular averaging window. The fourteenth embodiments can be modified to form additional fourteenth embodiments in which the controller calculates a difference in flow rates between the one or more inflow and the one or outflow pumps through the branch channel responsively to a moving time-average pressure drop or pressure generated from a non-rectangular averaging window whose temporal length is greater than a wavelength of flow pulses caused by the one or more inflow and outflow pumps flowing fluid through the branch channel. The fourteenth embodiments can be modified to form additional fourteenth embodiments in which the branch channel includes an accumulator. The fourteenth embodiments can be modified to form additional fourteenth embodiments in which the branch channel includes an accumulator with an internal volume in flow communication with the branch channel, which internal volume size is selectable. The fourteenth embodiments can be modified to form additional fourteenth embodiments in which the branch channel includes an accumulator with an internal volume in flow communication with the branch channel, which internal volume size is selectable under control of the controller. The fourteenth embodiments can be modified to form additional fourteenth embodiments in which the controller is programmed to adjust the flow rate of the one or more inflow and outflow pumps to generate multiple flow rates through the branch channel during the calibration operation. The fourteenth embodiments can be modified to form additional fourteenth embodiments in which the controller is programmed to adjust the at least one adjustable flow-restricting actuator to generate multiple first inlet pressures at one of the one or more inflow and outflow pumps during the calibration operation. The fourteenth embodiments can be modified to form additional fourteenth embodiments in which the branch channel includes an accumulator. The fourteenth embodiments can be modified to form additional fourteenth embodiments in which the branch channel includes an accumulator with an internal volume in flow communication with the branch channel, which internal volume size is selectable. The fourteenth embodiments can be modified to form additional fourteenth embodiments in which the branch channel includes an accumulator with an internal volume in flow communication with the branch channel, which internal volume size is selectable under control of the controller.

According to fifteenth embodiments, the disclosed subject matter includes a flow system with first and second peristaltic pumps interconnected in tandem by a channel with a component that permits a net flow into and out of the channel between the first and second peristaltic pumps. The first and second peristaltic pumps has different sized pumping tube segments engaged with respective rotors thereof such that when the first and second peristaltic pumps are pumping approximately equal flow rates, the frequency of flow and pressure fluctuations are substantially different.

The fifteenth embodiments can be modified to form additional fifteenth embodiments in which the component includes a dialyzer. The fifteenth embodiments can be modified to form additional fifteenth embodiments in which the fluid is incompressible. The fifteenth embodiments can be modified to form additional fifteenth embodiments in which the first and second peristaltic pumps are interconnected by a fluid circuit that lacks a pulsation damper.

According to sixteenth embodiments, the disclosed subject matter includes a flow system with a fluid circuit with inflow and outflow channels engageable, with respective peristaltic pumps, the inflow and outflow channels is connected to a treatment device to provide ingoing and outcoming flow to and from the treatment device. The fluid circuit has valve portions that, upon actuation, connect a selected either one of the inflow and outflow channels to a common segment. The common segment has pressure sensor elements on inlet and outlet ends thereof.

The sixteenth embodiments can be modified to form additional sixteenth embodiments in which a fluid management device with peristaltic pump and valve actuators and a controller connected to the peristaltic pump and valve actuators to control them, the peristaltic pump and valve actuators engaged with the inflow and outflow channels and valve portions respectively. The controller is connected to the pressure sensor elements, the controller further is programmed to maintain inflow and outflow rates to achieve a predefined ratio of net flow into or out of the treatment during a treatment interval responsively to corrections derived from comparing pressure differences across sad pressure sensors in ingoing and outgoing flows flowing through the common segment.

The sixteenth embodiments can be modified to form additional sixteenth embodiments in which the controller is programmed to switch the common segment between the ingoing flow and the outgoing flow periodically during a treatment. The sixteenth embodiments can be modified to form additional sixteenth embodiments in which the fluid circuit is a disposable component. The sixteenth embodiments can be modified to form additional sixteenth embodiments in which the pressure sensor elements are pressure pods entirely of plastic connectable to pressure transducers which are in turn connected to the controller. The sixteenth embodiments can be modified to form additional sixteenth embodiments in which the common segment is of a material that has a lower compliance than that of other portions of the fluid circuit.

According to seventeenth embodiments, the disclosed subject matter includes a system for regulating balanced flow of fluids with a fluid circuit with first and second fluid channels connectable to a fluid handling device, each with at least one respective pump for each of the first and second fluid channels, a controller connected to the respective pumps to control the rate of pumping of one or more of the respective pumps, the controller is connected to one or more valves to permit it to establish flows in the first and second channels. A ratio of flow rates of entering and leaving flows to and from the fluid handling device is controlled by the controller to effect a predefined net transfer of fluid to or from the fluid handling device responsively to calibration data accessible to the controller. The controller, at selected times, temporarily establishes one or more calibration flow paths in the fluid circuit, the calibration flow paths communicating respectively with ones of the first and second fluid channels to cause flow through a flow measurement component that generates a signal indicating a flow rate or relative flow rate generated by the respective pumps. The controller samples the signal and in response to resulting samples, the controller adjusting the calibration data. The controller, uses the adjusted calibration data stored in the controller to adjust the one or more of the respective pumps in order to effect the predefined net transfer of fluid to or from the fluid handling device. The selected times are determined by the controller responsively to detection of a number of rotations of one or more of the respective pumps, a change in temperature of a portion of the fluid circuit, a change in pressure of a portion of the fluid circuit, a change in a configuration of the fluid circuit, an elapsed time since the fluid circuit was set up, or an elapsed time that the fluid circuit transferred fluid was transferring fluid to and from the fluid handling device.

The seventeenth embodiments can be modified to form additional seventeenth embodiments in which the controller is connected to receive a local pressure upstream and/or downstream of at least one of the respective pumps, the adjusting is responsive to both the samples and the local pressure signal. The seventeenth embodiments can be modified to form additional seventeenth embodiments in which the received local pressure includes local pressures upstream and downstream of the at least one of the respective pumps. The seventeenth embodiments can be modified to form additional seventeenth embodiments in which the calibration flow paths include one through a test flow branch that directly connects ones of the first and second fluid channels. The seventeenth embodiments can be modified to form additional seventeenth embodiments in which the controller controls a valve that selectively permits flow through the test flow branch and the controller automatically iteratively establishes the continuous flow and the performance of the sampling. The seventeenth embodiments can be modified to form additional seventeenth embodiments in which the fluid handling device is a blood treatment device. The seventeenth embodiments can be modified to form additional seventeenth embodiments in which the blood treatment device is a dialyzer or a hemofilter and replacement fluid source. The seventeenth embodiments can be modified to form additional seventeenth embodiments in which the respective pumps are peristaltic pumps. The seventeenth embodiments can be modified to form additional seventeenth embodiments in which the selected times are determined by the controller responsively to detection of a number of rotations of one or more of the respective pumps. The seventeenth embodiments can be modified to form additional seventeenth embodiments in which the selected times are determined by the controller responsively to detection of a change in temperature of a portion of the fluid circuit. The seventeenth embodiments can be modified to form additional seventeenth embodiments in which the selected times are determined by the controller responsively to detection of a change in pressure of a portion of the fluid circuit. The seventeenth embodiments can be modified to form additional seventeenth embodiments in which the selected times are determined by the controller responsively to detection of a change in a configuration of the fluid circuit. The seventeenth embodiments can be modified to form additional seventeenth embodiments in which the selected times are determined by the controller responsively to detection of an elapsed time since the fluid circuit was set up. The seventeenth embodiments can be modified to form additional seventeenth embodiments in which the selected times are determined by the controller responsively to detection of an elapsed time that the fluid circuit transferred fluid was transferring fluid to and from the fluid handling device.

According to eighteenth embodiments, the disclosed subject matter includes a method of controlling a rate of ultrafiltration/infusion in an extracorporeal blood circuit with pumping treatment fluid through blood treatment device using one or more peristaltic pumps. The method includes pumping blood through the blood treatment device using two pumps whose rates of flow are controlled by a controller to achieve a predefined volume of ultrafiltration by the end of a treatment interval. at times during a treatment, flowing blood between the two pumps and receiving a pressure signal representative of the relative rates of flow between the two pumps. In the method, based on the pressure signal, calibration data is revised used to control the rates of flow to achieve the predefined volume.

The eighteenth embodiments can be modified to form additional eighteenth embodiments in which the two pumps are peristaltic pumps. The eighteenth embodiments can be modified to form additional eighteenth embodiments in which the receiving a pressure signal includes receiving a transient static pressure generated by unequal flows of the two pumps to and from a branch channel connecting the two pumps. The eighteenth embodiments can be modified to form additional eighteenth embodiments in which the revising includes changing a pumping rate of one of the two pumps responsively to an average of the pressure signal to achieve an unchanging pressure and using data indicating the rotation rate of the one of the two pumps when the unchanging pressure is achieved to revise the calibration data.

According to nineteenth embodiments, the disclosed subject matter includes a system for regulating balanced flow of fluids with first and second fluid channels connectable to a fluid handling device, each with at least one respective pump for each of the first and second fluid channels, a controller connected to the respective pumps to control the rate of pumping of one or more of the respective pumps. The controller is connected to one or more valves to permit it to establish flows in the first and second channels. a ratio of flow rates of entering and leaving flows to and from the fluid handling device is controlled by the controller to effect a predefined net transfer of fluid to or from the fluid handling device responsively to calibration data accessible to the controller. The controller, at selected times, temporarily establishes a bypass flow directly from the first channel to the second channel, thereby bypassing connectors to the fluid handling device, through a test flow branch by defining selected flow paths through the one or more valves. The test flow branch has an accumulator with a volume that can be changed under control of the controller, a pressure sensor device in the test flow branch to measure a pressure of fluid in the accumulator volume, the controller is programmed to sample a signal from the pressure sensor device and in response to the samples, the controller is programmed to adjust one or both of the calibration data and the accumulator volume. The controller is programmed to change the volume of the accumulator responsively to at least one flow condition in the test flow branch at the selected times. The controller, using the adjusted calibration data stored in the controller, adjusts the one or more of the respective pumps in order to effect the predefined net transfer of fluid to or from the fluid handling device at times other than the selected times.

The nineteenth embodiments can be modified to form additional nineteenth embodiments in which the controller is programmed to sample a signal from the pressure sensor device and in response to the samples, the controller adjusting the accumulator volume responsively to the pressure indicated by the pressure sensor device. The nineteenth embodiments can be modified to form additional nineteenth embodiments in which the at least one flow condition includes a flow rate through the test flow branch. The nineteenth embodiments can be modified to form additional nineteenth embodiments in which the controller is programmed to change the volume to keep the pressure therein constant and to adjust the calibration data responsively to the time-change of volume in the accumulator. The nineteenth embodiments can be modified to form additional nineteenth embodiments in which the controller is programmed to change the volume to keep the pressure therein constant and to adjust the rate of at least one of the respective pumps to minimize change in the volume in the accumulator. The nineteenth embodiments can be modified to form additional nineteenth embodiments in which the controller is programmed to adjust the calibration data responsively to the rate of rotation of the at least one of the respective pumps upon the minimization of the change in the volume in the accumulator. The nineteenth embodiments can be modified to form additional nineteenth embodiments in which the controller controls a valve that selectively permits flow through the test flow branch and the controller automatically selects a time of establishing the continuous flow and performing the sampling.

According to twentieth embodiments, the disclosed subject matter includes a medical treatment method according to which, at treatment times and using peristaltic pumps, medicament is flowed into and out of inflow and outflow channels connectable to a patient or treatment device. At calibration times, over a calibration interval of less than a minute, medicament is directly flowed between the inflow and outflow channels such that pulsations generated by the peristaltic pumps cause the pressure in a bridge channel between the inflow and outflow channels to fluctuate due to a superposition of a suction side pulsation and a pressure side pulsation of respective ones of the peristaltic pumps. The method includes, using an adjustable flow restrictor, selecting a suction head of at least one of the respective ones of the peristaltic pumps so as to change the pulsation frequency thereof so that it differs from that of the other of the ones of the peristaltic pumps by a predetermined amount.

The twentieth embodiments can be modified to form additional twentieth embodiments in which the predetermined amount is such that the ratio of the inverse of the difference between the pulsation frequencies of the ones of the peristaltic pumps is multiple times the calibration interval. The twentieth embodiments can be modified to form additional twentieth embodiments in which the predetermined amount is such that the ratio of the inverse of the difference between the pulsation frequencies of the ones of the peristaltic pumps is three times the calibration interval. The twentieth embodiments can be modified to form additional twentieth embodiments in which the predetermined amount is such that the ratio of the inverse of the difference between the pulsation frequencies of the ones of the peristaltic pumps is five times the calibration interval. The twentieth embodiments can be modified to form additional twentieth embodiments in which the predetermined amount is such that the ratio of the inverse of the difference between the pulsation frequencies of the ones of the peristaltic pumps is eight times the calibration interval. The twentieth embodiments can be modified to form additional twentieth embodiments in which the predetermined amount is such that the ratio of the inverse of the difference between the pulsation frequencies of the ones of the peristaltic pumps is twelve times the calibration interval.

According to twenty-first embodiments, the disclosed subject matter includes a medical treatment system with a first fluid management element that pumps fluid from a patient interface device during a treatment. A second fluid management element pumps fluid into a patient interface device during a treatment. The patient interface device is a device that interfaces with a patient fluid compartment includes at least one of a dialyzer, a hemofilter, a hemodiafilter, an ultrafilter, and a plasmapheresis device. A controller is connected to at least one of the first and second fluid management elements and has a processor programmed to regulate a net transfer of fluid into or from the patient interface device to achieve a predefined net removal of fluid from the patient during a therapeutic treatment implemented under control of the controller. A fluid circuit switch allows a flow from at least one of the first and second fluid management elements to be selectively and automatically configured under control of the controller between a therapy configuration for delivering the therapeutic treatment to a calibration configuration in which flow through the at least one of the first and second fluid management elements is temporarily diverted to a flow or pressure sensor that outputs a signal indicating a difference between the flow rates of the first and second fluid management elements that occurs during a treatment the fluid circuit is configured to return fluid passing the flow or pressure sensor to a recovery channel that is connected to permit a concurrent or later use of the fluid. The controller is programmed to calculate and store flow correction data representing a correction to be applied to a rate of flow of the at least one of the first and second fluid management elements responsively to the signal. The controller is further programmed to modify a flow rate of the at least one of the first and second fluid management elements responsively to the flow correction data.

The twenty-first embodiments can be modified to form additional twenty-first embodiments in which the fluid circuit is configured to return fluid passing the flow or pressure sensor to the at least one of the first and second fluid management elements. The twenty-first embodiments can be modified to form additional twenty-first embodiments in which the fluid circuit is configured to return fluid passing the flow or pressure sensor to a collection container connectable to the at least one of the first and second fluid management elements. The twenty-first embodiments can be modified to form additional twenty-first embodiments in which the fluid circuit is configured to return fluid passing the flow or pressure sensor to a collection container connectable to a source fluid container connected to the first and second fluid management elements. The twenty-first embodiments can be modified to form additional twenty-first embodiments in which a diverted flow in the calibration configuration flows between the first and second fluid management elements through a fluid accumulator connected to a pressure sensor that outputs the signal. The twenty-first embodiments can be modified to form additional twenty-first embodiments in which the accumulator is configured such that pressure increases as fluid fills the accumulator, whereby a difference in the flow rates of the first and second fluid management elements results in an increasing or decreasing pressure. The twenty-first embodiments can be modified to form additional twenty-first embodiments in which the accumulator has a residual volume of fluid to permit the measurement of a pressure change caused by a net removal or a net addition of fluid from or to the accumulator. The twenty-first embodiments can be modified to form additional twenty-first embodiments in which wherein the first fluid management element includes a peristaltic pump.

The twenty-first embodiments can be modified to form additional twenty-first embodiments in which the fluid circuit includes a disposable plastic tubing set and at least one control valve. The control valve includes a tubing junction that interfaces with one or more pinch clamps to form selectable flow paths, the pinch clamps is permanent reusable elements that pinch respective portions of the tubing set. The twenty-first embodiments can be modified to form additional twenty-first embodiments that include a third fluid management element that pumps fluid into the patient interface device during a treatment, the third fluid management element is coupled to a synchronization mechanism that causes the first and third fluid management elements to pump equal amounts of fluid per unit time during a treatment.

The twenty-first embodiments can be modified to form additional twenty-first embodiments that include a third fluid management element that pumps fluid into the patient interface device during a treatment. The third fluid management element is coupled to a mechanical synchronization mechanism that causes the first and third fluid management elements to move such that they pump equal amounts of fluid per unit time during a treatment through the fluid circuit.

The twenty-first embodiments can be modified to form additional twenty-first embodiments that include a blood circuit that interfaces with the patient interface device and, through the latter, to the fluid circuit. The twenty-first embodiments can be modified to form additional twenty-first embodiments in which the flow or pressure sensor is a flow sensor. The twenty-first embodiments can be modified to form additional twenty-first embodiments that include a blood circuit that interfaces with the patient interface device and, through the latter, to the fluid circuit and wherein a diverted flow in the calibration configuration flows through a flow path between the first and second fluid management elements through a fluid accumulator connected to a pressure sensor that outputs the signal, wherein a fluid circuit portion connected to the patient interface device is separate from the flow path.

The twenty-first embodiments can be modified to form additional twenty-first embodiments in which the second fluid management element is connected to a source of a medicament. The twenty-first embodiments can be modified to form additional twenty-first embodiments in which the controller is connected to a user interface and programmed to accept and store ultrafiltration data representing a target net ultrafiltration, wherein the controller is further programmed to control flow through the at least the one of the first and second fluid management elements responsively to the ultrafiltration data.

According to twenty-second embodiments, the disclosed subject matter includes a method of controlling a balanced flow in a medical treatment. The method includes using at least two pumps, flowing fluid into and out of a fluid management component over the course of a treatment interval and controlling the rates of flow of the at least two pumps to meet a target net flow into or out of the fluid management component at an end of the treatment interval. at calibration times during the treatment interval, and interconnecting the at least two pumps and detecting a property resulting from a difference in the flow rates of the pumps during a calibration interval. The method further includes, in response to the detecting, providing data to a controller that controls the rates of flow of the pumps. the controller, in response to the data, modifying the rates of flow to meet the target net flow.

The twenty-second embodiments can be modified to form additional twenty-second embodiments in which the fluid management component is a dialyzer. The twenty-second embodiments can be modified to form additional twenty-second embodiments in which the fluid management component is a combination of a hemofilter and patient access. The twenty-second embodiments can be modified to form additional twenty-second embodiments in which the fluid management component is a peritoneum of a patient is treated with peritoneal dialysis. The twenty-second embodiments can be modified to form additional twenty-second embodiments in which the controller controls the rates of the pumps to compensate an error that accumulates during an entirety of the treatment interval. The twenty-second embodiments can be modified to form additional twenty-second embodiments in which the controller controls the rates of the pumps to compensate an error that accumulates up to each instance of the calibration times.

According to twenty-third embodiments, the disclosed subject matter includes a method of controlling a balanced flow in a medical treatment. The method includes using at least two pumps, flowing fluid into and out of a fluid management component over the course of a treatment interval and controlling the rates of flow of the at least two pumps to meet a target net flow into or out of the fluid management component at an end of the treatment interval. The method includes, at calibration times during the treatment interval, interconnecting the at least two pumps and detecting a property resulting from a difference in the flow rates of the pumps during a calibration interval. The method includes, in response to the detecting, providing data to a controller that controls the rates of flow of the pumps. The controller, in response to the data, modifies the rates of flow to meet the target net flow.

The twenty-third embodiments can be modified to form additional twenty-third embodiments in which the flow rates established at the calibration times are varied and the detecting includes convolving a sampled pressure signal with a window function whose temporal size is varied with a flow rate of at least one of the at least two pumps. The twenty-third embodiments can be modified to form additional twenty-third embodiments in which the flow rates established at the calibration times are varied and the detecting includes convolving a sampled pressure signal with a window function whose shape is varied with a flow rate of at least one of the at least two pumps. The twenty-third embodiments can be modified to form additional twenty-third embodiments in which the flow rates established at the calibration times are varied and the detecting includes convolving a sampled pressure signal with a window function whose temporal size is varied with a characteristic of the superposition of pulsations in pressure caused by the at least two interconnected pumps. The twenty-third embodiments can be modified to form additional twenty-third embodiments in which the fluid management component is a dialyzer. The twenty-third embodiments can be modified to form additional twenty-third embodiments in which the fluid management component is a combination of a hemofilter and patient access. The twenty-third embodiments can be modified to form additional twenty-third embodiments in which the fluid management component is a peritoneum of a patient is treated with peritoneal dialysis. The twenty-third embodiments can be modified to form additional twenty-third embodiments in which the controller controls the rates of the pumps to compensate an error that accumulates during an entirety of the treatment interval. The controller controls the rates of the pumps to compensate an error that accumulates up to each instance of the calibration times.

According to twenty-fourth embodiments, the disclosed subject matter includes a medical treatment system that includes a first fluid management element that pumps fluid from a patient interface device during a treatment. A second fluid management element that pumps fluid into a patient interface device during a treatment. The patient interface device including at least one of a dialyzer, a hemofilter, a hemodiafilter, an ultrafilter, and a plasmapheresis device. A blood circuit that connects the patient interface device to a patient access. A controller connected to at least one of the first and second fluid management elements and having a processor programmed to implement a treatment mode in which it selectively establishes a net flow difference between the first fluid management element and second fluid management element corresponding to a net transfer of fluid into or from the patient interface device to achieve a predefined net removal of fluid from the patient by regulating rates of flow through said first and second fluid management elements. The controller being further configured to implement a calibration mode in prevents a net flow difference between the first fluid management element and the second fluid management element and simultaneously sample a flow or pressure sensor output, the sensor output indicating a difference between the respective flow rates through the first and second fluid management elements. The controller being programmed to calculate and store flow correction data representing a correction to be applied to a rate of flow of said at least one of the first and second fluid management elements responsively to samples of the flow or pressure sensor output. The controller being further programmed to modify a flow rate of said at least one of the first and second fluid management elements responsively to said flow correction data.

The twenty-fourth embodiments can be modified to form additional twenty-fourth embodiments in which the flow or pressure sensor is a pressure sensor. The twenty-fourth embodiments can be modified to form additional twenty-fourth embodiments in which a flow during the calibration configuration flows between the first and second fluid management elements through a circuit portion that includes a fluid accumulator connected to a pressure sensor that outputs said signal. The twenty-fourth embodiments can be modified to form additional twenty-fourth embodiments in which, in the calibration mode, pressure increases or decreases in the first and second fluid management elements in response to a difference between the flow rates of said first and second fluid management elements. The twenty-fourth embodiments can be modified to form additional twenty-fourth embodiments in which the accumulator has a residual volume of fluid to permit the measurement of a pressure change caused by a net removal or a net addition of fluid from or to said accumulator. The twenty-fourth embodiments can be modified to form additional twenty-fourth embodiments in which the first fluid management element includes a peristaltic pump. The twenty-fourth embodiments can be modified to form additional twenty-fourth embodiments in which the second fluid management element includes a peristaltic pump. The twenty-fourth embodiments can be modified to form additional twenty-fourth embodiments in which the fluid circuit includes a disposable plastic tubing set and at least one control valve, the control valve including a tubing junction that interfaces with one or more pinch clamps to form selectable flow paths, the pinch clamps being permanent reusable elements that pinch respective portions of the tubing set.

The twenty-fourth embodiments can be modified to form additional twenty-fourth embodiments in which the system further comprises a third fluid management element that pumps fluid into the patient interface device during a treatment, the third fluid management element being coupled to a synchronization mechanism that causes the first and third fluid management elements to pump equal amounts of fluid per unit time during a treatment. The twenty-fourth embodiments can be modified to form additional twenty-fourth embodiments in which the system further comprises a third fluid management element that pumps fluid into the patient interface device during a treatment, the third fluid management element being coupled to a synchronization mechanism that causes the first and third fluid management elements to pump equal amounts of fluid per unit time during a treatment. The twenty-fourth embodiments can be modified to form additional twenty-fourth embodiments in which the system further comprises a blood circuit that interfaces with the patient interface device and, through the latter, to the fluid circuit and wherein a diverted flow in the calibration configuration flows through a flow path between the first and second fluid management elements through a fluid accumulator connected to a pressure sensor that outputs said signal, wherein a fluid circuit portion connected to the patient interface device is separate from said flow path. The twenty-fourth embodiments can be modified to form additional twenty-fourth embodiments in which the controller is connected to a user interface and programmed to accept and store ultrafiltration data representing a target net ultrafiltration, wherein the controller is further programmed to control flow through said at least said one of said first and second fluid management elements responsively to said ultrafiltration data.

According to twenty-fifth embodiments, the disclosed subject matter includes a medical treatment system including a first pump that pumps fluid from a patient interface device during a treatment. A second pump that pumps fluid into a patient interface device during a treatment. The patient interface device being a device that interfaces with a patient fluid compartment including at least one of a dialyzer, a hemofilter, a hemodiafilter, an ultrafilter, and a plasmapheresis device. A controller connected to at least one of the first and second fluid management elements and having a processor programmed to regulate a net transfer of fluid into or from the patient interface device to achieve a predefined net removal of fluid from the patient during a therapeutic treatment implemented under control of the controller by regulating difference in the flow between the first pump and the second pump. A fluid circuit switch that allows a flow from the at least one of the first and second pumps to be selectively and automatically configured under control of the controller between a therapy configuration for delivering said therapeutic treatment to a calibration configuration in which an average flow difference between the flow in the first pump and the flow in the second pump is temporarily prevented and a flow or pressure sensor that outputs a signal indicating an instantaneous difference between the flow rates of the first and second pumps that occurs during a treatment. The controller being programmed to calculate and store flow correction data representing a correction to be applied to a rate of flow of said at least one of the first and second pumps responsively to said signal. The controller being further programmed to modify a flow rate of at least one of the first and second pumps responsively to said flow correction data.

The twenty-fifth embodiments can be modified to form additional twenty-fifth embodiments in which a diverted flow in the calibration configuration flows between the first and second pumps through a fluid accumulator connected to a pressure sensor that outputs said signal. The twenty-fifth embodiments can be modified to form additional twenty-fifth embodiments in which a diverted flow in the calibration configuration flows between the first and second pumps through a pressure sensor that outputs said signal. The twenty-fifth embodiments can be modified to form additional twenty-fifth embodiments in which the accumulator is configured such that pressure registered by said pressure sensor as due to a difference in the flow rates of said first and second pumps. The twenty-fifth embodiments can be modified to form additional twenty-fifth embodiments in which the first and/or second pump includes a peristaltic pump.

According to twenty-sixth embodiments, the disclosed subject matter includes a medical treatment system including a controller and control valve actuators and first and second pumps, the control valve actuators and pumps being controlled by said controller. The first pump being controlled to regulate flow toward a patient interface device and the second pump a being controlled to regulate flow from the same patient interface device. The patient interface device being a device that is separate from the claimed treatment system that interfaces with a patient fluid compartment including at least one of a dialyzer, a hemofilter, a hemodiafilter, an ultrafilter, and a plasmapheresis device. The controller including a processor programmed to regulate the speed of the first and second pumps to achieve a predefined net removal of fluid from the patient interface device during a treatment interval. The processing being further programmed to control the control valve actuators to switch between a first position that configures a fluid circuit, when attached to said control valves, in a bypass configuration which defines a bypass flow path that directly connects the first and second pumps such that a net flow from or into said bypass flow path is prevented as otherwise exists during the treatment. A pressure transducer connected to convey pressure signals to the controller, the pressure signals indicating pressure in the bypass flow path. The controller being programmed to calculate and store flow correction data representing a correction to be applied to a rate of flow of said at least one of the first and second pumps responsively to said signal. The controller being further programmed to modify a flow rate of said at least one of the first and second pumps responsively to said flow correction data.

The twenty-sixth embodiments can be modified to form additional twenty-sixth embodiments in which a flow in the bypass configuration flows between the first and second pumps through a fluid accumulator connected to a pressure sensor that outputs said signal. The twenty-sixth embodiments can be modified to form additional twenty-sixth embodiments in which the bypass flow path is such that pressure increases or decreases therein depending on an instantaneous difference in the flow rates of said first and second pumps. The twenty-sixth embodiments can be modified to form additional twenty-sixth embodiments in which the first and/or second pump includes a peristaltic pump.

According to twenty-seventh embodiments, the disclosed subject matter includes a method of regulating the balanced flow of fluids. The method includes, in a system having first and second fluid channels each with at least one respective pump for each of said first and second fluid channels, using a controller to control the rate of pumping of one or more of said respective pumps to establish flows in the first and second channels of equal volume flow rate based on calibration data stored in said controller. The method includes the first and second channels connecting to a fluid handling device in which a ratio of flow rates of entering and leaving flows to and from said fluid handling device is maintained by said controller. The method includes using the controller, temporarily establishing a calibration flow from said first channel to said second channel such that a measurable pressure change is indicated by a calibration pressure sensor in said calibration flow when a difference in flow rates of said respective pumps exists. The method includes, in response to said calibration pressure signal, using the controller, adjusting said calibration data. The method includes, thereafter, using said controller, adjusting one or more of said respective pumps according to the calibration data adjusted by said adjusting.

The twenty-seventh embodiments can be modified to form additional twenty-seventh embodiments in which said controller receives a local pressure upstream and/or downstream of at least one of said respective pumps, said adjusting being responsive to both of said calibration pressure signal and said local pressure signal. The twenty-seventh embodiments can be modified to form additional twenty-seventh embodiments in which said receiving a local pressure includes receiving local pressures upstream and downstream of said at least one of said respective pumps. The twenty-seventh embodiments can be modified to form additional twenty-seventh embodiments in which the controller controls a valve that selectively defines said calibration flow by routing flow through a predefined flow branch and said controller automatically selects a time of said temporarily establishing. The twenty-seventh embodiments can be modified to form additional twenty-seventh embodiments in which the fluid handling device is a blood treatment device. The twenty-seventh embodiments can be modified to form additional twenty-seventh embodiments in which the blood treatment device is a dialyzer or a hemofilter and replacement fluid source. The twenty-seventh embodiments can be modified to form additional twenty-seventh embodiments in which the respective pumps are peristaltic pumps.

Embodiments (which include the claims) refer to the generalization of a "patient interface device." This term designates any device that transfer fluid to or from a patient fluid such as blood or plasma or even an exogenous source of blood or patient body fluid which may be diluted or dehydrated by fluid exchange. Examples include a dialyzer, a hemofilter, a hemodiafilter, an ultrafilter, and a plasmapheresis device. It is noted that a hemofilter, for example, may further include an infusion port which provides the fluid inflow to a patient, an excess of which may tend to cause dilution and a single waste port of a hemofilter, an excess of flow through which may tend to cause dehydration. Thus, a patient interface device of a hemofiltration system may be said to include the filter and the infusion port. Any of the embodiments may be modified according to this general definition of patient interface device or any examples of such devices. For example, these may include devices that achieve separation of one fluid that must be balanced and other components, such as a centrifuge.

Note that as the term is used herein, "balanced" flow may refer to equal flows or flows that differ by a predefined amount, for example to account for ultrafiltration. During calibrations, balanced flows may have a zero differential, however, an arbitrary predefined offset from equal flows may still permit calibration, as should be clear to the skilled practitioner, and may be used to form variants, any of which is within the scope of the present disclosure.

It will be appreciated that the controllers, processes, systems, and sections described above can be implemented in hardware, hardware programmed by software, software instruction stored on a non-transitory computer readable medium or a combination of the above. For example, a method for balancing fluid flow can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of controllers and especially digital controllers and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, flow balancing devices, methods and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A system for performing a medical treatment, the system comprising:
   a controller;
   one or more controllable valve actuators;
   a first pump;
   a second pump, wherein the controllable valve actuators, the first pump and the second pump are controlled by the controller;
   the first pump being controlled to regulate a flow toward a patient interface device and the second pump a being controlled to regulate a flow from the same patient interface device;
   the patient interface device being a device that is separate from the system and interfaces with a patient fluid compartment including at least one of a dialyzer, a hemofilter, a hemodiafilter, an ultrafilter, and a plasmapheresis device;
   the controller being configured to regulate a speed of the first and second pumps to achieve a predefined net removal of fluid from the patient interface device during a treatment interval;
   the controller being further configured to control the control valve actuators to switch between a first position that configures a fluid circuit, when attached to said controllable valve actuators, in a bypass configuration which defines a bypass flow path that bypasses the patient interface device, and a second position which defines a flow path into and out of the patient interface device;
   a pressure transducer connected to convey pressure signals to the controller, the pressure signals indicating pressure in the bypass flow path;
   the controller being programmed to calculate and store flow correction data representing a correction to be applied to a rate of flow of said at least one of the first and second pumps responsively to said pressure signals; and
   the controller being further programmed to modify a flow rate of said at least one of the first and second pumps responsively to said flow correction data, wherein
   the system further comprises a third pump that pumps fluid into the patient interface device during a treatment, the third pump being coupled to a synchronization mechanism that causes the first and third pumps to pump equal amounts of fluid per unit time during the medical treatment.

2. The system of claim 1, wherein a diverted flow in the bypass configuration flows between the first and second pumps through a fluid accumulator connected to a pressure sensor that outputs said pressure signals.

3. The system of claim 2, wherein the fluid accumulator is configured such that pressure increases as fluid fills said fluid accumulator, whereby a difference in flow rates of the first pump and the second pump results in an increasing or decreasing pressure.

4. The system of claim 3, wherein the fluid accumulator has a residual volume of fluid to permit a measurement of a pressure change caused by a net removal or a net addition of fluid from or to said fluid accumulator.

5. The system of claim 1, wherein the first pump includes a peristaltic pump.

6. The system of claim 1, wherein the fluid circuit includes a disposable plastic tubing set and at least one control valve, the control valve including a tubing junction that interfaces with one or more pinch clamps to form selectable flow paths, the one or more pinch clamps being permanent reusable elements that pinch respective portions of the tubing set.

7. The system of claim 1, further comprising a blood circuit that interfaces with the patient interface device and, through the patient interface device, to the fluid circuit and wherein a diverted flow in the bypass configuration flows through a flow path between the first and second pumps through a fluid accumulator connected to a pressure sensor that outputs said pressure signals, wherein a fluid circuit portion connected to the patient interface device is separate from said flow path.

8. The system of claim 1, wherein the controller is connected to a user interface and programmed to accept and store ultrafiltration data representing a target net ultrafiltration, wherein the controller is further programmed to control flow through said at least said one of said first and second pumps responsively to said ultrafiltration data.

9. A method of regulating a balanced flow of fluids, comprising:
   in a system having first and second fluid channels each with at least one respective pump for each of said first and second fluid channels, using a controller to control a rate of pumping of one or more of said respective pumps to establish flows in the first and second fluid channels of equal volume flow rate based on calibration data stored in said controller;
   the first and second fluid channels connecting to a fluid handling device in which a ratio of flow rates of an entering flow to said fluid handling device and a leaving flow from said fluid handling device is maintained by said controller;
   using the controller, temporarily establishing a flow from said first fluid channel to said second fluid channel through a test flow branch with a pressure sensor and receiving a signal of a test branch pressure in said test flow branch at said controller; and
   in response to said test flow branch pressure signal, using the controller, adjusting said calibration data; and
   thereafter, using said controller, adjusting one or more of said respective pumps according to the calibration data adjusted by said adjusting,
   wherein the respective pumps are of a type that produce pressure pulses at regular intervals during pumping, the respective pumps being selected such that the pressure pulses of pumps flowing into and out of the test flow branch differ by at least a factor of two at pumping rates that occur times other than at times of said temporarily establishing.

10. The method of claim 9, wherein said controller receives a local pressure signal from upstream and/or downstream of at least one of said respective pumps, said adjusting being responsive to both said test flow branch pressure signal and said local pressure signal.

11. The method of claim 10, wherein said receiving the local pressure signal includes receiving the local pressures upstream and downstream of said at least one of said respective pumps.

12. The method of claim 9, wherein the controller controls a valve that selectively permits flow through said test flow branch and said controller automatically selects a time of said temporarily establishing.

13. The method of claim 9, wherein the controller controls a valve that selectively permits flow through said test flow branch and said controller automatically selects multiple instances of said temporarily establishing.

14. The method of claim 9, wherein the fluid handling device is a blood treatment device.

15. The method of claim 14, wherein the blood treatment device is a dialyzer or a hemofilter and replacement fluid source.

16. The method of claim 9, wherein said respective pumps are peristaltic pumps and pumping tube segments of no one of the respective pumps responsible for said entering flow has an inner diameter the same as a pumping tube segment inner diameter of a one of said respective pumps responsible for said leaving flow.

17. The method of claim 9, wherein said respective pumps are peristaltic pumps and a number of rollers for no one of the respective pumps responsible for said entering flow is the same as the number of the rollers of a one of said respective pumps responsible for said leaving flow.

* * * * *